U S009850428B2

(12) United States Patent
Tanaka et al.

(10) Patent No.: US 9,850,428 B2
(45) Date of Patent: Dec. 26, 2017

(54) COMPOUND HAVING POLY (DIFLUOROMETHYLENE) CHAIN, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Hiroyuki Tanaka, Ichihara (JP); Masakazu Yano, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/951,954

(22) Filed: Nov. 25, 2015

(65) Prior Publication Data
US 2016/0168466 A1 Jun. 16, 2016

(30) Foreign Application Priority Data

Nov. 27, 2014 (JP) ................................ 2014-239785
Mar. 19, 2015 (JP) ................................ 2015-056286

(51) Int. Cl.
| G02F 1/1333 | (2006.01) |
| C09K 19/56 | (2006.01) |
| C09K 19/34 | (2006.01) |
| C09K 19/30 | (2006.01) |
| C07C 31/38 | (2006.01) |
| C07C 43/13 | (2006.01) |
| C07C 33/42 | (2006.01) |
| C09K 19/32 | (2006.01) |

(Continued)

(52) U.S. Cl.
CPC .............. *C09K 19/56* (2013.01); *C07C 31/38* (2013.01); *C07C 33/423* (2013.01);
(Continued)

(58) Field of Classification Search
CPC ................ C09K 19/56; C09K 19/3001; C09K 19/3059; C09K 19/3066; C09K 19/3068; C09K 19/32; C09K 19/322; C09K 19/3402; C09K 19/3458; C09K 19/54; C09K 2019/0444; C09K 2019/0448; C09K 2019/122; C09K 2019/123; C09K 2019/2035; C09K 2019/3004; C09K 2019/301; C09K 2019/3016; C09K 2019/3036; C09K 2019/3071; C09K 2019/3075; C09K 2019/3077; C09K 2019/3078; C09K 2019/308; C09K 2019/3083; C09K 2019/3084; C09K 2019/3422; C09K 2019/3425; C07C 31/38; C07C 33/423; C07C 43/137; G02F 1/1333

(Continued)

(56) References Cited

U.S. PATENT DOCUMENTS

| 8,920,674 B2 * | 12/2014 | Yanai ..................... C09K 19/42 |
| | | 252/299.01 |
| 8,999,196 B2 * | 4/2015 | Tanaka ................. C09K 19/061 |
| | | 252/299.6 |

(Continued)

FOREIGN PATENT DOCUMENTS

| JP | 50035076 A | 4/1975 |
| JP | 2013-060417 A | 4/2013 |
| WO | 2012-104008 A1 | 8/2012 |

OTHER PUBLICATIONS

Pensec et al., "Synthesis and Structural Studies of Polyphilic Mesogens with Central or Terminal Perfluoroalkyl Chains", Journal of Physical Chemistry B (1998), 102(1), 52-60.*

(Continued)

*Primary Examiner* — Geraldina Visconti
(74) *Attorney, Agent, or Firm* — Hogan Lovells US LLP

(57) ABSTRACT

A polar compound has a high chemical stability, high ability to align liquid crystal molecules and high solubility in a liquid crystal composition, and causes no decrease of liquid crystallinity of the liquid crystal composition, a liquid crystal composition contains the compound, and a liquid crystal display device includes the composition.
The compound is represented by formula (1), the composition contains the compound, and the liquid crystal display device uses the composition.

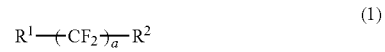

In formula (1), $R^1$ is alkyl having 3 to 15 carbons, alkenyl having 4 to 15 carbons or the like; a is an integer from 2 to 12; and $R^2$ is a group represented by formula (1a), formula (1b) or formula (1c).

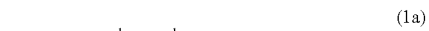
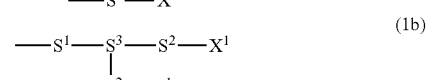
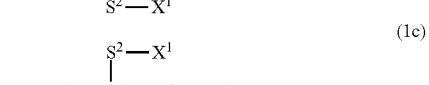

In the formulas, $S^1$ and $S^2$ are independently a single bond, alkylene having 1 to 10 carbons; $S^3$ is >CH— or >N—; $S^4$ is >C< or >Si<; and $X^1$ is —OH, —NH$_2$ or the like.

29 Claims, No Drawings

(51) Int. Cl.

| | |
|---|---|
| *C09K 19/54* | (2006.01) |
| *C09K 19/04* | (2006.01) |
| *C09K 19/12* | (2006.01) |
| *C09K 19/20* | (2006.01) |

(52) U.S. Cl.
CPC ........ *C07C 43/137* (2013.01); *C09K 19/3001* (2013.01); *C09K 19/3059* (2013.01); *C09K 19/3066* (2013.01); *C09K 19/3068* (2013.01); *C09K 19/32* (2013.01); *C09K 19/322* (2013.01); *C09K 19/3402* (2013.01); *C09K 19/3458* (2013.01); *C09K 19/54* (2013.01); *C09K 2019/0444* (2013.01); *C09K 2019/0448* (2013.01); *C09K 2019/122* (2013.01); *C09K 2019/123* (2013.01); *C09K 2019/2035* (2013.01); *C09K 2019/301* (2013.01); *C09K 2019/3004* (2013.01); *C09K 2019/308* (2013.01); *C09K 2019/3016* (2013.01); *C09K 2019/3036* (2013.01); *C09K 2019/3071* (2013.01); *C09K 2019/3075* (2013.01); *C09K 2019/3077* (2013.01); *C09K 2019/3078* (2013.01); *C09K 2019/3083* (2013.01); *C09K 2019/3084* (2013.01); *C09K 2019/3422* (2013.01); *C09K 2019/3425* (2013.01)

(58) Field of Classification Search
USPC .............................. 252/299.4, 299.6; 428/1.1
See application file for complete search history.

(56) References Cited

U.S. PATENT DOCUMENTS

| | | |
|---|---|---|
| 2013/0048913 A1 | 2/2013 | Tanaka |
| 2013/0314655 A1 | 11/2013 | Archetti et al. |

OTHER PUBLICATIONS

E.H. Lee, et al., "Alignment of Perfluorinated Supramolecular Columns on the Surfaces of Various Self-Assembled Monolayers," Macromolecules 2005, vol. 38, pp. 5152-5157.

E. Klein, et al., "HFP Fluorinated Cationic Lipids for Enhanced Lipoplex Stability and Gene Delivery," Bioconjugate Chem. 2010, vol. 21, pp. 360-371.

Y. Chaudier, et al., "Synthesis and Preliminary Assessments of Hybrid Hydrocarbon-Fluorocarbon Anionic and Non-Ionic Surfactants," Tetrahedron Letters 2001, vol. 42, pp. 3583-3585.

* cited by examiner

COMPOUND HAVING POLY (DIFLUOROMETHYLENE) CHAIN, LIQUID CRYSTAL COMPOSITION AND LIQUID CRYSTAL DISPLAY DEVICE

TECHNICAL FIELD

The invention relates to a compound having a poly (difluoromethylene) chain, a liquid crystal composition and a liquid crystal display device. More specifically, the invention relates to a compound having difluoromethylene, a liquid crystal composition that contains the compound and has a positive or negative dielectric anisotropy, and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type based on a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving characteristics of the composition. Table 1 below summarizes a relationship of the characteristics between two aspects. The characteristics of the composition will be further described based on a commercially available AM device. A temperature range of the nematic phase relates to a temperature range in which the device can be used. A preferred maximum temperature of the nematic phase is approximately 70° C. or higher, and a preferred minimum temperature of the nematic phase is approximately −10° C. or lower. Viscosity of the liquid crystal composition relates to a response time of the device. A short response time is preferred for displaying moving images on the device. A shorter response time even by one millisecond is desirable. Accordingly, a small viscosity of the composition is preferred. A small viscosity at a low temperature is further preferred.

TABLE 1

| | Characteristics of Composition and AM Device | |
|---|---|---|
| No. | Characteristics of Composition | Characteristics of AM Device |
| 1 | Wide temperature range of a nematic phase | Wide usable temperature range |
| 2 | Small viscosity[1] | Short response time |
| 3 | Suitable optical anisotropy | Large contrast ratio |

TABLE 1-continued

| | Characteristics of Composition and AM Device | |
|---|---|---|
| No. | Characteristics of Composition | Characteristics of AM Device |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |
| 7 | Large elastic constant | Large contrast ratio and short response time |

[1] A liquid crystal composition can be injected into a liquid crystal display device in a short time.

An optical anisotropy of the composition relates to a contrast ratio in the device. According to a mode of the device, a large optical anisotropy or a small optical anisotropy, more specifically, a suitable optical anisotropy is required. A product (Δn×d) of the optical anisotropy (Δn) of the composition and a cell gap (d) in the device is designed so as to maximize the contrast ratio. A suitable value of the product depends on a type of the operating mode. In a device having a TN mode or the like, the suitable value is approximately 0.45 micrometer. In a device having the VA mode, the suitable value is in the range of approximately 0.30 micrometer to approximately 0.40 micrometer, and in a device having the IPS mode or the FFS mode, the suitable value is in the range of approximately 0.20 micrometer to approximately 0.30 micrometer. In the above cases, a composition having a large optical anisotropy is preferred for a device having a small cell gap. A large dielectric anisotropy in the composition contributes to a low threshold voltage, a small electric power consumption and a large contrast ratio in the device. Accordingly, the large positive or negative dielectric anisotropy is preferred. A large specific resistance in the composition contributes to a large voltage holding ratio and a large contrast ratio in the device. Accordingly, a composition having the large specific resistance at room temperature and also at a temperature close to the maximum temperature of the nematic phase in an initial stage is preferred. The composition having the large specific resistance at room temperature and also at a temperature close to the maximum temperature of the nematic phase after the device has been used for a long period of time is preferred. Stability of the composition to ultraviolet light and heat relates to a service life of the device. In the case where the stability is high, the device has a long service life. Such characteristics are preferred for an AM device used in a liquid crystal projector, a liquid crystal television and so forth.

In a liquid crystal display device having a polymer sustained alignment (PSA) mode, a liquid crystal composition containing a polymer is used. First, a composition to which a small amount of a polymerizable compound is added is injected into the device. Then, the composition is irradiated with ultraviolet light while voltage is applied between substrates of the device. The polymerizable compound is polymerized to form a network structure of the polymer in the liquid crystal composition. In the composition, alignment of the liquid crystal molecules can be controlled by the polymer, and therefore the response time of the device is shortened and also image persistence is improved. Such an effect of the polymer can be expected for a device having the mode such as the TN mode, the ECB mode, the OCB mode, the IPS mode, the VA mode, the FFS mode and the FPA mode.

The liquid crystal composition is prepared by mixing liquid crystal compounds. An additive such as the polymerizable compound, a polymerization initiator, a polymerization inhibitor, an optically active compound, an antioxidant, an ultraviolet light absorber, a light stabilizer, a heat stabilizer and an antifoaming agent is added to the composition when necessary. A polar compound is occasionally added thereto. A polar group has interaction with a surface of the substrate in the device, and therefore the compound is arranged on the substrate. The liquid crystal molecules are preliminarily aligned according to the arrangement before voltage is applied thereto. Accordingly, the response time of the device is to be shortened. Expectation has been expressed for the polar compound that efficiently induces such an effect.

CITATION LIST

Patent Literature

Patent literature No. 1: JP 2013-60417 A.
Patent literature No. 2: WO 2012-104008 A.
Patent literature No. 3: JP S50-35076 A.

Non-Patent Literature

Non-patent literature No. 1: Macromolecules, 2005, 38, 5152.
Non-patent literature No. 2: Bioconjugate Chemistry, 2010, 21, 360.
Non-patent literature No. 3: Tetrahedron Letters 2001, 42, 3583.

SUMMARY OF INVENTION

Technical Problem

A first object of the invention is to provide a polar compound that has a high chemical stability, a high ability to align liquid crystal molecules and a high solubility in a liquid crystal composition, and causes no decrease of liquid crystallinity of the liquid crystal composition. A second object is to provide a liquid crystal composite that contains the compound and satisfies at least one of characteristics such as a high maximum temperature of a nematic phase, a low minimum temperature of the nematic phase, a small viscosity, a suitable optical anisotropy, a large positive or negative dielectric anisotropy, a large specific resistance, a high stability to ultraviolet light, a high stability to heat and a large elastic constant. A third object is to provide a liquid crystal display device that contains the composition and has characteristics such as a wide temperature range in which the device can be used, a short response time, a high voltage holding ratio, a low threshold voltage, a large contrast ratio and a long service life.

Solution to Problem

The invention concerns a compound represented by formula (1), a liquid crystal composition containing the compound, and a liquid crystal display device including the composition:

wherein, in formula (1), $R^1$ is alkyl having 3 to 5 carbons, alkyl having 2 to 15 carbons in which at least one of —$CH_2$— is replaced by —O—, or alkenyl having 4 to 15 carbons, and in the groups, at least one of hydrogen may be replaced by fluorine or chlorine;

a is an integer from 2 to 12; and $R^2$ is a group represented by formula (1a), formula (1b) or formula (1c):

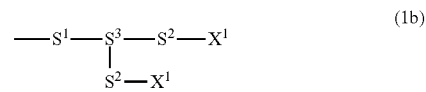

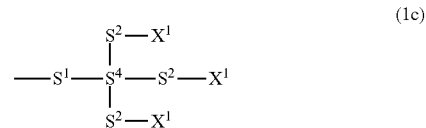

wherein, in formula (1a), formula (1b) and formula (1c), $S^1$ and $S^2$ are independently a single bond or alkylene having 1 to 10 carbons, and in the alkylene, at least one of —$CH_2$— may be replaced by —O—, —NH—, —CO—, —COO—, —OCO— or —OCOO—, at least one of —$(CH_2)_2$— may be replaced by —CH=CH—, and in the groups, at least one of hydrogen may be replaced by fluorine or chlorine;

$S^3$ is >CH— or >N—;

$S^4$ is >C< or >Si<;

$X^1$ is —OH, —$NH_2$ or a group represented by —$OR^3$, —$N(R^3)_2$ or —$Si(R^3)_3$, in which $R^3$ is hydrogen or alkyl having 1 to 10 carbons, and in the alkyl, at least one of —$CH_2$— may be replaced by —O—, at least one of —$(CH_2)_2$— may be replaced by —CH=CH—, and in the groups, at least one of hydrogen may be replaced by fluorine or chlorine;

in which, in formula (1), a sum of carbons in $R^1$, $S^1$, $S^2$, $S^3$ and $S^4$, and carbons in —$(CF_2)_a$— is at least 11; and in which, when $R^2$ is a group represented by formula (1a), $S^1$ is —$(CH_2)_2$— and $X^1$ is —OH, a is 2, 3, 5, 7, 9, 10, 11 or 12; and when $R^2$ is a group represented by formula (1a), $S^1$ is —$(CH_2)_3$— and $X^1$ is —OH, a is 2, 3, 4, 5, 6, 7, 9, 10, 11 or 12.

Advantageous Effects of Invention

A first advantage of the invention is to provide a polar compound that has a high chemical stability, a high ability to align liquid crystal molecules and a high solubility in a liquid crystal composition, and causes no decrease of liquid crystallinity of the liquid crystal composition. A second advantage is to provide a liquid crystal composite that contains the compound and satisfies at least one of characteristics such as a high maximum temperature of a nematic phase, a low minimum temperature of the nematic phase, a small viscosity, a suitable optical anisotropy, a large positive or negative dielectric anisotropy, a large specific resistance, a high stability to ultraviolet light, a high stability to heat and a large elastic constant. A third advantage is to provide a liquid crystal display device that includes the composition and has characteristics such as a wide temperature range in which the device can be used, a short response time, a high voltage holding ratio, a low threshold voltage, a large contrast ratio and a long service life.

DESCRIPTION OF EMBODIMENTS

Usage of terms herein is as described below. Terms "liquid crystal composition" and "liquid crystal display device" are occasionally abbreviated as "composition" and "device," respectively. "Liquid crystal display device" is a generic term for a liquid crystal display panel and a liquid crystal display module. "Liquid crystal compound" is a generic term for a compound having a liquid crystal phase such as a nematic phase and a smectic phase, and a compound having no liquid crystal phase but to be mixed with a composition for the purpose of adjusting characteristics such as a temperature range of the nematic phase, viscosity and dielectric anisotropy. The compound has a six-membered ring such as 1,4-cyclohexylene and 1,4-phenylene, and has rod-like molecular structure. "Polymerizable compound" includes a compound to be added to the composition for the purpose of forming a polymer in the composition. "Polar compound" assists alignment of liquid crystal molecules by a polar group interacting with a surface of a substrate.

The liquid crystal composition is prepared by mixing a plurality of liquid crystal compounds. A ratio (content) of the liquid crystal compounds is expressed in terms of weight percent (% by weight) based on the weight of the liquid crystal composition. An additive such as an optically active compound, an antioxidant, an ultraviolet light absorber, a dye, an antifoaming agent, the polymerizable compound, a polymerization initiator, a polymerization inhibitor and a polar compound is added to the liquid crystal composition when necessary. A ratio (content) of the additive is expressed in terms of weight percent (% by weight) based on the weight of the liquid crystal composition in a manner similar to the ratio of the liquid crystal compound. Weight parts per million (ppm) is occasionally used. A ratio of the polymerization initiator and the polymerization inhibitor is not expressed on above but is expressed based on the weight of the polymerizable compound.

A compound represented by formula (1) is occasionally abbreviated as "compound (1)." "Compound (1)" means one compound represented by formula (1), a mixture of two compounds or a mixture of three or more compounds. The same rule applies also to at least one compound selected from the group of compounds represented by formula (2), or the like. A symbol $B^1$, $C^1$, F or the like surrounded by a hexagonal shape corresponds to ring $B^1$, ring $C^1$, ring F or the like, respectively. The hexagonal shape represents a six-membered ring such as a cyclohexane ring and a benzene ring, or a condensed ring such as a naphthalene ring. An oblique line crossing the hexagonal shape represents that arbitrary hydrogen on the ring may be replaced a group such as -$Sp^1$-$P^1$. A subscript such as e represents the number of groups subjected to replacement. When the subscript is 0, no such replacement exists.

A symbol of a terminal group $R^{11}$ is used for a plurality of component compounds. In the compounds, two groups represented by two of arbitrary $R^{11}$ may be identical or different. In one case, for example, $R^{11}$ of compound (2) is ethyl and $R^{11}$ of compound (3) is ethyl. In another case, for example, $R^{11}$ of compound (2) is ethyl and $R^{11}$ of compound (3) is propyl. The same rule applies also to a symbol of any other terminal group, ring and a bonding group or the like.

In formula (8), when i is 2, two of ring $D^1$ exists. In the compound, two groups represented by two of ring $D^1$ may be identical or different. The same rule applies also to two of arbitrary ring $D^1$ when i is larger than 2. The same rule applies also to a symbol of any other ring, a bonding group or the like.

An expression "at least one of 'A'" means that the number of 'A' is arbitrary. An expression "at least one of 'A' may be replaced by 'B'" means that, when the number of 'A' is 1, a position of 'A' is arbitrary, and also when the number of 'A' is 2 or more, positions thereof can also be selected without restriction. The same rule applies also to an expression "at least one of 'A' is replaced by 'B'." An expression "at least one of A may be replaced by B, C or D" means inclusion of a case where at least one of A is replaced by B, a case where at least one of A is replaced by C, and a case where at least one of A is replaced by D, and also a case where a plurality of A are replaced by at least two of B, C and D. For example, alkyl in which at least one of —$CH_2$— (or —$CH_2CH_2$—) may be replaced by —O— (or —CH=CH—) includes alkyl, alkenyl, alkoxy, alkoxyalkyl, alkoxyalkenyl and alkenyloxyalkyl. In addition, a case where replacement of two consecutive —$CH_2$— by —O— results in forming —O—O— is not preferred. In the alkyl or the like, a case where replacement of —$CH_2$— of a methyl part (—$CH_2$—H) by —O— results in forming —O—H is not preferred, either.

Halogen means fluorine, chlorine, bromine and iodine. Preferred halogen is fluorine and chlorine. Further preferred halogen is fluorine. Alkyl is straight-chain alkyl or branched-chain alkyl, but includes no cyclic alkyl. In general, straight-chain alkyl is preferred to branched-chain alkyl. The same rule applies also to a terminal group such as alkoxy and alkenyl. With regard to a configuration of 1,4-cyclohexylene, trans is preferred to cis for increasing the maximum temperature of the nematic phase. Then, 2-fluoro-1,4-phenylene means two divalent groups described below. In a chemical formula, fluorine may be leftward (L) or rightward (R). The same rule applies also to an asymmetrical divalent group formed by removing two of hydrogen from a ring such as tetrahydropyran-2,5-diyl.

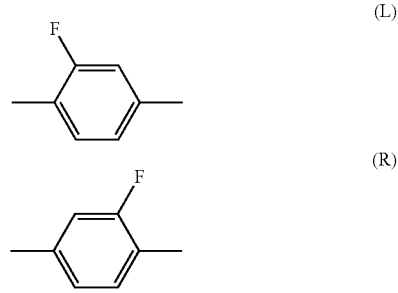

The invention includes items described below.
Item 1. A compound, represented by formula (1):

wherein, in formula (1),
$R^1$ is alkyl having 3 to 15 carbons, alkyl having 2 to 15 carbons in which at least one of —$CH_2$— is replaced by —O— or alkenyl having 4 to 15 carbons, and in the groups, at least one of hydrogen may be replaced by fluorine or chlorine;
a is an integer from 2 to 12; and $R^2$ is a group represented by formula (1a), formula (1b) or formula (1c):

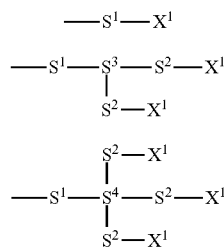

(1a)
(1b)
(1c)

wherein, in formula (1a), formula (1b) and formula (1c), $S^1$ and $S^2$ are independently a single bond or alkylene having 1 to 10 carbons, and in the alkylene, at least one of —$CH_2$— may be replaced by —O—, —NH—, —CO—, —COO—, —OCO— or —OCOO—, and at least one of —$(CH_2)_2$— may be replaced by —CH═CH—, and in the groups, at least one of hydrogen may be replaced by fluorine or chlorine;

$S^3$ is >CH— or >N—;

$S^4$ is >C< or >Si<;

$X^1$ is —OH, —$NH_2$ or a group represented by —$OR^3$, —$N(R^3)_2$ or —$Si(R^3)_3$, in which $R^3$ is hydrogen or alkyl having 1 to 10 carbons, and in the alkyl, at least one of —$CH_2$— may be replaced by —O—, at least one of —$(CH_2)_2$— may be replaced by —CH═CH—, and in the groups, at least one of hydrogen may be replaced by fluorine or chlorine;

in which, in formula (1), a sum of carbons in $R^1$, $S^1$, $S^2$, $S^3$ and $S^4$, and carbons in —$(CF_2)_a$— is at least 11; and in which, when $R^2$ is a group represented by formula (1a), $S^1$ is —$(CH_2)_2$— and $X^1$ is —OH, a is 2, 3, 5, 7, 9, 10, 11 or 12; and when $R^2$ is a group represented by formula (1a), $S^1$ is —$(CH_2)_3$— and $X^1$ is —OH, a is 2, 3, 4, 5, 6, 7, 9, 10, 11 or 12.

Item 2. The compound according to item 1, wherein, in formula (1), $R^2$ is a group represented by formula (1a) or (1b).

Item 3. The compound according to item 1 or 2, wherein, in formula (1), $R^2$ is a group represented by formula (1a) or (1b), and in formula (1a) and formula (1b), $X^1$ is —OH, —$NH_2$ or a group represented by $Si(R^3)_3$, in which $R^3$ is alkyl having 1 to 10 carbons or alkoxy having 1 to 9 carbons.

Item 4. The compound according to any one of items 1 to 3, represented by formula (1-1) or (1-2):

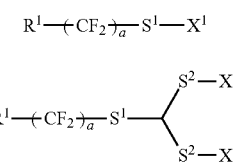

(1-1)
(1-2)

wherein, in formula (1-1) and formula (1-2), $R^1$ is alkyl having 3 to 15 carbons, alkoxy having 2 to 14 carbons, alkoxyalkyl having 2 to 14 carbons or alkenyl having 4 to 15 carbons;

a is an integer from 2 to 7;

$S^1$ and $S^2$ are independently a single bond or alkylene having 1 to 5 carbons, and in the alkylene, one of —$CH_2$— may be replaced by —O— or —NH—, and one of —$(CH_2)_2$— may be replaced by —CH═CH—;

$X^1$ is —OH, —$NH_2$ or a group represented by —$Si(R^3)_3$, in which $R^3$ is alkyl having 1 to 5 carbons or alkoxy having 1 to 4 carbons;

in which, in formula (1-1), a sum of carbons in $R^1$ and $S^1$, and carbons in —$(CF_2)_a$— is at least 11; and when $S^1$ is —$(CH_2)_2$— and $X^1$ is —OH, a is 2, 3, 5 or 7; and in which, in formula (1-2), a sum of carbons in $R^1$, $S^1$ and $S^2$, and carbons in —$(CF_2)_a$— is at least 10.

Item 5. The compound according to any one of items 1 to 4, represented by formula (1-3) or (1-4):

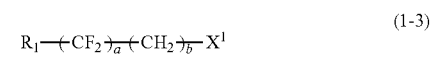

(1-3)

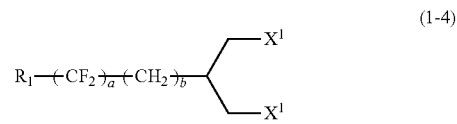

(1-4)

wherein, in formula (1-3) and formula (1-4), $R^1$ is alkyl having 3 to 10 carbons, alkoxy having 2 to 9 carbons, alkoxyalkyl having 2 to 9 carbons or alkenyl having 4 to 10 carbons;

a is an integer from 2 to 7;

b is an integer from 1 to 3; and $X^1$ is —OH, —$NH_2$, —$Si(CH_3)_3$, —$Si(C_2H_5)_3$, —$Si(OCH_3)_3$ or —$Si(OC_2H_5)_3$;

in which, in formula (1-3), a sum of carbons in $R^1$, carbons in —$(CF_2)_a$— and carbons in —$(CH_2)_b$— is at least 11; and when b is 2 and $X^1$ is —OH, a is 2, 3, 5 or 7; and in which, in formula (1-4), a sum of carbons in $R^1$, carbons in —$(CF_2)_a$— and carbons in —$(CH_2)_b$— is at least 8.

Item 6. The compound according to any one of items 1 to 5, represented by any one of formulas (1-5) to (1-18):

(1-5)

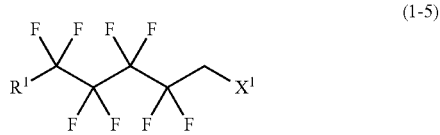

(1-6)

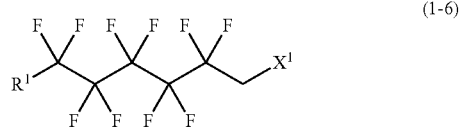

(1-7)

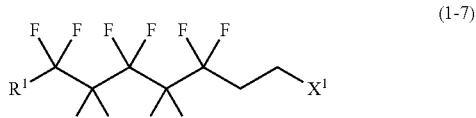

(1-8)

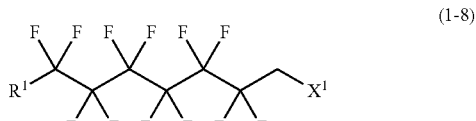

(1-9)

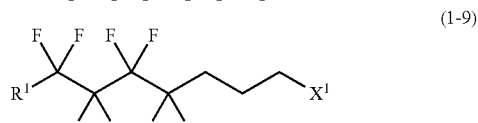

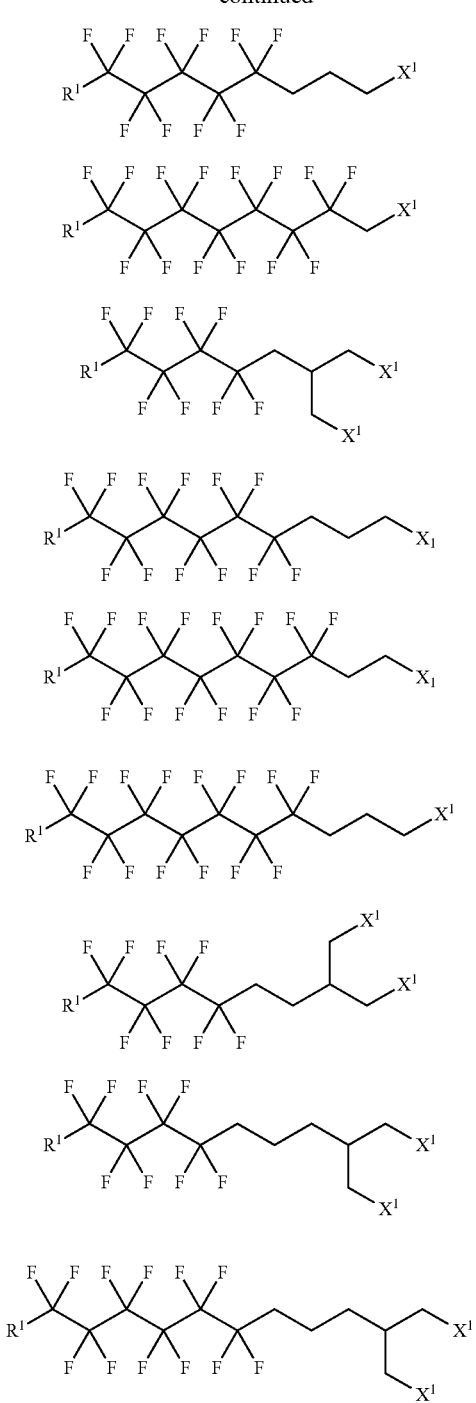

wherein, in formula (1-5) to formula (1-18), $X^1$ is —OH, —Si(CH$_3$)$_3$, —Si(C$_2$H$_5$)$_3$; —Si(OCH$_3$)$_3$ or —Si(OC$_2$H$_5$)$_3$; in formula (1-5), $R^1$ is alkyl having 6 to 10 carbons, alkoxyalkyl having 6 to 9 carbons or alkenyl having 6 to 10 carbons; in formula (1-6), $R^1$ is alkyl having 5 to 10 carbons, alkoxyalkyl having 5 to 9 carbons or alkenyl having 5 to 10 carbons; in formula (1-7) to formula (1-9), $R^1$ is alkyl having 4 to 10 carbons, alkoxyalkyl having 4 to 9 carbons or alkenyl having 4 to 10 carbons; in formula (1-10) to formula (1-12), $R^1$ is alkyl having 3 to 10 carbons, alkoxyalkyl having 3 to 9 carbons or alkenyl having 4 to 10 carbons; and in formula (1-13) to formula (1-18), $R^1$ is alkyl having 3 to 10 carbons, alkoxy having 2 to 9 carbons or alkenyl having 4 to 10 carbons.

Item 7. The compound according to any one of items 1 to 6, represented by any one of formulas (1-19) to (1-32):

(1-30)
(1-31)
(1-32)

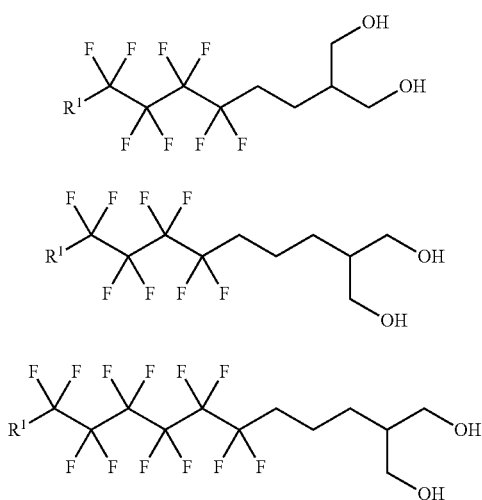

wherein, in formula (1-19), $R^1$ is alkyl having 6 to 10 carbons, alkoxyalkyl having 6 to 9 carbons or alkenyl having 6 to 10 carbons; in formula (1-20), $R^1$ is alkyl having 5 to 10 carbons, alkoxyalkyl having 5 to 9 carbons or alkenyl having 5 to 10 carbons; in formula (1-21) to formula (1-23), $R^1$ is alkyl having 4 to 10 carbons, alkoxyalkyl having 4 to 9 carbons or alkenyl having 4 to 10 carbons; in formula (1-24) to formula (1-26), $R^1$ is alkyl having 3 to 10 carbons, alkoxyalkyl having 3 to 9 carbons or alkenyl having 4 to 10 carbons; and in formula (1-27) to formula (1-32), $R^1$ is alkyl having 3 to 10 carbons, alkoxy having 2 to 9 carbons or alkenyl having 4 to 10 carbons.

Item 8. The compound according to any one of items 1 to 7, represented by any one of formulas (1-33) to (1-42):

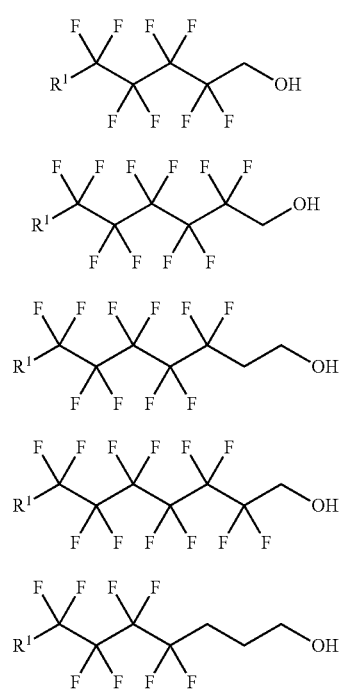

(1-33)
(1-34)
(1-35)
(1-36)
(1-37)

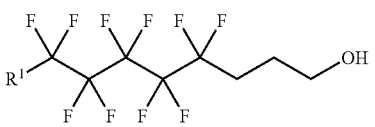
(1-38)

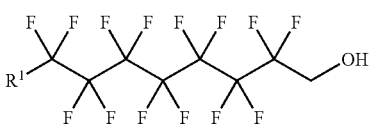
(1-39)

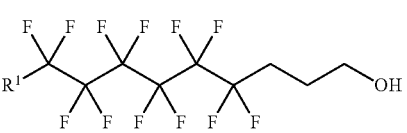
(1-40)

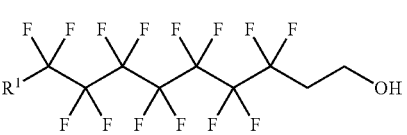
(1-41)

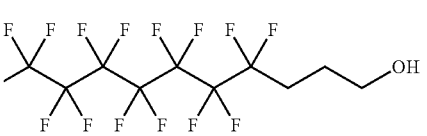
(1-42)

wherein, in formula (1-33), $R^1$ is alkyl having 6 to 10 carbons or alkoxyalkyl having 6 to 9 carbons; in formula (1-34), $R^1$ is alkyl having 5 to 10 carbons or alkoxyalkyl having 5 to 9 carbons; in formula (1-35) to formula (1-37), $R^1$ is alkyl having 4 to 10 carbons or alkoxyalkyl having 4 to 9 carbons; in formula (1-38) to formula (1-39), $R^1$ is alkyl having 3 to 10 carbons or alkoxyalkyl having 3 to 9 carbons; and in formula (1-40) to formula (1-42), $R^1$ is alkyl having 3 to 10 carbons or alkoxy having 2 to 9 carbons.

Item 9. The compound according to any one of items 1 to 8, represented by any one of formulas (1-43) to (1-48):

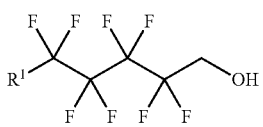
(1-43)

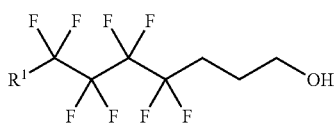
(1-44)

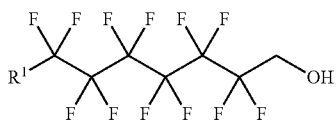
(1-45)

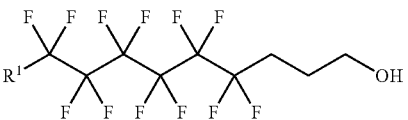
(1-46)

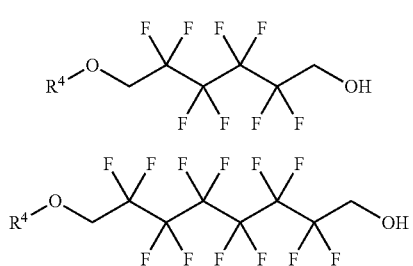

(1-47)

(1-48)

wherein, in formula (1-43), $R^1$ is alkyl having 6 to 10 carbons; in formula (1-44) and formula (1-45), $R^1$ is alkyl having 4 to 10 carbons; in formula (1-46), $R^1$ is alkyl having 3 to 10 carbons; in formula (1-47), $R^4$ is alkyl having 5 to 8 carbons; and in formula (1-48), $R^4$ is alkyl having 3 to 8 carbons.

Item 10. A liquid crystal composition, containing at least one compound according to any one of items 1 to 9 as a first additive.

Item 11. The liquid crystal composition according to item 10, further containing at least one compound selected from the group of compounds represented by formulas (2) to (4):

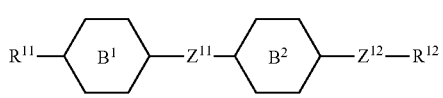

(2)

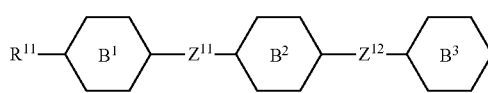

(3)

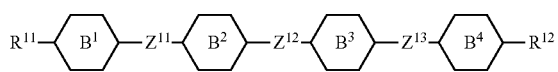

(4)

wherein, in formula (2) to formula (4), $R^{11}$ and $R^{12}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C—, or —COO—.

Item 12. The liquid crystal composition according to item 10 or 11, further containing at least one compound selected from the group of compounds represented by formulas (5) to (7):

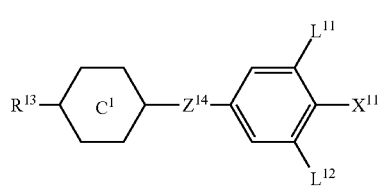

(5)

(6)

(7)

wherein, in formula (5) to formula (7), $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{11}$ is fluorine, chlorine, —$OCF_3$, —$OCHF_2$, —$CF_3$, —$CHF_2$, —$OCF_2CHF_2$ or —$OCF_2CHFCF_3$;

ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 13. The liquid crystal composition according to item 10 or 11, further containing at least one compound selected from the group of compounds represented by formula (8):

(8)

wherein, in formula (8), $R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{12}$ is or —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 14. The liquid crystal composition according to item 10 or 11, further containing at least one compound selected from the group of compounds represented by formulas (9) to (15):

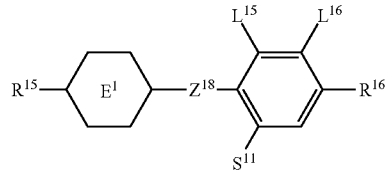 (9)

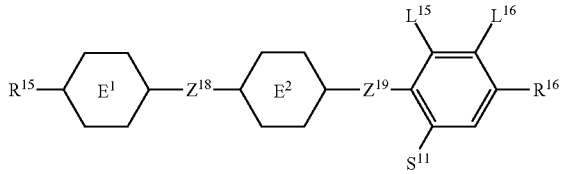 (10)

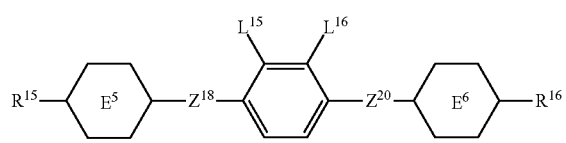 (11)

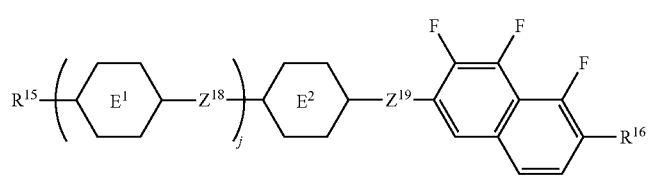 (12)

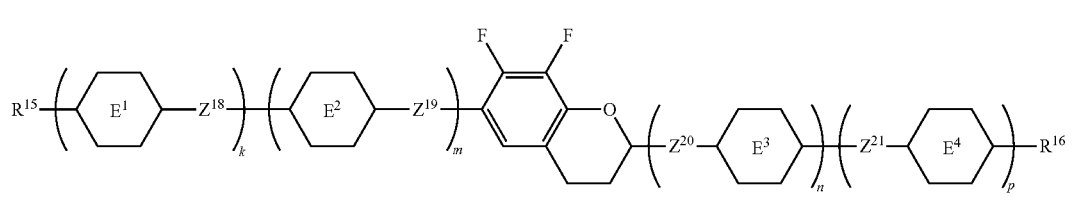 (13)

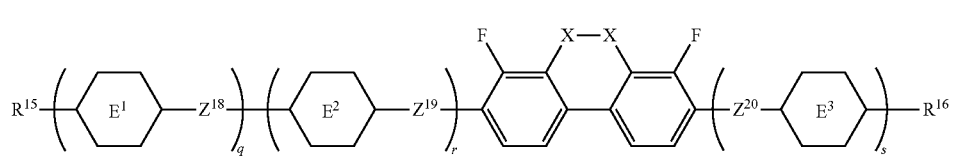 (14)

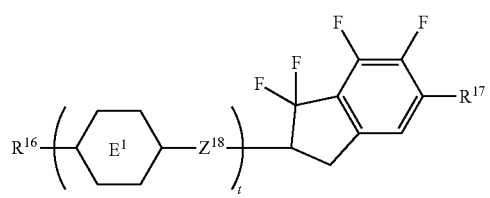 (15)

wherein, in formula (9) to formula (15), $R^{15}$ and $R^{16}$ are independently alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

$R^{17}$ is hydrogen, fluorine, alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{29}$ and $Z^{21}$ are independently a single bond, —CH$_2$CH$_2$—, —COO—, —CH$_2$O—, —OCF$_2$— or —OCF$_2$CH$_2$CH$_2$—;

$L^{15}$ and $L^{16}$ are independently fluorine or chlorine;

$S^{11}$ is hydrogen or methyl;

X is —CHF— or —CF$_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 15. The liquid crystal composition according to any one of items 10 to 14, containing at least one polymerizable compound selected from the group of compounds represented by formula (16) as a second additive:

(16)

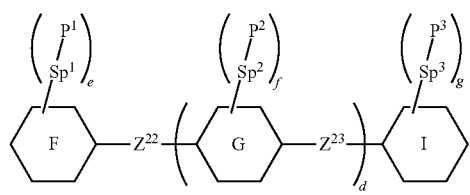

wherein, in formula (16), ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen;

ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen;

$Z^{22}$ and $Z^{23}$ are independently a single bond or alkylene having 1 to 10 carbons, and in the alkylene, at least one of —$CH_2$— may be replaced by —O—, —CO—, —COO— or —OCO—, and at least one of —$CH_2CH_2$— may be replaced by —CH=CH—, —C($CH_3$)=CH—, —CH=C($CH_3$)— or —C($CH_3$)=C($CH_3$)—, and in the groups, at least one of hydrogen may be replaced by fluorine or chlorine;

$P^1$, $P^2$ and $P^3$ are independently a polymerizable group;

$Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2CH_2$— may be replaced by —CH=CH— or —C≡C—, and in the groups, at least one of hydrogen may be replaced by fluorine or chlorine;

d is 0, 1 or 2; and e, f and g are independently 0, 1, 2, 3 or 4, and a sum of e, f and g is 1 or more.

Item 16. The liquid crystal composition according to item 15, wherein, in formula (16) described in item 15, $P^1$, $P^2$ and $P^3$ are independently a polymerizable group selected from the group of groups represented by formulas (P-1) to (P-5):

(P-1)

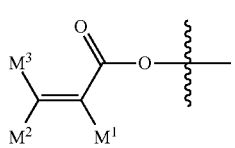

(P-2)

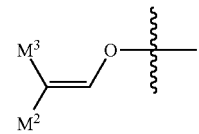

(P-3)

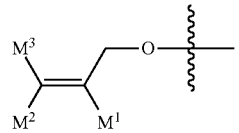

(P-4)

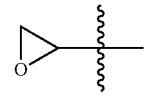

(P-5)

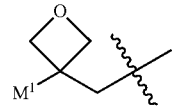

wherein, in formula (P-1) to formula (P-5), $M^1$, $M^2$ and $M^3$ are independently hydrogen, fluorine, alkyl having 1 to 5 carbons, or alkyl having 1 to 5 carbons in which at least one of hydrogen is replaced by halogen.

Item 17. The liquid crystal composition according to any one of items 10 to 16, containing at least one polymerizable compound selected from the group of compounds represented by formulas (16-1) to (16-7) as the second additive:

(16-1)

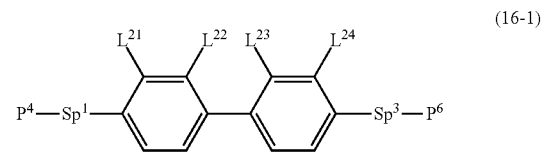

(16-2)

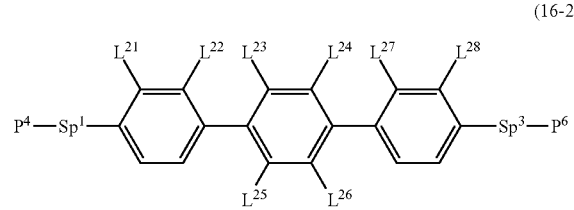

(16-3)

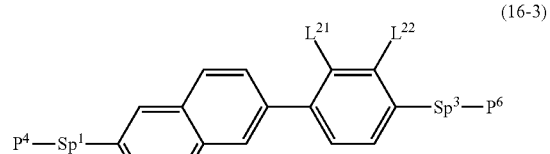

(16-4)

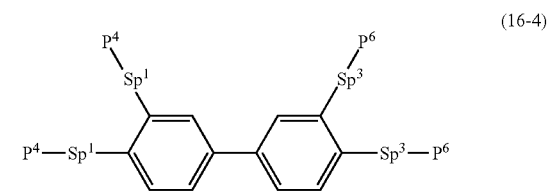

(16-5)

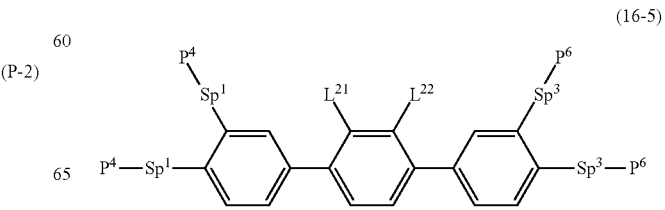

-continued (16-6)

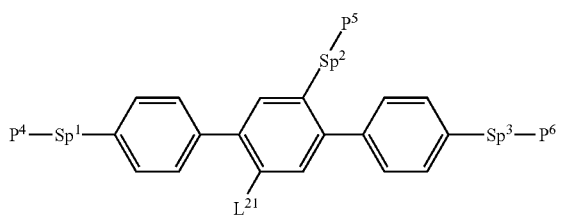

(16-7)

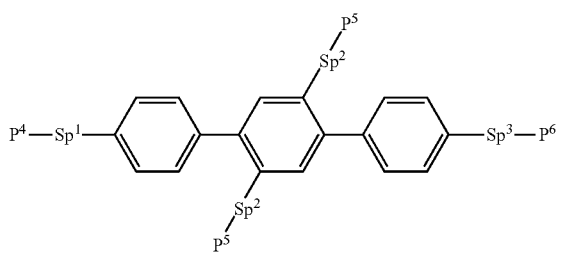

wherein, in formula (16-1) to formula (16-7), $P^4$, $P^5$ and $P^6$ are independently a polymerizable group selected from the group of groups represented by formula (P-1) to formula (P-3), and $M^1$, $M^2$ and $M^3$ are independently hydrogen, fluorine, alkyl having 1 to 5 carbons, or alkyl having 1 to 5 carbons in which at least one of hydrogen is replaced by halogen;

(P-1)

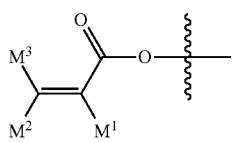

(P-2)

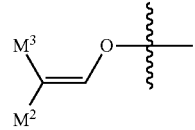

(P-3)

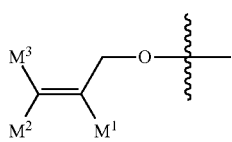

wherein, $L^{21}$, $L^{22}$, $L^{23}$, $L^{24}$, $L^{25}$, $L^{26}$, $L^{27}$ and $L^{28}$ are independently hydrogen, fluorine or methyl; $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, and at least one of —CH$_2$CH$_2$— may be replaced by —CH=CH— or —C≡C—, and in the groups, at least one of hydrogen may be replaced by fluorine or chlorine.

Item 18. The liquid crystal composition according to any one of items 10 to 17, further containing at least one of a polymerizable compound other than the compounds represented by formula (16), a polymerization initiator, a polymerization inhibitor, an optically active compound, an antioxidant, an ultraviolet light absorber, a light stabilizer, a heat stabilizer and an antifoaming agent.

Item 19. A liquid crystal display device, including at least one liquid crystal composition according to any one of items 10 to 18.

The invention further includes the following items: (a) the composition, further containing at least two of additives such as a polymerizable compound, a polymerization initiator, a polymerization inhibitor, an optically active compound, an antioxidant, an ultraviolet light absorber, a light stabilizer, a heat stabilizer and an antifoaming agent; (b) a polymerizable composition prepared by adding a polymerizable compound different from polymerizable compound (16) to the liquid crystal composition; (c) a polymerizable composition prepared by adding polar compound (1) and polymerizable compound (16) to the liquid crystal composition; (d) a liquid crystal composite prepared by polymerizing the polymerizable composition; (e) a polymer sustained alignment mode device including the liquid crystal composite; and (f) the polymer sustained alignment mode device, making by using the polymerizable composition which prepared by adding polar compound (1), polymerizable compound (16) and a polymerizable compound different from polymerizable compound (16) to the liquid crystal composition.

An aspect of compound (1), a synthesis method of compound (1), the liquid crystal composition and the liquid crystal display device will be described in the order.

1. Aspect of Compound (1)

Compound (1) of the invention has a feature of having a polar group such as hydroxy, amino and silyl, and difluoromethylene (—CF$_2$—). Compound (1) is useful because the polar group noncovalently interacts with a surface of a substrate of glass (or metal oxide). One of applications is an additive for a liquid crystal composition to be used in a liquid crystal display device. Compound (1) is added for the purpose of assisting alignment of the liquid crystal molecules. Such an additive is preferably chemically stable under conditions being sealed in the device, has a high solubility in the liquid crystal composition and causes no decrease of liquid crystallinity of the liquid crystal composition. Compound (1) satisfies such characteristics to a significant degree. See Comparative Example for the liquid crystallinity such as a maximum temperature.

Preferred examples of compound (1) will be described. Preferred examples of $R^1$, a, $R^2$, $S^1$, $S^2$, $S^3$, $S^4$ and $X^1$ in compound (1) apply also to a subordinate formula of formula (1) for compound (1). In compound (1), characteristics can be arbitrarily adjusted by suitably combining kinds of the groups. Compound (1) may contain a larger amount of isotope such as $^2$H (deuterium) and $^{13}$C than the amount of natural abundance because no significant difference exists in the characteristics of the compound.

(1)

(1a)

(1b)

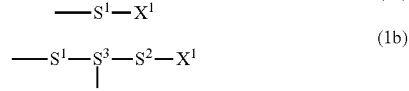

(1c)

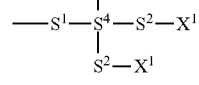

In formula (1), $R^1$ is alkyl having 3 to 15 carbons, alkyl having 2 to 15 carbons in which at least one of —$CH_2$— is replaced by —O—, or alkenyl having 4 to 15 carbons, and in the groups, at least one of hydrogen may be replaced by fluorine or chlorine.

Preferred $R^1$ is alkyl having 3 to 15 carbons, alkoxy having 2 to 14 carbons, alkoxyalkyl having 2 to 14 carbons or alkenyl having 4 to 15 carbons. Further preferred $R^1$ is alkyl having 3 to 15 carbons, alkoxy having 2 to 14 carbons or alkoxyalkyl having 2 to 14 carbons. Particularly preferred $R^1$ is alkyl having 3 to 15 carbons.

In formula (1), a is an integer from 2 to 12. Preferred a is an integer from 2 to 7.

In formula (1), $R^2$ is a group represented by formula (1a), formula (1b) or formula (1c). Preferred $R^2$ is a group represented by formula (1a) or formula (1b). Further preferred $R^2$ is a group represented by formula (1a).

In formula (1a) to formula (1c), $S^1$ and $S^2$ are independently a single bond or alkylene having 1 to 10 carbons, and in the alkylene, at least one of —$CH_2$— may be replaced by —O—, —NH—, —CO—, —COO—, —OCO— or —OCOO—, and at least one of —$(CH_2)_2$— may be replaced by —CH=CH—, and in the groups, at least one of hydrogen may be replaced by fluorine or chlorine.

Preferred $S^1$ or $S^2$ is a single bond or alkylene having 1 to 5 carbons, and in the alkylene, one of —$CH_2$— may be replaced by —O— or —NH—, one of —$(CH_2)_2$— may be replaced by —CH=CH—. Further preferred $S^1$ or $S^2$ is alkylene having 1 to 3 carbons.

In formula (1a) to formula (1c), $S^3$ is >CH— or >N—; and $S^4$ is >C< or >Si<. Preferred $S^3$ is >CH— or >N—, and preferred $S^4$ is >C<. $S^3$ is preferred to $S^4$.

In formula (1a) to formula (1c), $X^1$ is —OH, —$NH_2$ or a group represented by —$OR^3$, —$N(R^3)_2$ or —$Si(R^3)_3$, in which $R^3$ is hydrogen or alkyl having 1 to 10 carbons, and in the alkyl, at least one of —$CH_2$— may be replaced by —O—, and at least one of —$(CH_2)_2$— may be replaced by —CH=CH—, and in the groups, at least one of hydrogen may be replaced by fluorine or chlorine.

Preferred $X^1$ is —OH, —$NH_2$ or a group represented by —$Si(R^3)_3$, in which $R^3$ is alkyl having 1 to 5 carbons or alkoxy having 1 to 4 carbons. Further preferred $X^1$ is —OH, —$NH_2$, —$Si(CH_3)_3$, —$Si(C_2H_5)_3$, —$Si(OCH_3)_3$ or —$Si(OC_2H_5)_3$. Particularly preferred $X^1$ is —OH, —$Si(CH_3)_3$— $Si(C_2H_5)_3$—$Si(OCH_3)_3$ or —$Si(OC_2H_5)_3$. Most preferred $X^1$ is —OH.

The component compounds of the liquid crystal composition are shown in formula (2) to formula (15). Compounds (2) to (4) have a small dielectric anisotropy. Compounds (5) to (7) have a large positive dielectric anisotropy. Compound (8) has a cyano group, and therefore (8) has a larger positive dielectric anisotropy. Compounds (9) to (15) have a larger negative dielectric anisotropy. Specific examples of the compounds will be described later.

In compound (16), $P^1$, $P^2$ and $P^3$ are independently a polymerizable group. Preferred $P^1$, $P^2$ or $P^3$ is a polymerizable group selected from the group of groups represented by formula (P-1) to formula (P-5). Further preferred $P^1$, $P^2$ or $P^3$ is group (P-1) or group (P-2). Particularly preferred group (P-1) is —OCO—CH=$CH_2$ or —OCO—$C(CH_3)$=$CH_2$. A wavy line in group (P-1) to group (P-5) represents a site to form a bonding.

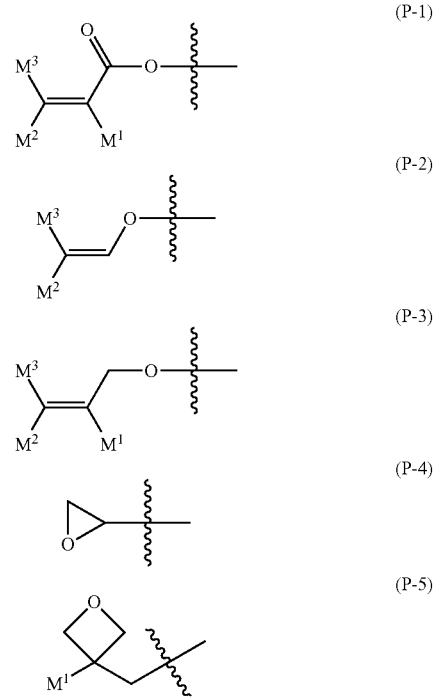

In group (P-1) to group (P-5), $M^1$, $M^2$ and $M^3$ are independently hydrogen, fluorine, alkyl having 1 to 5 carbons, or alkyl having 1 to 5 carbons in which at least one of hydrogen is replaced by halogen. Preferred $M^1$, $M^2$ or $M^3$ is hydrogen or methyl for increasing reactivity. Further preferred $M^1$ is methyl, and further preferred $M^2$ or $M^3$ is hydrogen.

In compound (16), $Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2$—$CH_2$— may be replaced by —CH=CH— or —C≡C—, and in the groups, at least one of hydrogen may be replaced by fluorine or chlorine. Preferred $Sp^1$, $Sp^2$ or $Sp^3$ is a single bond.

Ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen. Preferred ring F or ring I is phenyl. Ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen. Particularly preferred ring G is 1,4-phenylene or 2-fluoro-1,4-phenylene.

$Z^7$ and $Z^8$ are independently a single bond or alkylene having 1 to 10 carbons, and in the alkylene, at least one of —$CH_2$— may be replaced by —O—, —CO—, —COO— or —OCO—, and at least one of —CH₂—CH₂— may be replaced by —CH═CH—, —C(CH₃)═CH—, —CH═C(CH₃)— or —C(CH₃)═C(CH₃)—, and in the groups, at least one of hydrogen may be replaced by fluorine or chlorine. Preferred $Z^7$ or $Z^8$ is a single bond, —CH₂CH₂—, —CH₂O—, —OCH₂—, —COO— or —OCO—. Further preferred $Z^7$ or $Z^8$ is a single bond.

Then, d is 0, 1 or 2. Preferred d is 0 or 1. Then, e, f and g are independently 0, 1, 2, 3 or 4, and a sum of e, f and g is 1 or more. Preferred e, f or g is 1 or 2.

2. Synthesis of Compound (1)

The synthesis method of compound (1) will be described. Compound (1) can be prepared by suitably combining techniques in synthetic organic chemistry. Any compounds whose synthetic methods are not described can be prepared according to methods described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course" (Shin Jikken Kagaku Koza in Japanese) (Maruzen Co., Ltd.).

Compound (1) in which $R^2$ is a group represented by formula (1a), $S^1$ is alkylene having carbons larger than 2 and $X^1$ is —OH can be prepared by the method described below. Compound (53) is obtained by allowing compound (51) to react with compound (52) under conditions of radical generation of sodium dithionite and sodium hydrogencarbonate. Compound (55) is obtained by allowing the compound to react with compound (54) under conditions of radical generation. Compound (1) can be derived therefrom by reducing compound (55) using lithium aluminum hydride. In addition, a two-step reaction in which compound (55) is obtained from compound (51) can also be performed in one-pot.

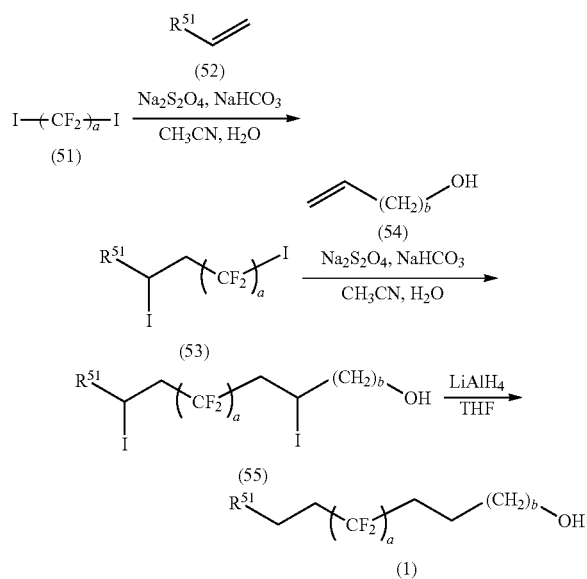

In the formulas, $R^{51}$ is alkyl having 1 to 13 carbons, a is an integer from 2 to 12, and b is an integer from 0 to 8.

Compound (1) in which $R^2$ is a group represented by formula (1a), $S^1$ is —CH₂— and $X^1$ is —OH can be prepared by the method described below. Compound (56) is obtained by allowing formaldehyde and methyl lithium to act on compound (53). Compound (1) can be derived therefrom by reducing compound (56) using lithium aluminum hydride.

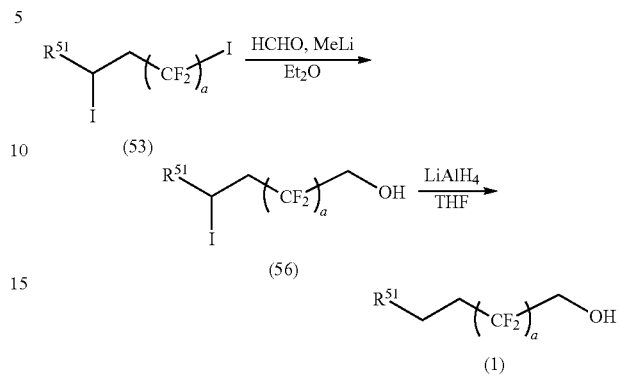

In the formulas, $R^{51}$ is alkyl having 1 to 13 carbons, and a is an integer from 2 to 12.

Compound (1) in which $R^1$ is alkoxy methyl having 2 to 14 carbons, $R^2$ is a group represented by formula (1a), $S^1$ is —CH₂— and $X^1$ is —OH can be prepared by the method described below. Compound (1) can be derived therefrom by allowing compound (57) to react with sodium hydride, and further to react with alkyl tosylate (58).

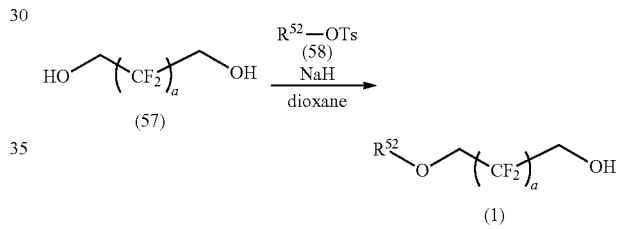

In the formulas, $R^{52}$ is alkyl having 1 to 13 carbons, and a is an integer from 2 to 12.

3. Liquid Crystal Composition

The liquid crystal composition of the invention contains compound (1) as component A. Compound (1) can assist alignment of the liquid crystal molecules by noncovalent interaction with a substrate of a device. The composition preferably contains compound (1) as component A, and further preferably contains a liquid crystal compound selected from components B, C, D and E shown below. Component B includes compounds (2) to (4). Component C includes compounds (5) to (7). Component D is compound (8). Component E includes compounds (9) to (15). The composition may also contain any other liquid crystal compound different from compounds (2) to (15). Upon preparing the composition, components B, C, D and E are preferably selected in consideration of magnitude of positive or negative dielectric anisotropy, or the like. The composition in which the component is suitably selected has a high maximum temperature, a low minimum temperature, a small viscosity, a suitable optical anisotropy (more specifically, large optical anisotropy or small optical anisotropy), a large positive or negative dielectric anisotropy, a large specific resistance, stability to heat or ultraviolet light, and a suitable elastic constant (more specifically, large elastic constant or small elastic constant).

A preferred ratio of compound (1) is approximately 0.01% by weight or more for maintaining a high stability to ultraviolet light, and approximately 5% by weight or less for dissolving in the liquid crystal composition. A further preferred ratio is in the range of approximately 0.05% by weight to approximately 2% by weight. A most preferred ratio is in the range of approximately 0.05% by weight to approximately 1% by weight.

Component B is a compound in which two terminal groups are alkyl or the like. Specific preferred examples of component B include compounds (2-1) to (2-11), compounds (3-1) to (3-19) and compounds (4-1) to (4-7). In the compounds of component B, $R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine.

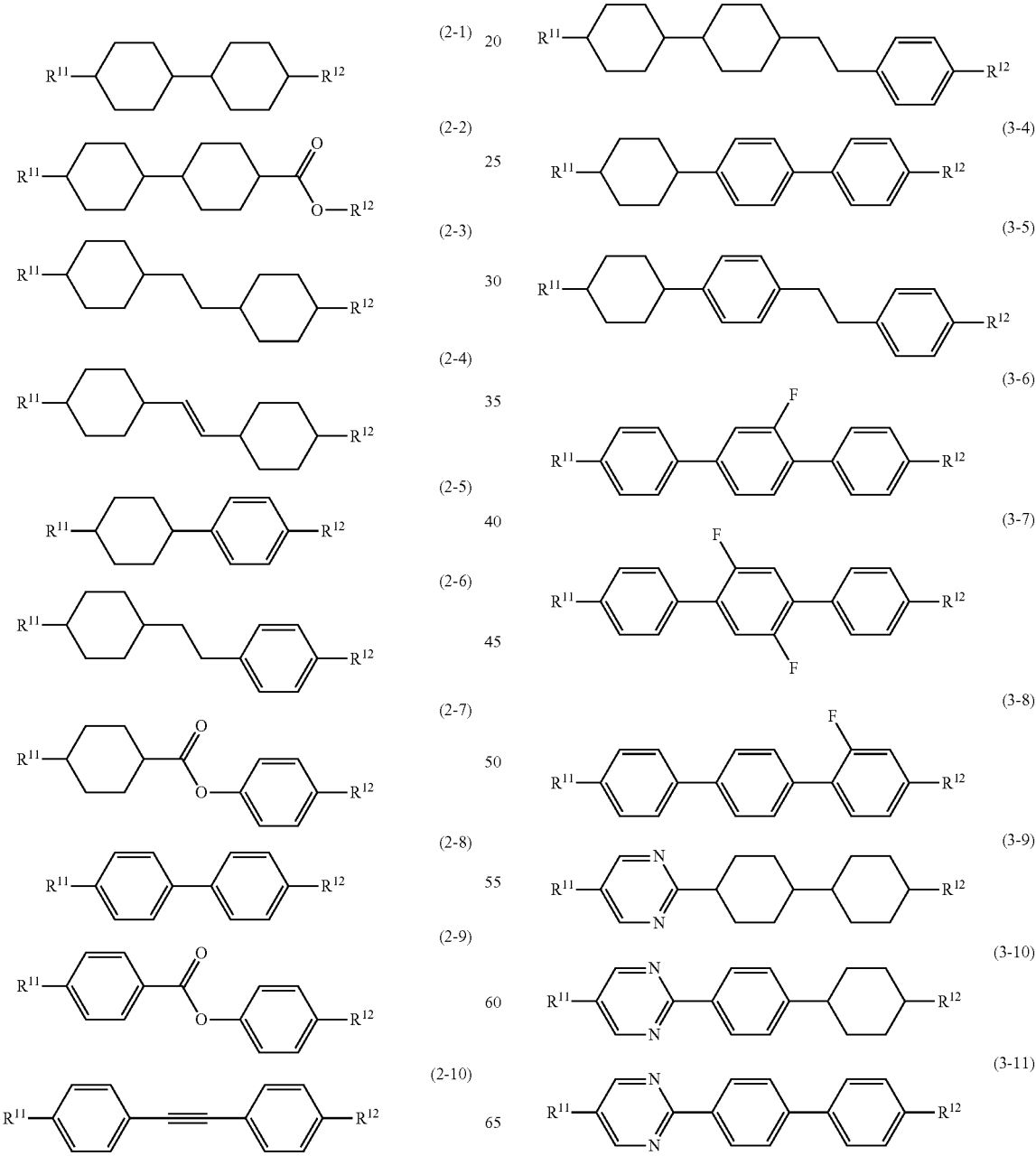

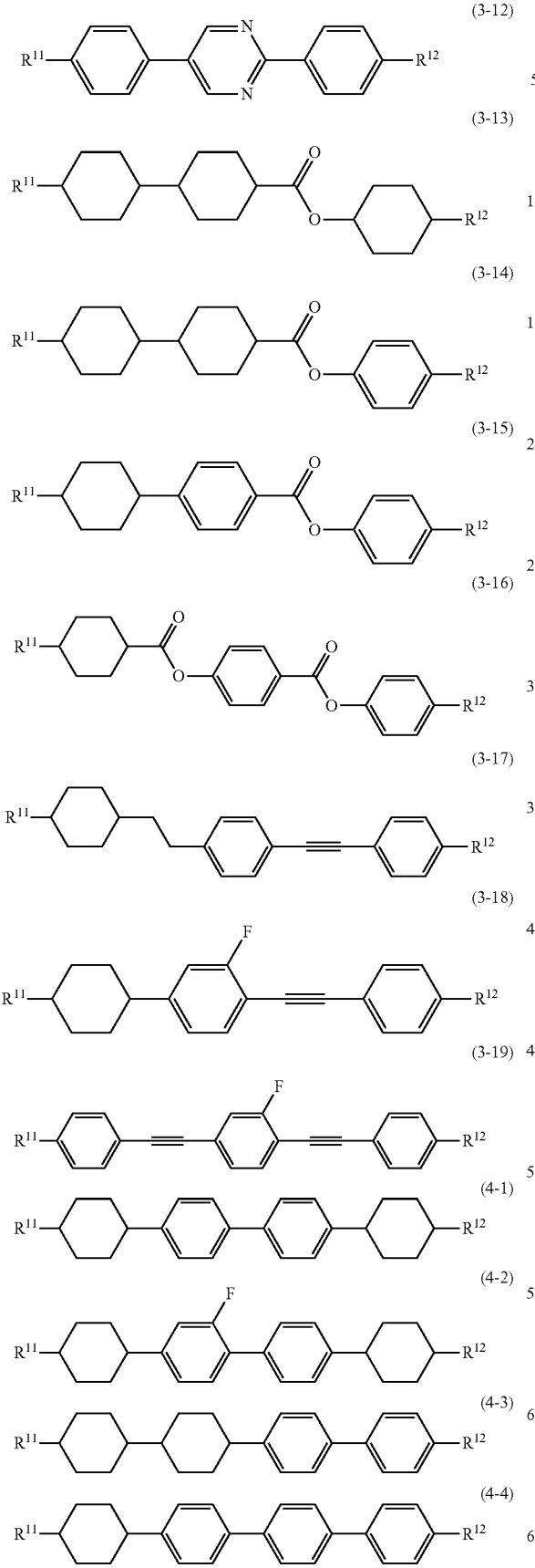

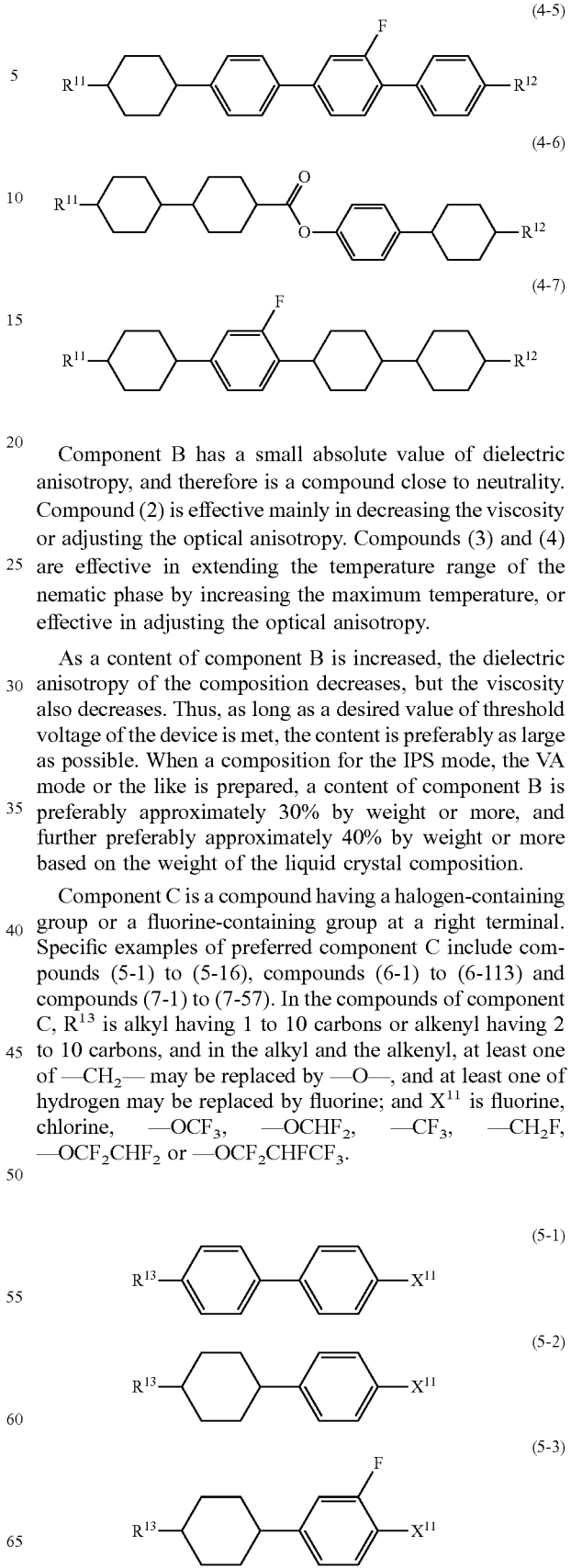

Component B has a small absolute value of dielectric anisotropy, and therefore is a compound close to neutrality. Compound (2) is effective mainly in decreasing the viscosity or adjusting the optical anisotropy. Compounds (3) and (4) are effective in extending the temperature range of the nematic phase by increasing the maximum temperature, or effective in adjusting the optical anisotropy.

As a content of component B is increased, the dielectric anisotropy of the composition decreases, but the viscosity also decreases. Thus, as long as a desired value of threshold voltage of the device is met, the content is preferably as large as possible. When a composition for the IPS mode, the VA mode or the like is prepared, a content of component B is preferably approximately 30% by weight or more, and further preferably approximately 40% by weight or more based on the weight of the liquid crystal composition.

Component C is a compound having a halogen-containing group or a fluorine-containing group at a right terminal. Specific examples of preferred component C include compounds (5-1) to (5-16), compounds (6-1) to (6-113) and compounds (7-1) to (7-57). In the compounds of component C, $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine; and $X^{11}$ is fluorine, chlorine, —$OCF_3$, —$OCHF_2$, —$CF_3$, —$CH_2F$, —$OCF_2CHF_2$ or —$OCF_2CHFCF_3$.

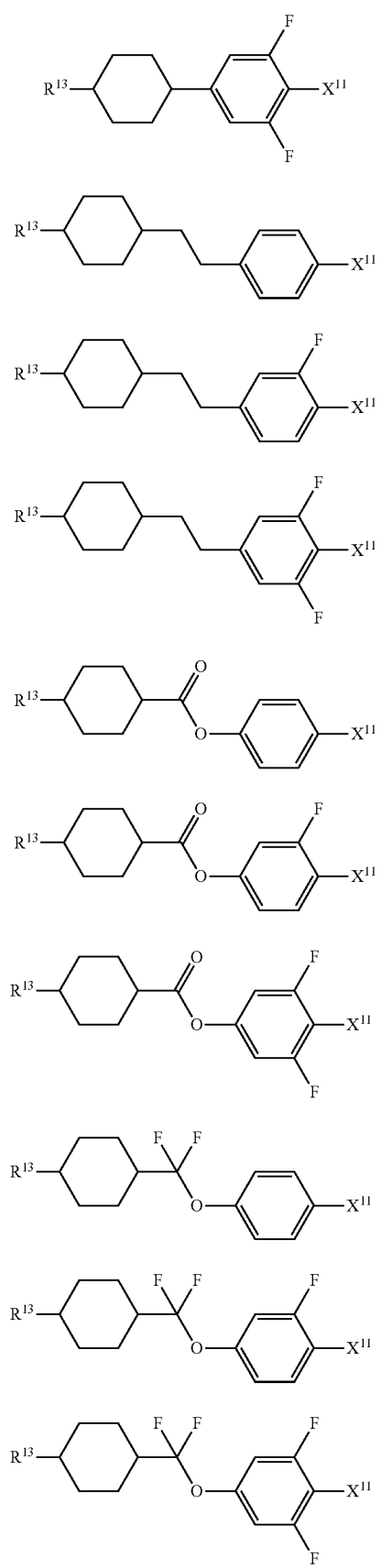
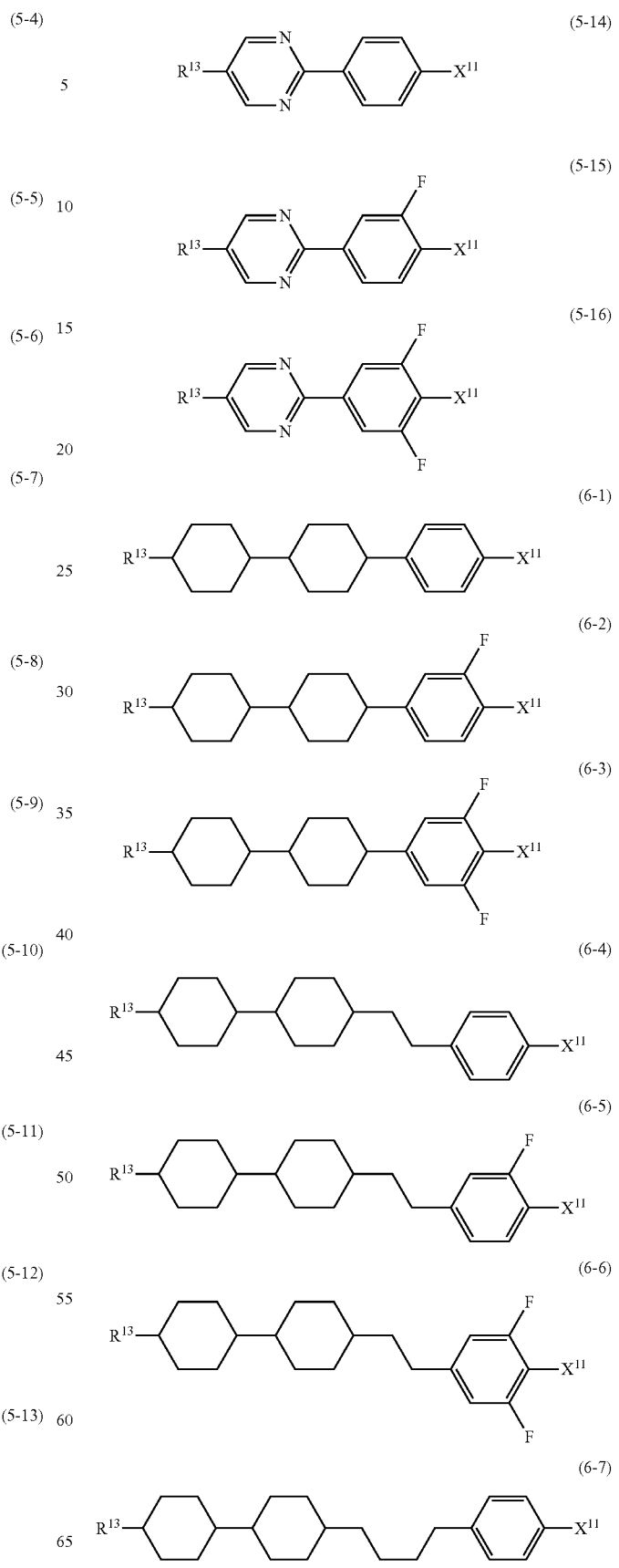

(6-8)
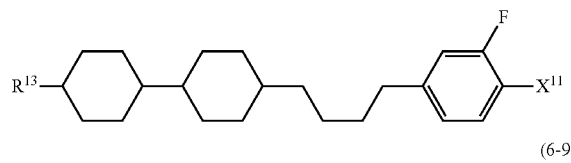
(6-9)
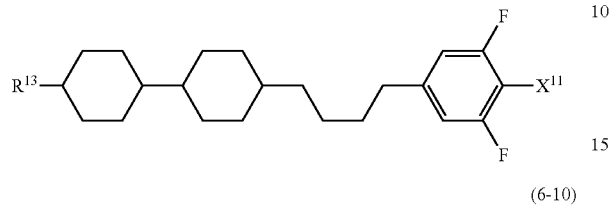
(6-10)
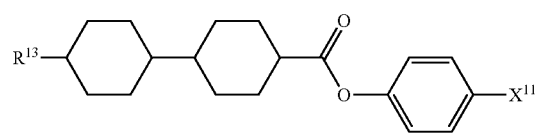
(6-11)
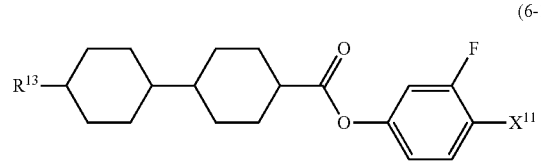
(6-12)
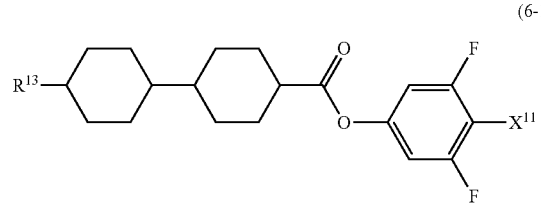
(6-13)
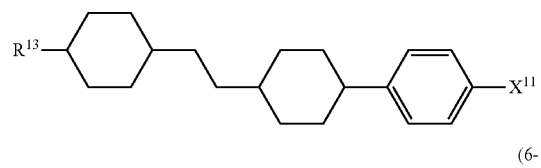
(6-14)
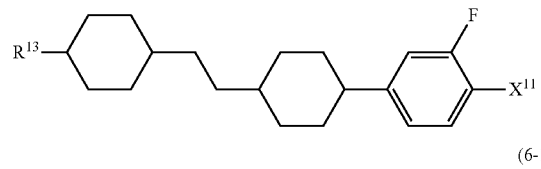
(6-15)
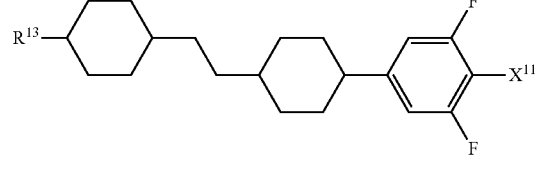
(6-16)
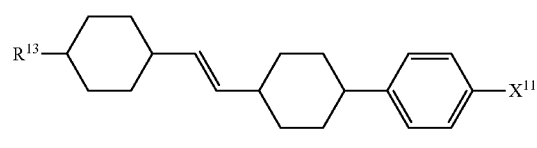
(6-17)
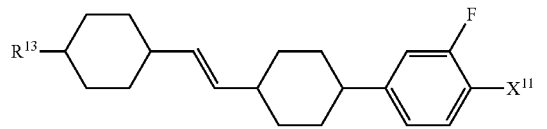
(6-18)
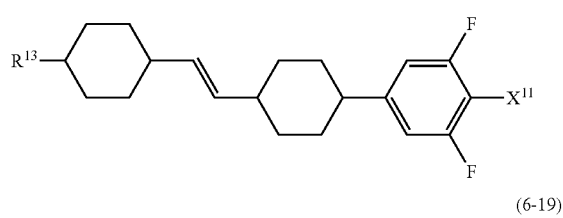
(6-19)
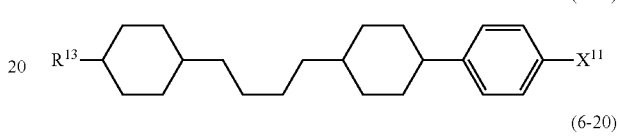
(6-20)
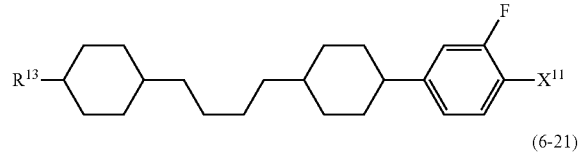
(6-21)
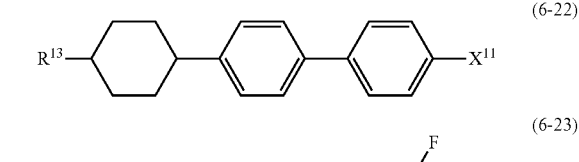
(6-22)
(6-23)
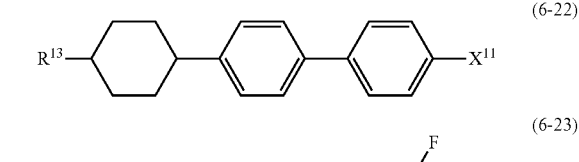
(6-24)
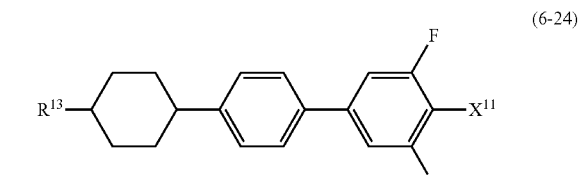
(6-25)
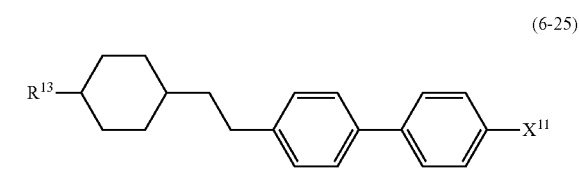
(6-26)
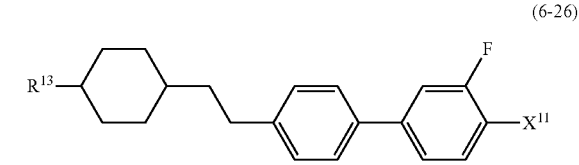

(6-27) 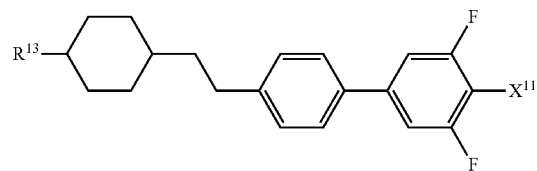
(6-28) 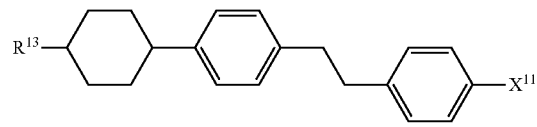
(6-29) 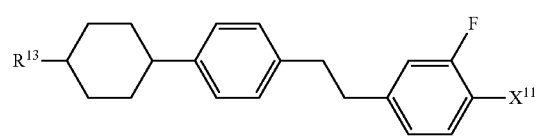
(6-30) 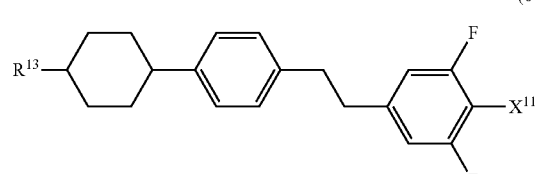
(6-31) 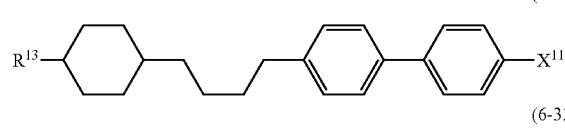
(6-32) 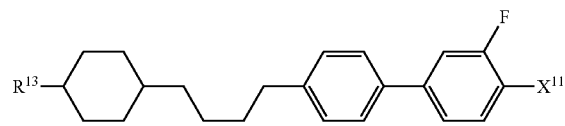
(6-33) 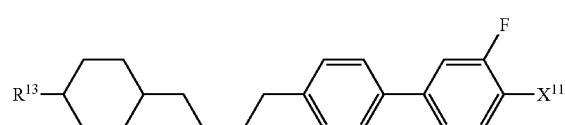
(6-34) 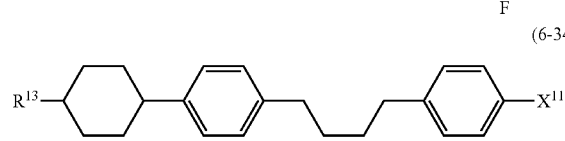
(6-35) 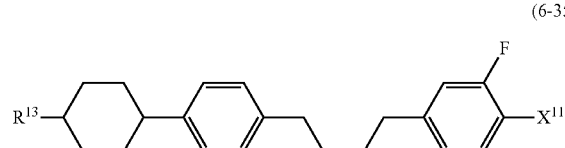
(6-36) 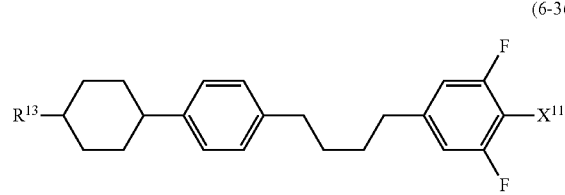
(6-37) 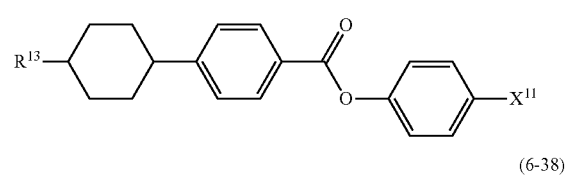
(6-38) 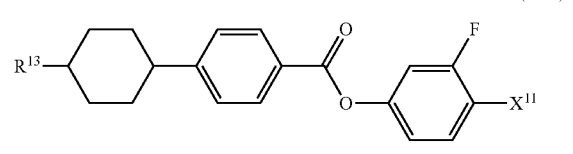
(6-39) 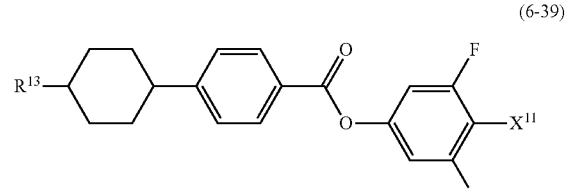
(6-40) 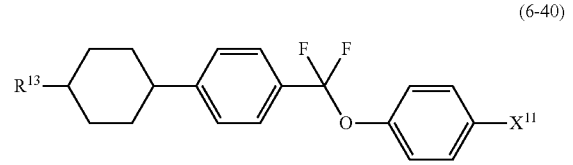
(6-41) 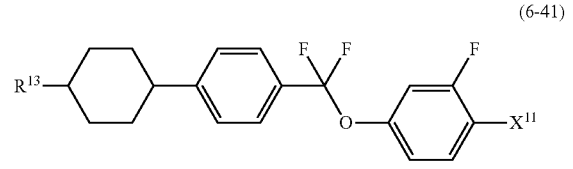
(6-42) 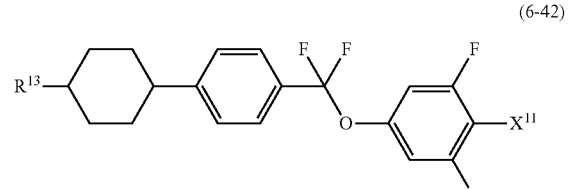
(6-43) 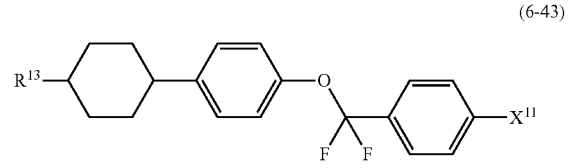
(6-44) 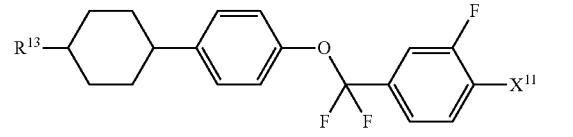
(6-45) 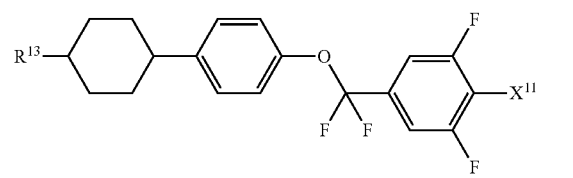

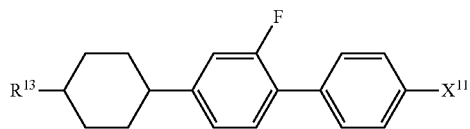
(6-46)
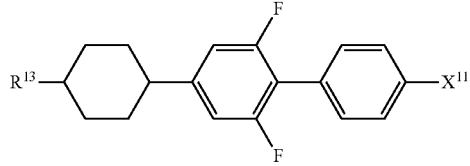
(6-47)
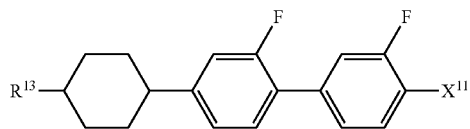
(6-48)
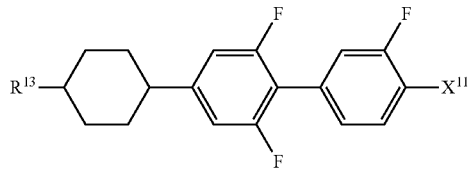
(6-49)
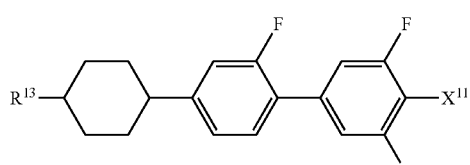
(6-50)
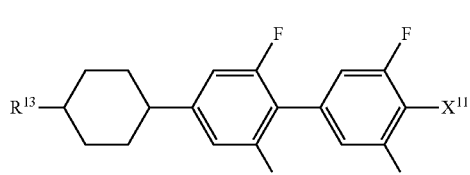
(6-51)
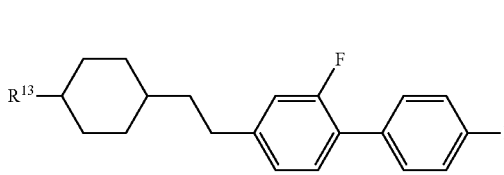
(6-52)
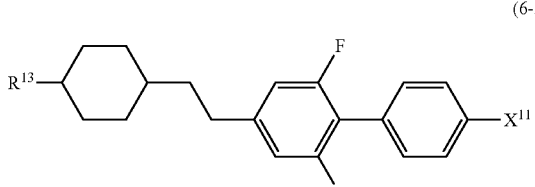
(6-53)
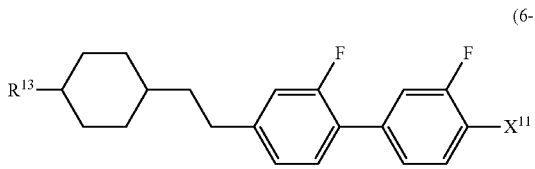
(6-54)
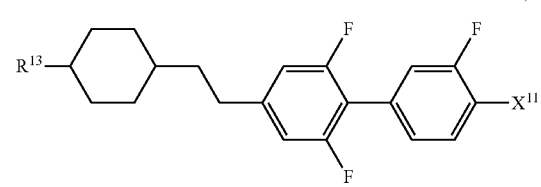
(6-55)
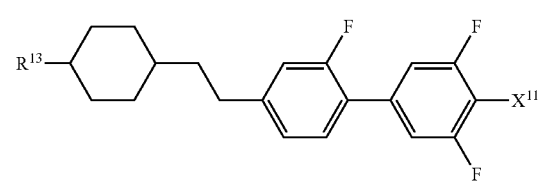
(6-56)
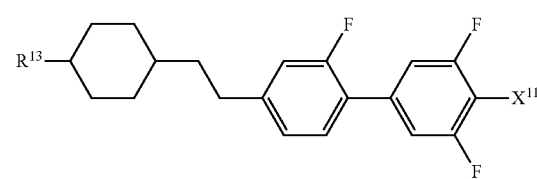
(6-57)
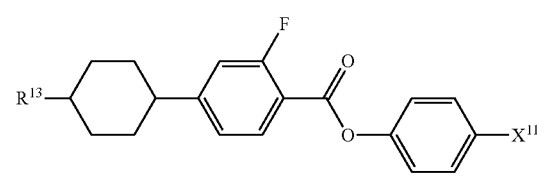
(6-58)
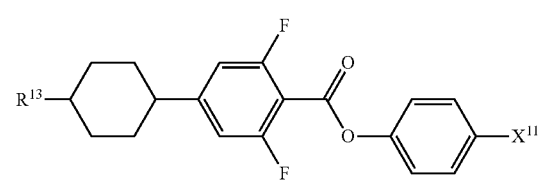
(6-59)
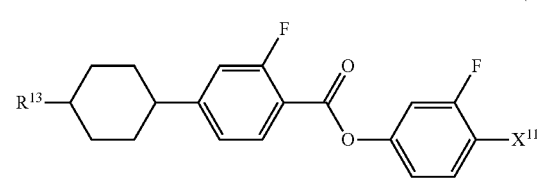
(6-60)
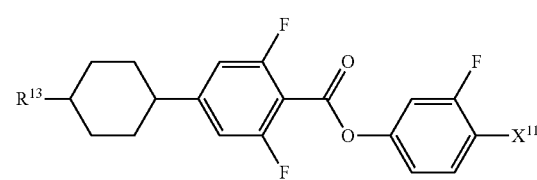
(6-61)
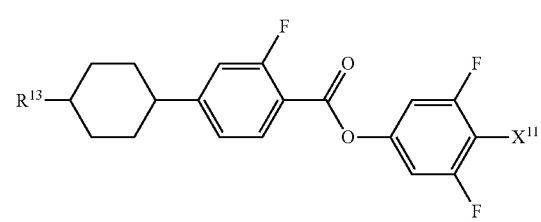
(6-62)

(6-63) 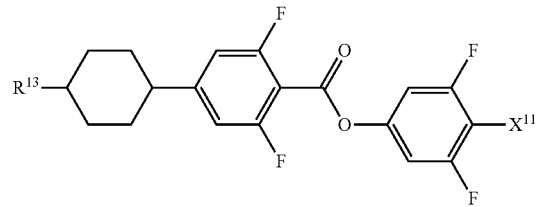
(6-64) 
(6-65) 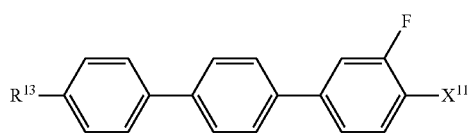
(6-66) 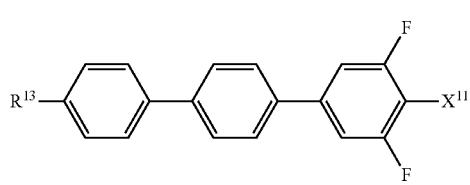
(6-67) 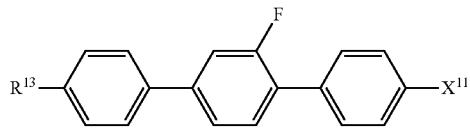
(6-68) 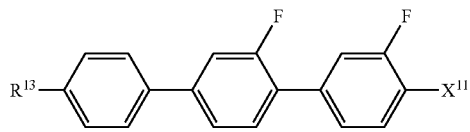
(6-69) 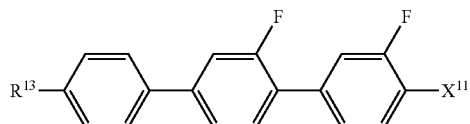
(6-70) 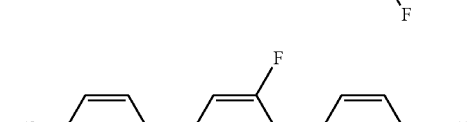
(6-71) 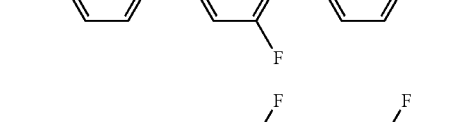
(6-72) 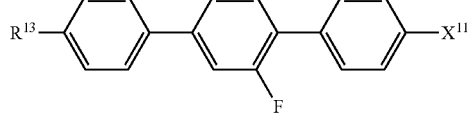
(6-73) 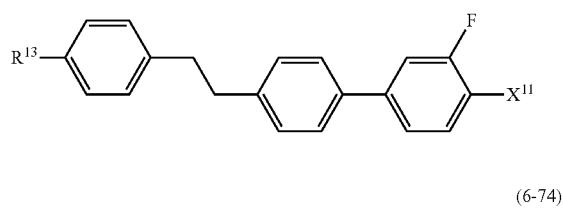
(6-74) 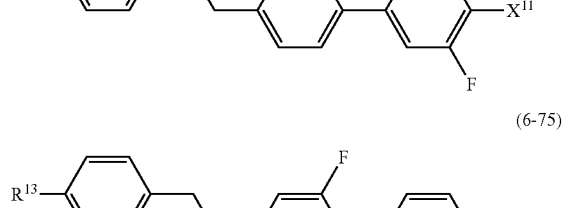
(6-75) 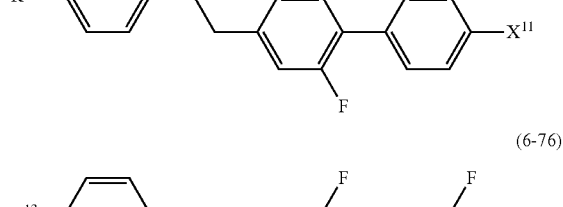
(6-76) 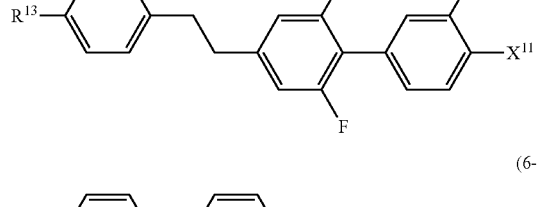
(6-77) 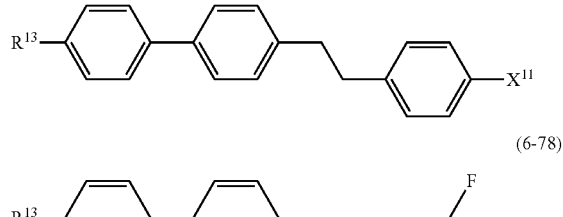
(6-78) 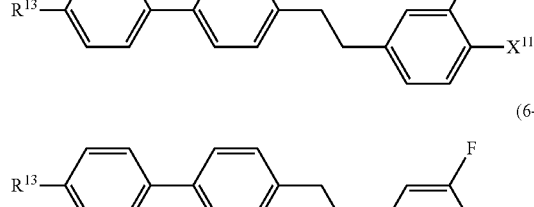
(6-79) 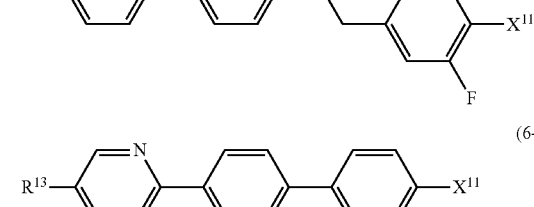
(6-80) 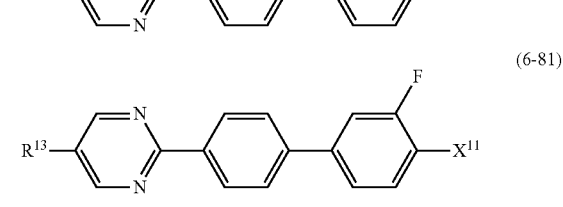
(6-81) 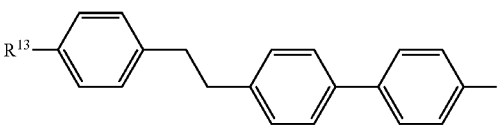

-continued
(6-82) 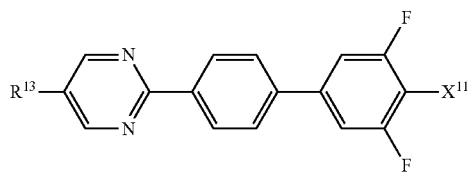
(6-83) 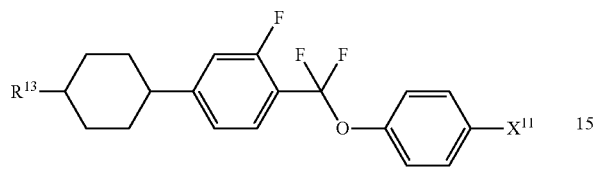
(6-84) 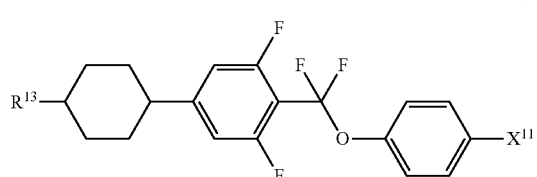
(6-85) 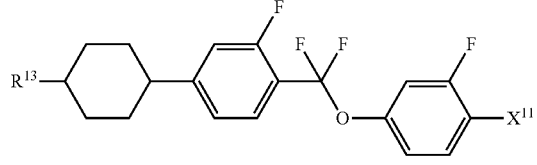
(6-86) 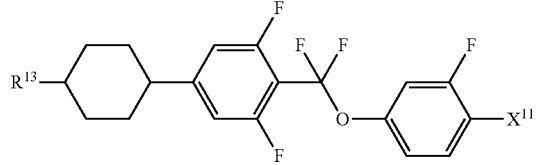
(6-87) 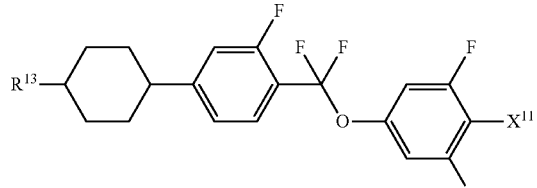
(6-88) 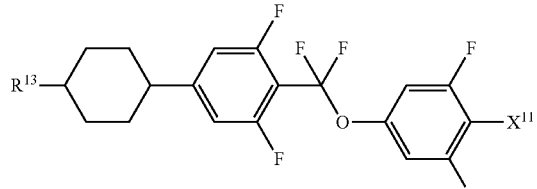
(6-89) 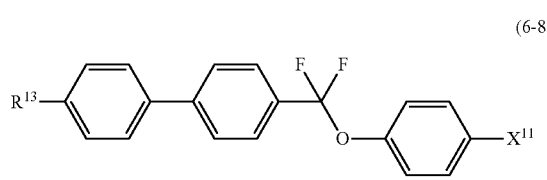
-continued
(6-90) 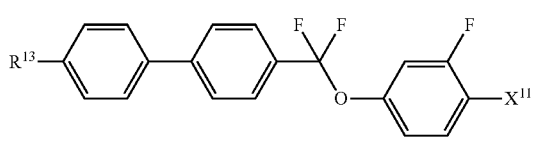
(6-91) 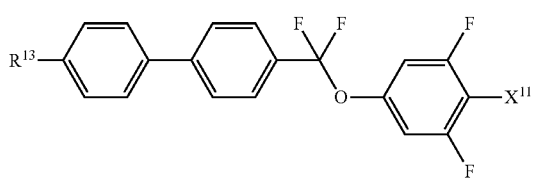
(6-92) 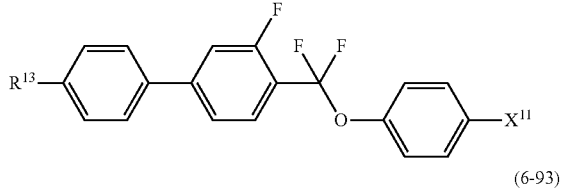
(6-93) 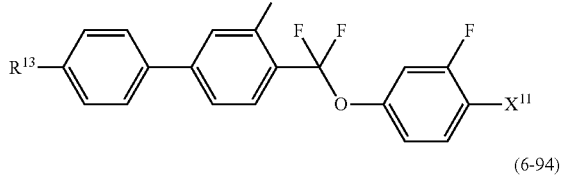
(6-94) 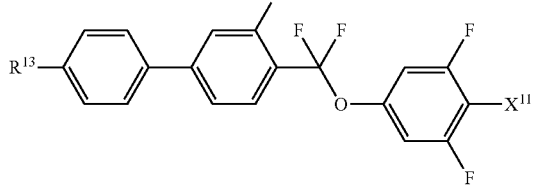
(6-95) 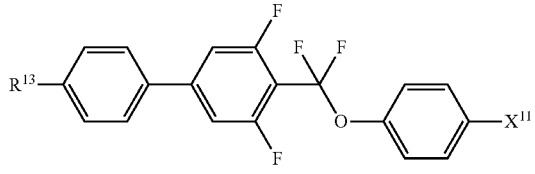
(6-96) 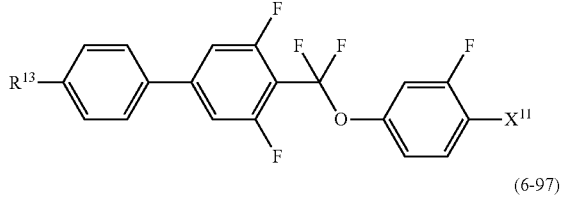
(6-97) 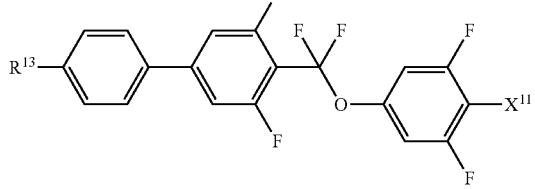

(6-98) 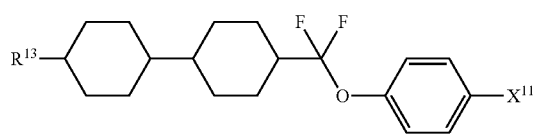
(6-99) 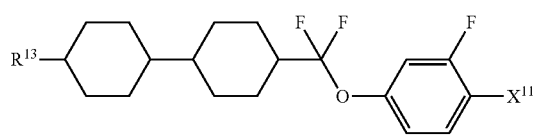
(6-100) 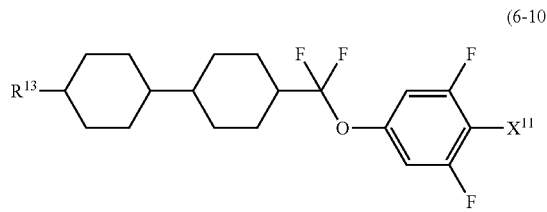
(6-101) 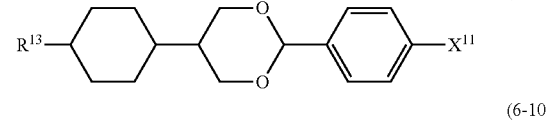
(6-102) 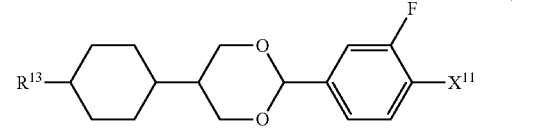
(6-103) 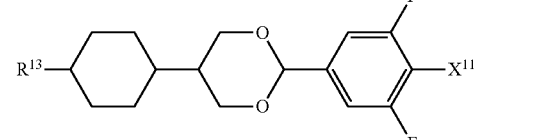
(6-104) 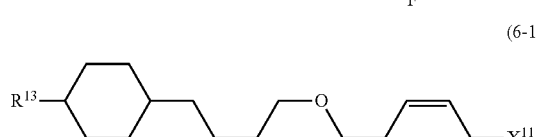
(6-105) 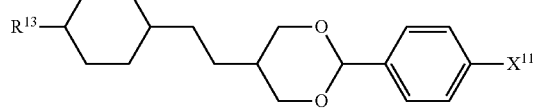
(6-106) 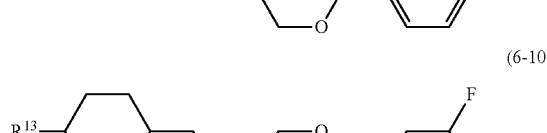
(6-107) 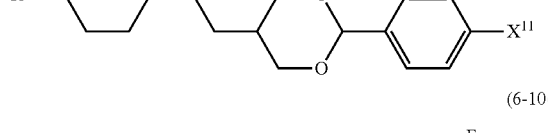
(6-108) 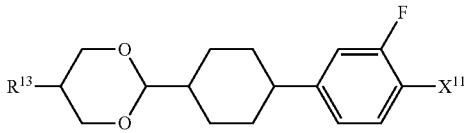
(6-109) 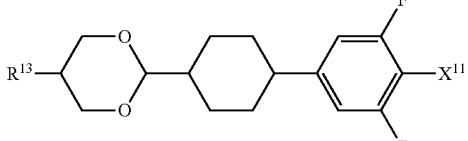
(6-110) 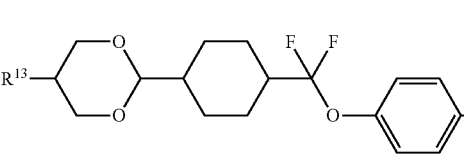
(6-111) 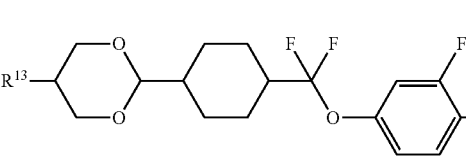
(6-112) 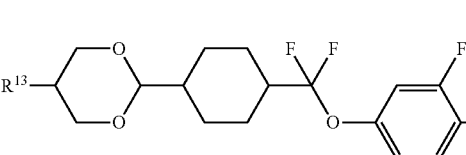
(6-113) 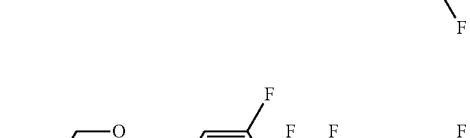
(7-1) 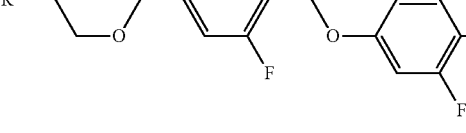
(7-2) 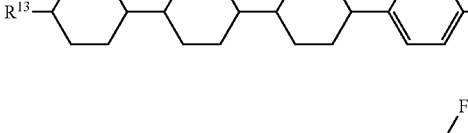
(7-3) 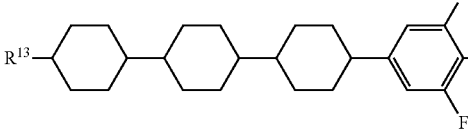
(7-4) 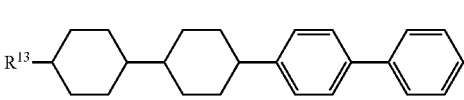

(7-5)
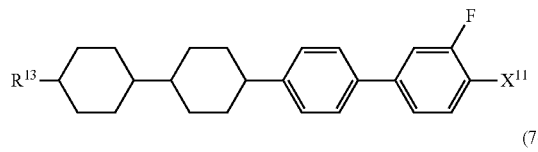
(7-6)
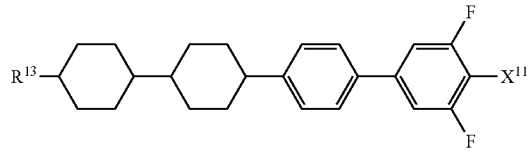
(7-7)
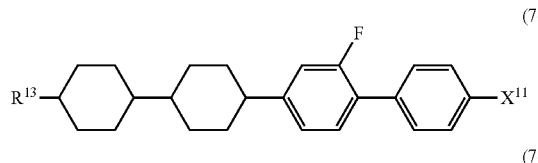
(7-8)
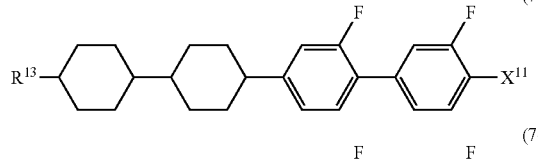
(7-9)
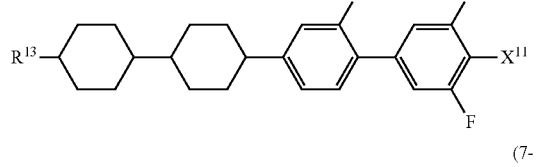
(7-10)
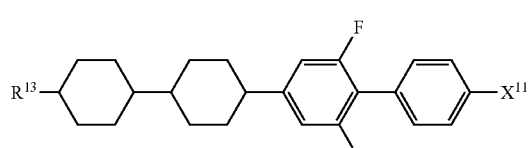
(7-11)
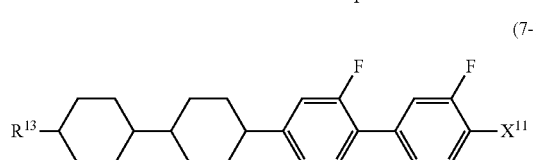
(7-12)
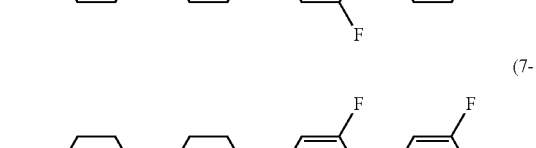
(7-13)
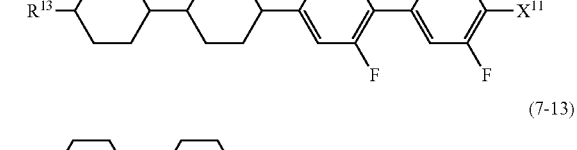
(7-14)
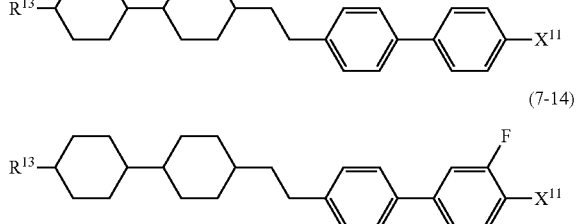
(7-15)
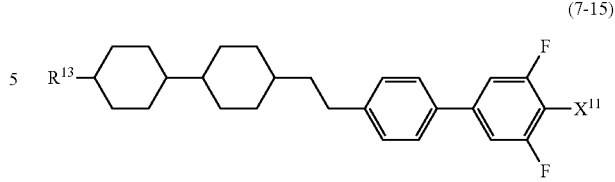
(7-16)
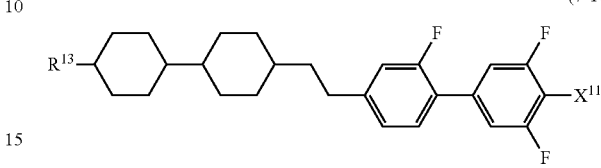
(7-17)
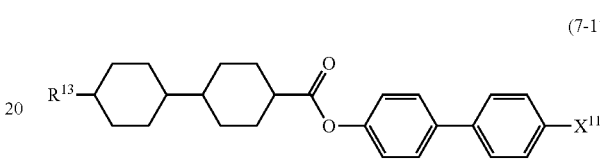
(7-18)
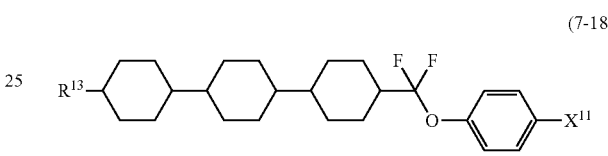
(7-19)
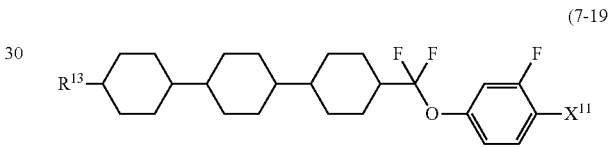
(7-20)
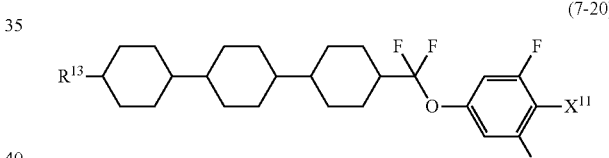
(7-21)
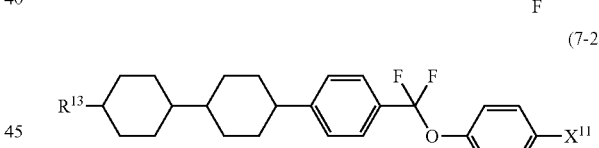
(7-22)
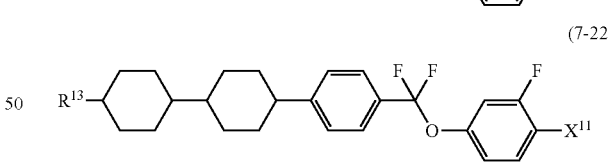
(7-23)
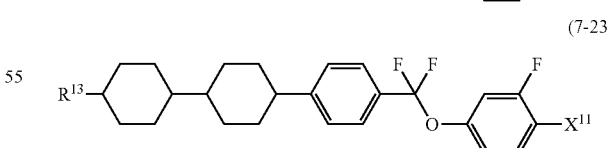
(7-24)
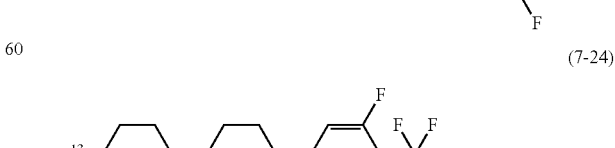

(7-25) 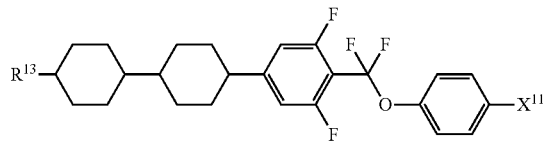
(7-26) 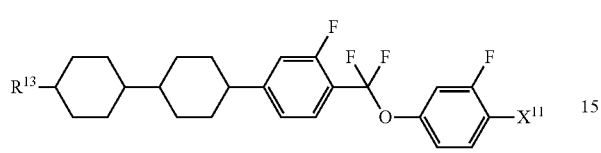
(7-27) 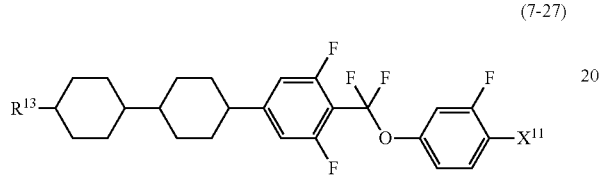
(7-28) 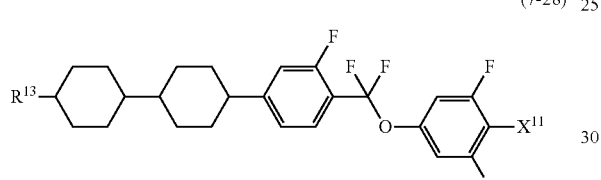
(7-29) 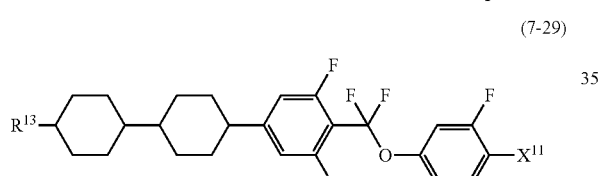
(7-30) 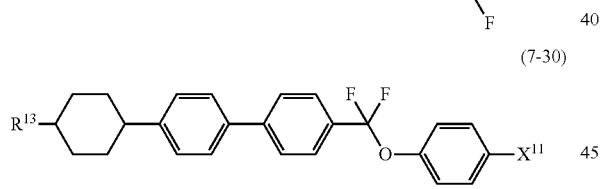
(7-31) 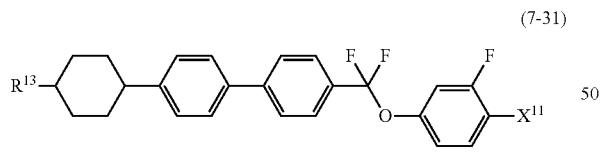
(7-32) 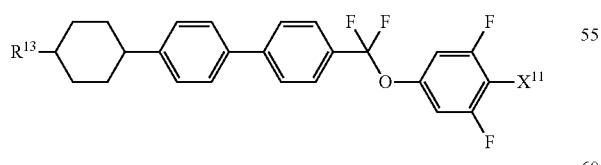
(7-33) 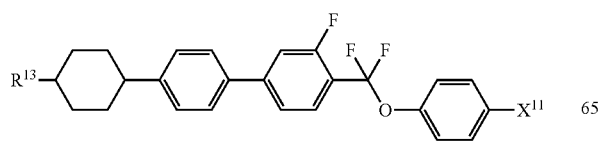
(7-34) 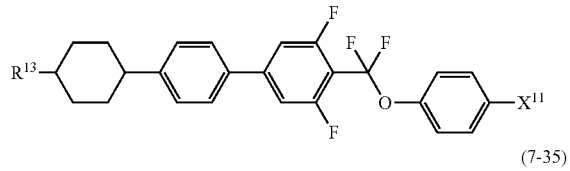
(7-35) 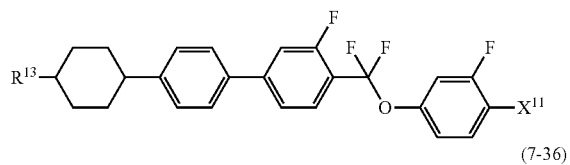
(7-36) 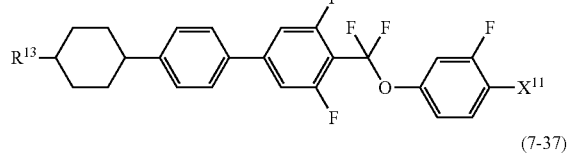
(7-37) 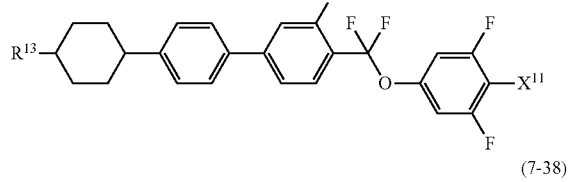
(7-38) 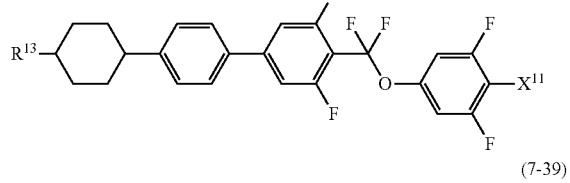
(7-39) 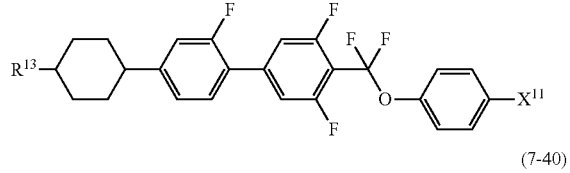
(7-40) 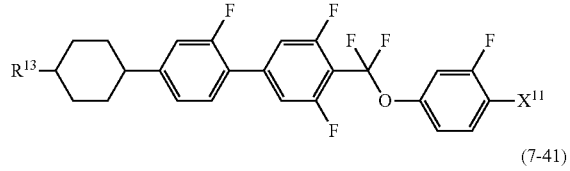
(7-41) 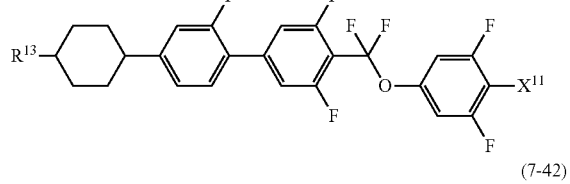
(7-42) 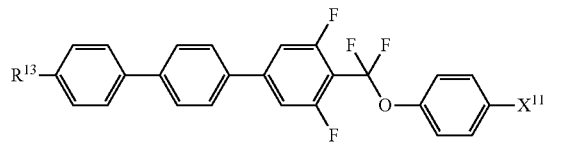

(7-43)
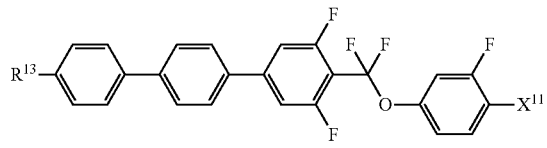

(7-44)
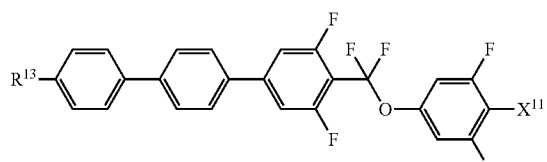

(7-45)
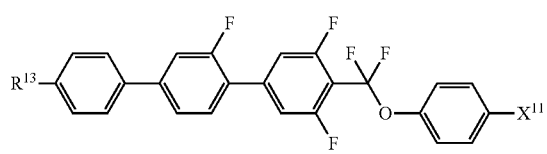

(7-46)
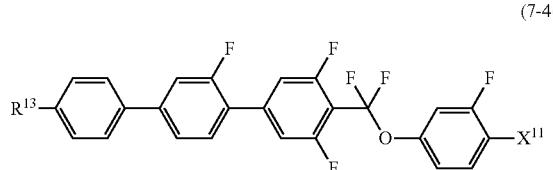

(7-47)
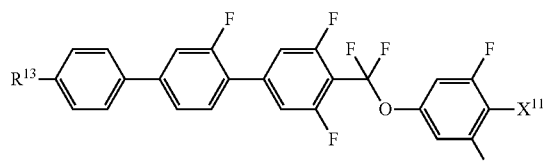

(7-48)
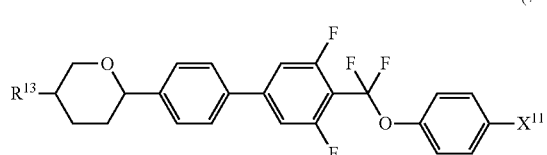

(7-49)
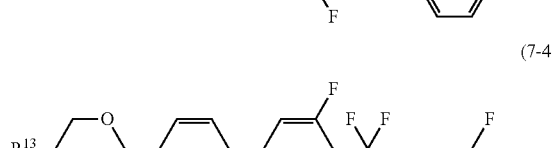

(7-50)
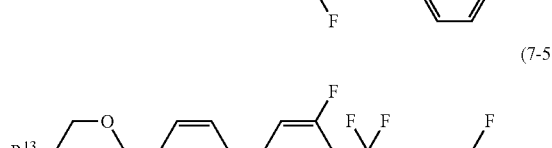

(7-51)
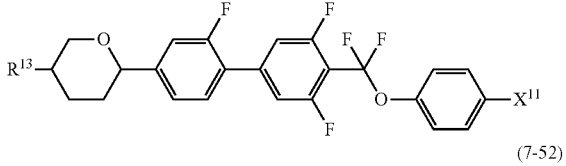

(7-52)
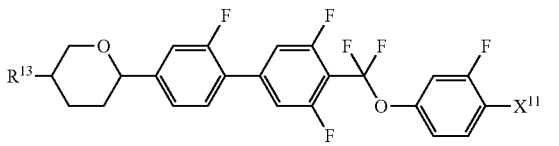

(7-53)
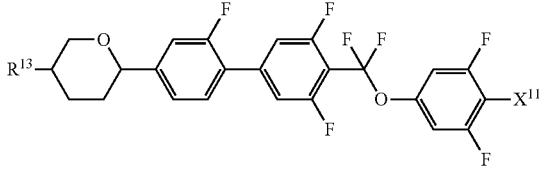

(7-54)
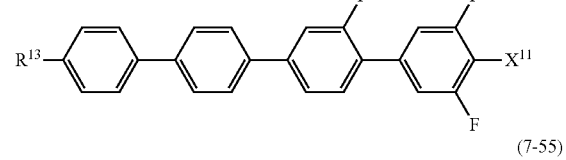

(7-55)
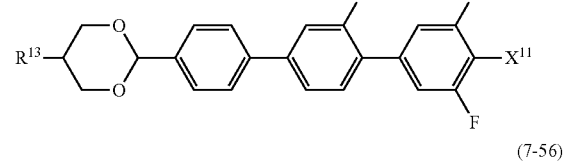

(7-56)
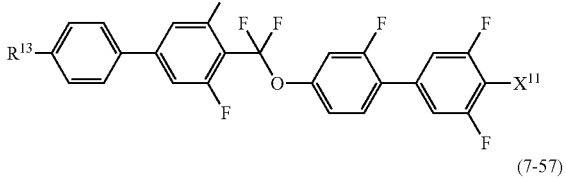

(7-57)
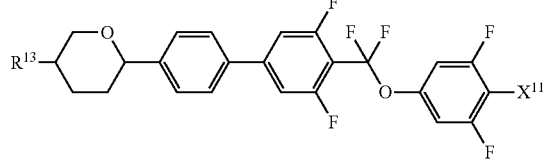

Component C has the positive dielectric anisotropy and a superb stability to heat, light or the like, and therefore are used for preparing a composition for the mode such as the IPS mode, the FFS mode and the OCB mode. A content of component C is suitably in the range of approximately 1% by weight to approximately 99% by weight, preferably in the range of approximately 10% by weight to approximately 97% by weight, and further preferably in the range of approximately 40% by weight to approximately 95% by weight, based on the weight of the liquid crystal composition. When component C is added to a composition having the negative dielectric anisotropy, a content of component C is preferably approximately 30% by weight or less based on the weight of the liquid crystal composition. When component C is added thereto, an elastic constant of the composition and a voltage-transmittance curve of the device can be adjusted.

Component D is compound (8) in which a right terminal group is —C≡N or —C≡C—C≡N. Specific examples of preferred component D include compounds (8-1) to (8-64). In the compounds of component D, $R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine; and $X^{12}$ is —C≡N or —C≡C—C≡N.

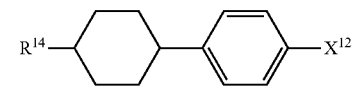
(8-1)

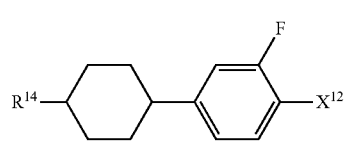
(8-2)

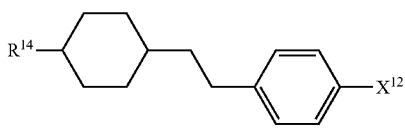
(8-3)

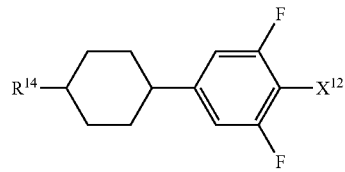
(8-4)

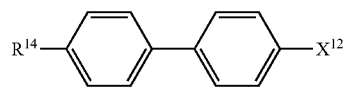
(8-5)

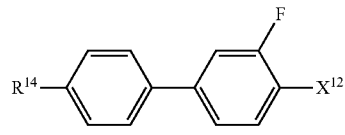
(8-6)

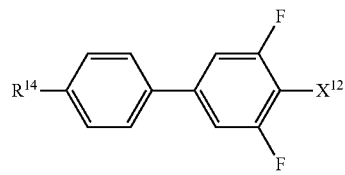
(8-7)

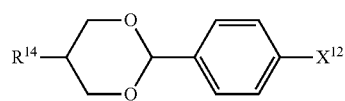
(8-8)

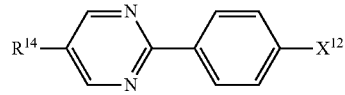
(8-9)

-continued

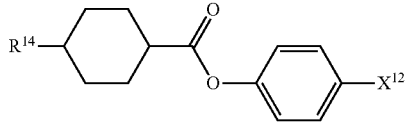
(8-10)

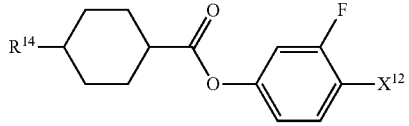
(8-11)

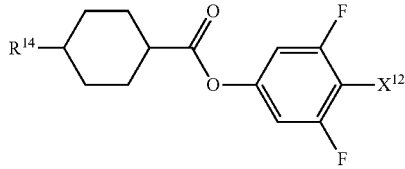
(8-12)

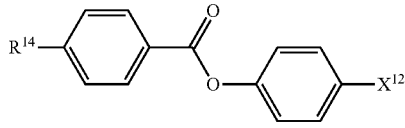
(8-13)

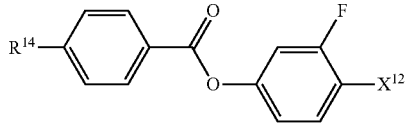
(8-14)

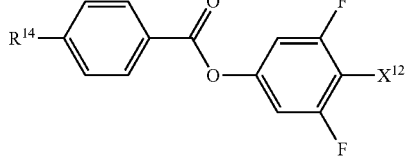
(8-15)

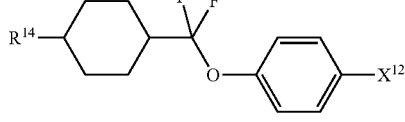
(8-16)

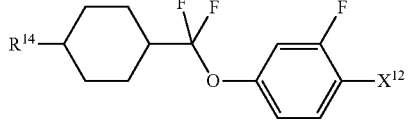
(8-17)

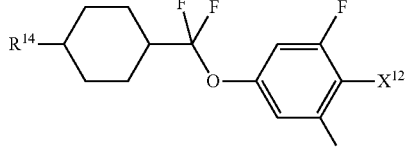
(8-18)

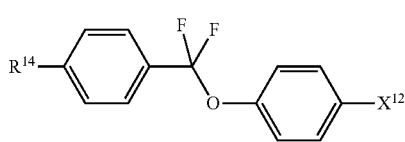
(8-19)

(8-20) 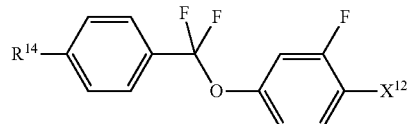
(8-21) 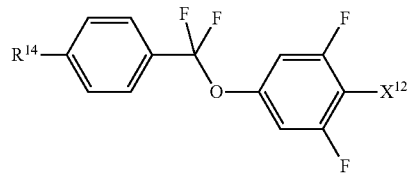
(8-22) 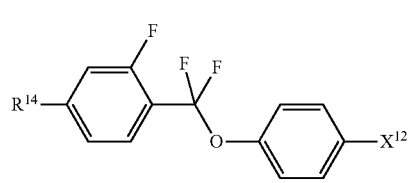
(8-23) 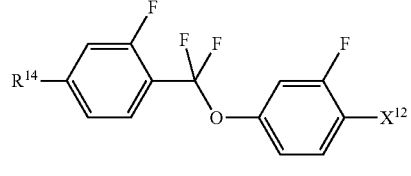
(8-24) 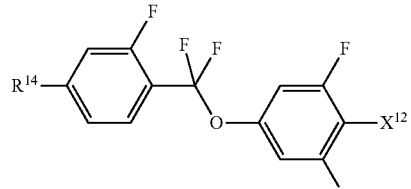
(8-25) 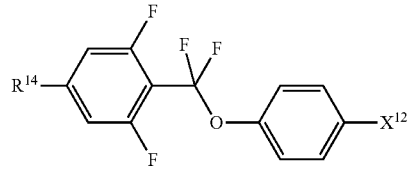
(8-26) 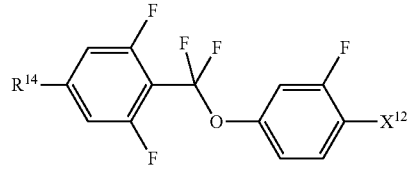
(8-27) 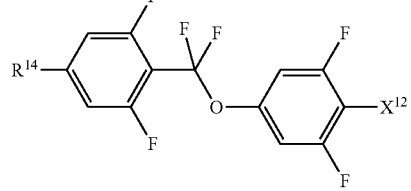
(8-28) 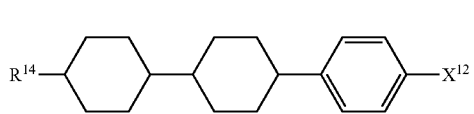
(8-29) 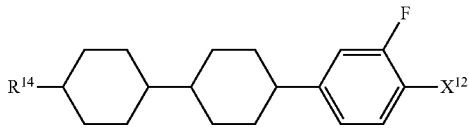
(8-30) 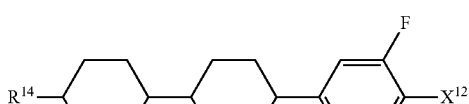
(8-31) 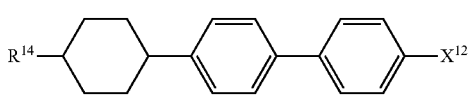
(8-32) 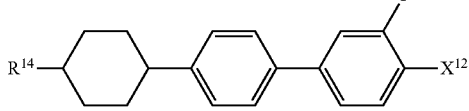
(8-33) 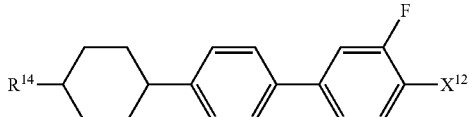
(8-34) 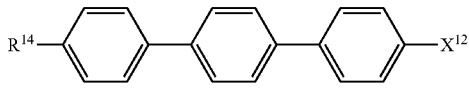
(8-35) 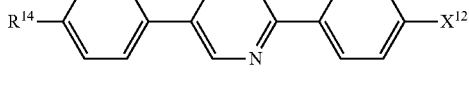
(8-36) 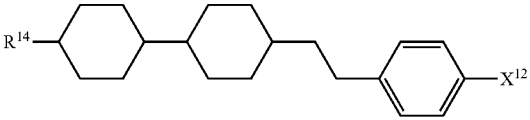
(8-37) 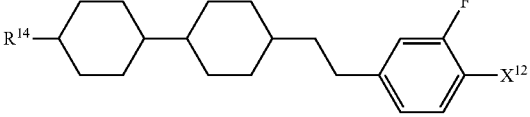
(8-38) 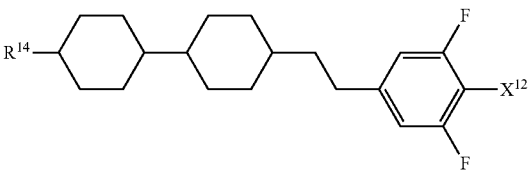

(8-39) (8-40) (8-41) (8-42) (8-43) (8-44) (8-45) (8-46) (8-47) (8-48) (8-49) (8-50) (8-51) (8-52) (8-53) (8-54) (8-55) (8-56)

-continued

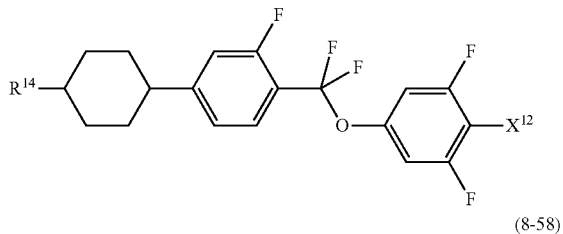
(8-57)

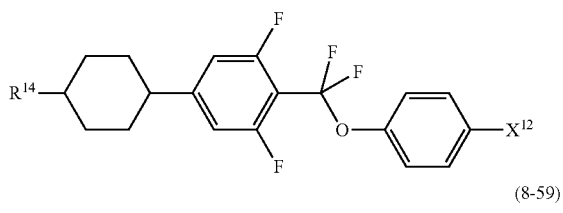
(8-58)

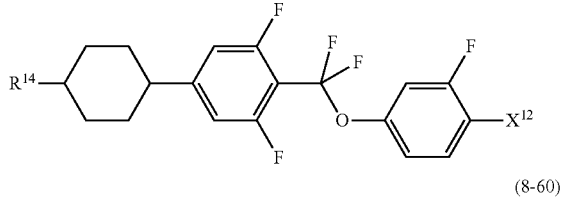
(8-59)

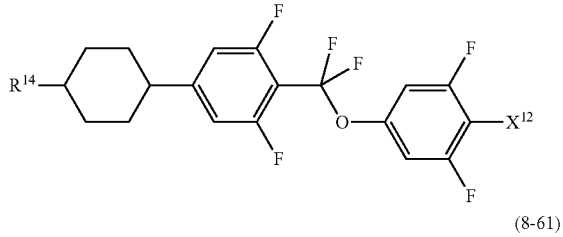
(8-60)

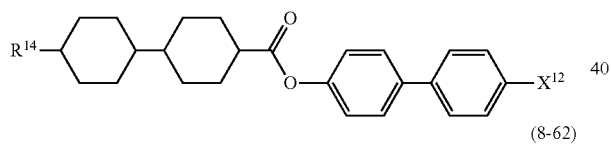
(8-61)

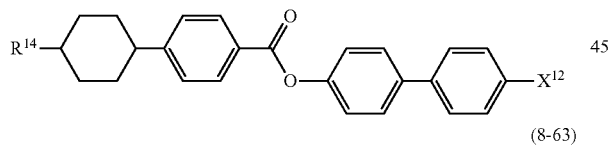
(8-62)

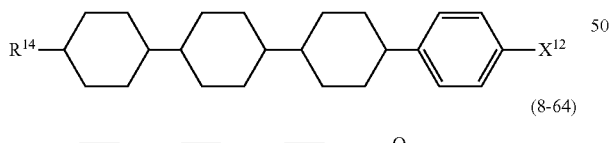
(8-63)

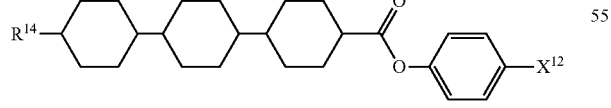
(8-64)

Component D has the positive dielectric anisotropy a value of which is large, and therefore is mainly used for preparing a composition for the mode such as the TN mode or the like. The dielectric anisotropy of the composition can be increased by adding component D thereto. Component D is effective in extending the temperature range of the liquid crystal phase, adjusting the viscosity or adjusting the optical anisotropy. Component D is also useful for adjusting the voltage-transmittance curve of the device.

When a composition for the TN mode or the like is prepared, a content of component D is suitably in the range of approximately 1% by weight to approximately 99% by weight, preferably in the range of approximately 10% by weight to approximately 97% by weight, and further preferably in the range of approximately 40% by weight to approximately 95% by weight based on the weight of the liquid crystal composition. When component D is added to the composition having the negative dielectric anisotropy, a content of component D is preferably approximately 30% by weight or less based on the weight of the liquid crystal composition. When component D is added thereto, the elastic constant of the composition and the voltage-transmittance curve of the device can be adjusted.

Component E includes compounds (9) to (15). The compounds have phenylene in which hydrogen in a lateral position are replaced by two of halogen, such as 2,3-difluoro-1,4-phenylene. Specific examples of preferred component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds of component E, $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, at least one of hydrogen may be replaced by fluorine; and $R^{17}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine.

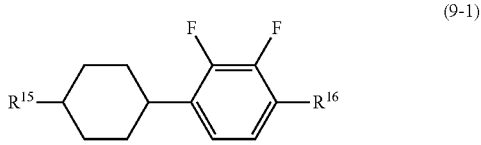
(9-1)

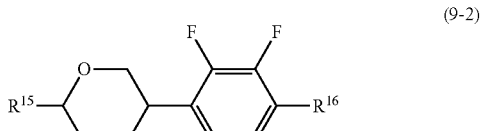
(9-2)

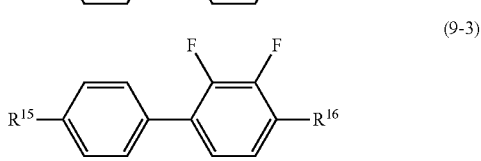
(9-3)

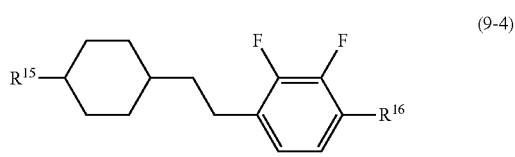
(9-4)

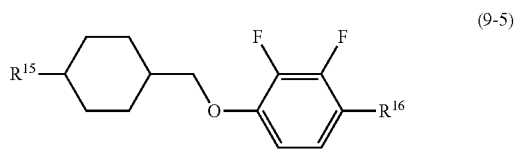
(9-5)

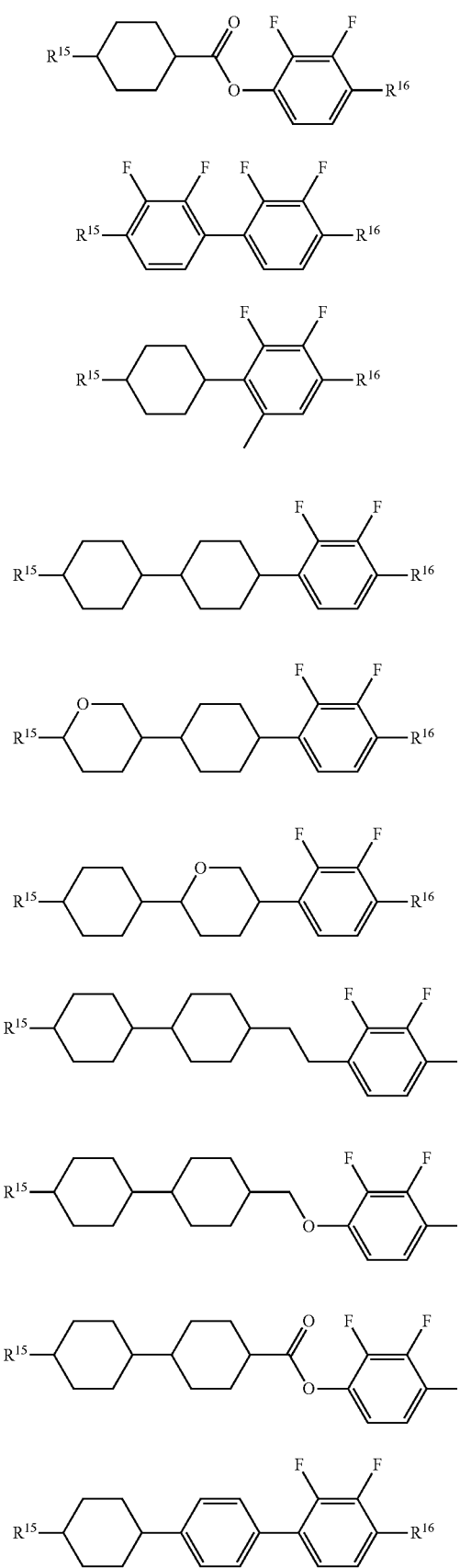
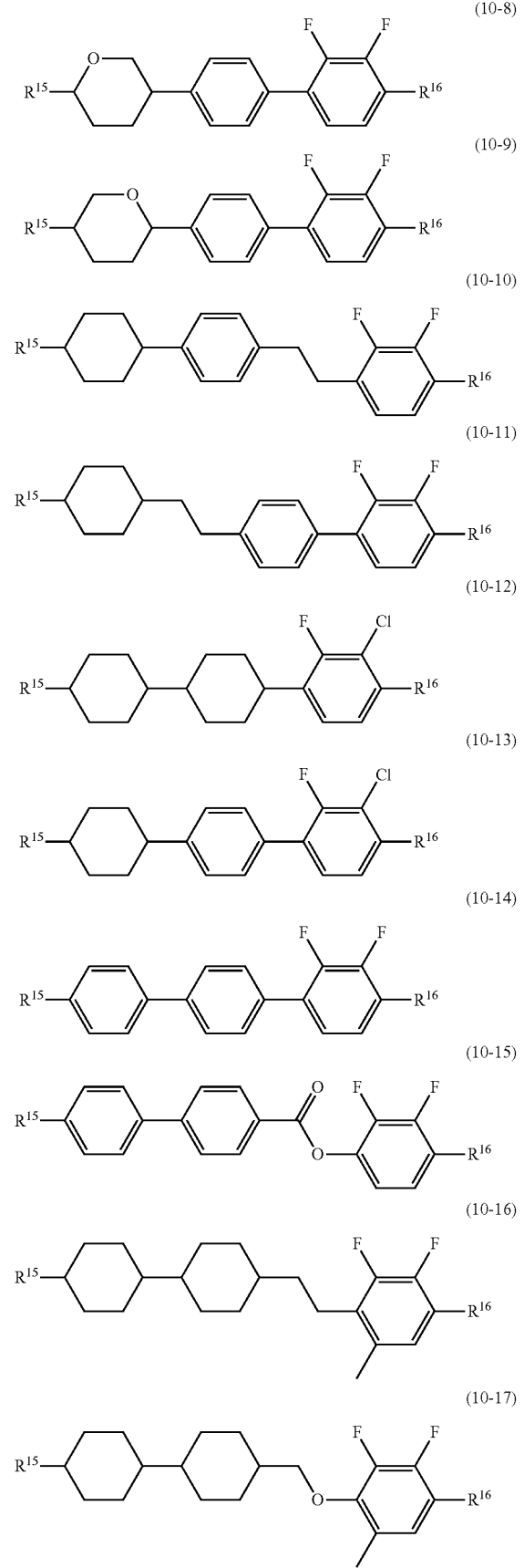

(11-1)
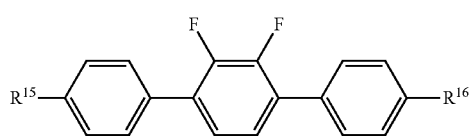
(12-1)
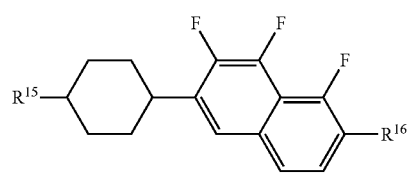
(12-2)
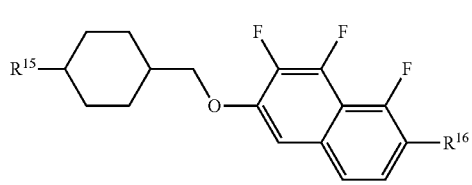
(12-3)
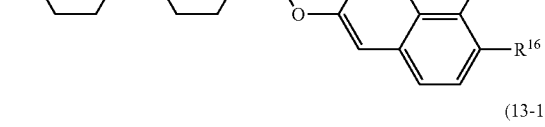
(13-1)
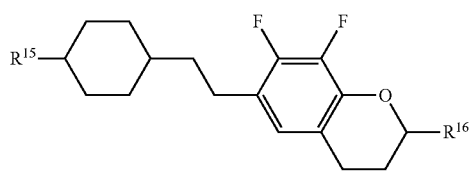
(13-2)
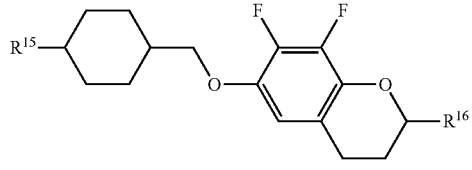
(13-3)
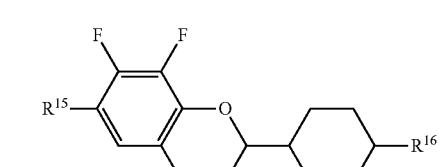
(13-4)
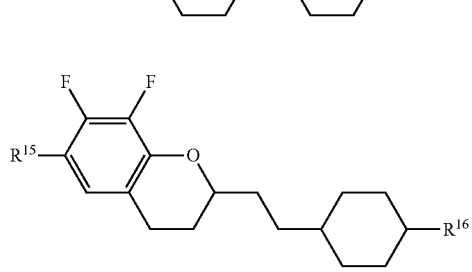
(13-5)
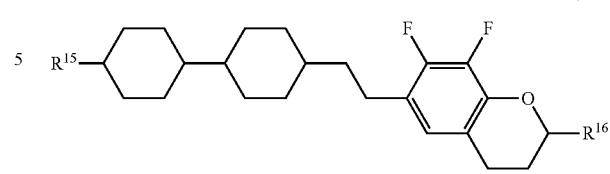
(13-6)
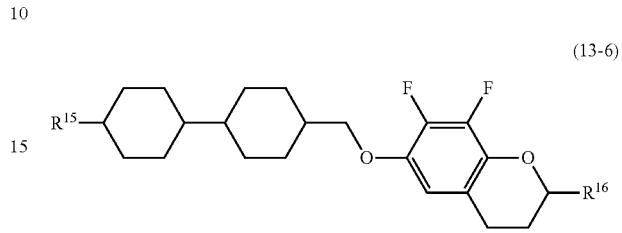
(13-7)
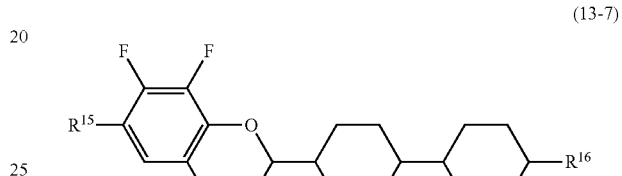
(13-8)
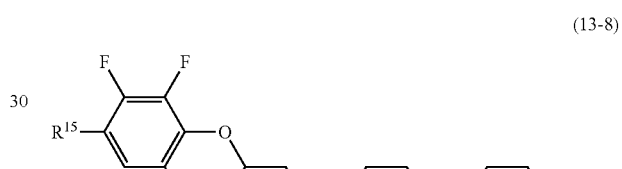
(13-9)
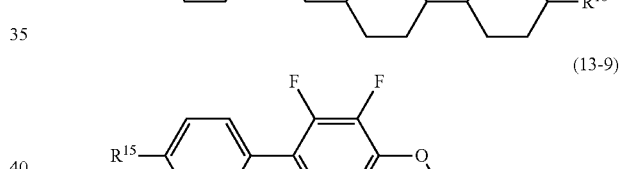
(13-10)
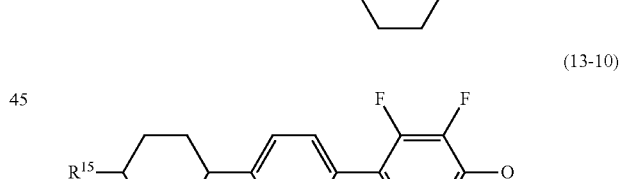
(13-11)
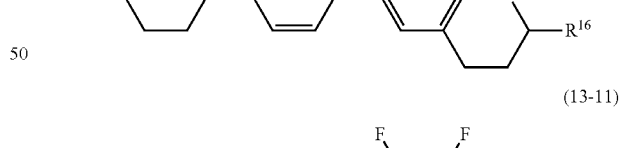
(14-1)
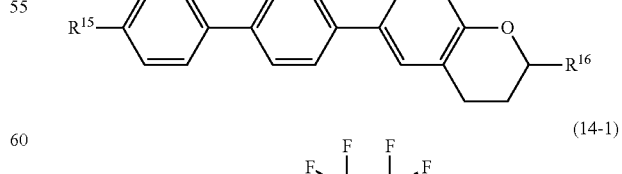

-continued (14-2)
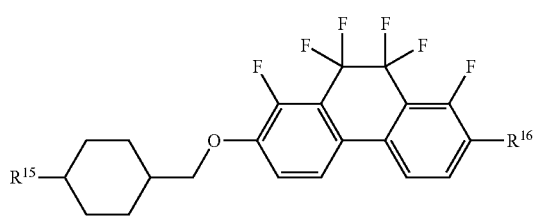

(14-3)
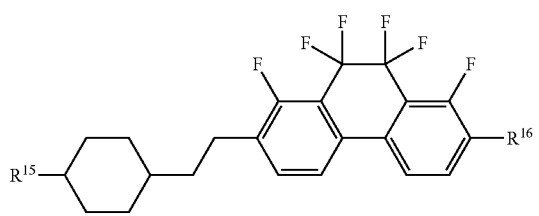

(15-1)
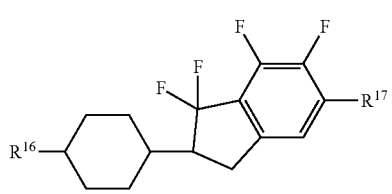

(15-2)
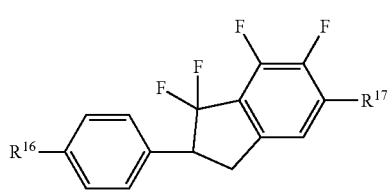

(15-3)
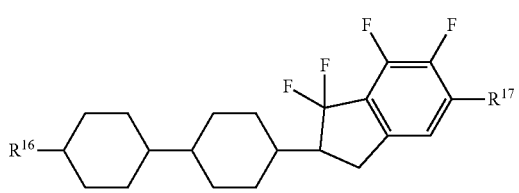

Component E has the large negative dielectric anisotropy. Component E is used for preparing a composition for the mode such as the IPS mode, the VA mode and the PSA mode. As a content of component E is increased, the dielectric anisotropy of the composition negatively increases, but the viscosity also increases. Thus, as long as a desired value of threshold voltage of the device is met, the content is preferably as small as possible. In consideration of the dielectric anisotropy being approximately −5, the content is preferably approximately 40% by weight or more in order to allow sufficient voltage drive.

In component E, compound (9) is a bicyclic compound, and therefore effective mainly in decreasing the viscosity, adjusting the optical anisotropy or increasing the dielectric anisotropy. Compounds (10) and (11) are a tricyclic compound, and therefore effective in increasing the maximum temperature, the optical anisotropy or the dielectric anisotropy. Compounds (12) to (15) are effective in increasing the dielectric anisotropy.

When a composition for the mode such as the IPS mode, the VA mode and the PSA mode is prepared, a content of component E is preferably approximately 40% by weight or more, and further preferably in the range of approximately 50% by weight to approximately 95% by weight based on the weight of the liquid crystal composition. When component E is added to a composition having the positive dielectric anisotropy, a content of component E is preferably approximately 30% by weight or less based on the weight of the liquid crystal composition. When component E is added thereto, the elastic constant of the composition and the voltage-transmittance curve of the device can be adjusted.

The liquid crystal composition satisfying at least one of characteristics such as a high maximum temperature, a low minimum temperature, a small viscosity, a suitable optical anisotropy, a large positive or negative dielectric anisotropy, a large specific resistance, a high stability to ultraviolet light, a high stability to heat and a large elastic constant can be prepared by suitably combining component B, C, D or E described above. A liquid crystal compound different from component B, C, D or E may be added thereto when necessary.

The liquid crystal composition is prepared according to a publicly known method. For example, the component compounds are mixed and dissolved in each other by heating. According to an application, an additive may be added to the composition. Specific examples of the additive include the polymerizable compound, the polymerization initiator, the polymerization inhibitor, the optically active compound, the antioxidant, the ultraviolet light absorber, the light stabilizer, the heat stabilizer and the antifoaming agent. Such additives are well known to those skilled in the art, and described in literature.

The polymerizable compound is added for the purpose of forming the polymer in the liquid crystal composition. The polymerizable compound is polymerized by irradiating the liquid crystal composition with ultraviolet light in a state in which voltage is applied between electrodes to form the polymer in the liquid crystal composition. A suitable pretilt can be obtained by the method, and therefore the response time is shortened, and the liquid crystal display device in which image persistence is improved can also be obtained. Specific preferred examples of the polymerizable compounds include acrylate, methacrylate, a vinyl compound, a vinyloxy compound, propenyl ether, an epoxy compound (oxirane, oxetane) and vinyl ketone. Further preferred examples include a compound having at least one of acryloyloxy and a compound having at least one of methacryloyloxy. Still further preferred examples include a compound having both acryloyloxy and methacryloyloxy.

Further preferred examples include compounds (16-1-1) to (16-1-5), (16-2-1) to (16-2-5), (16-4-1), (16-5-1), (16-6-1) and (16-8) to (16-16). In the compounds (16-1-1) to (16-1-5), (16-2-1) to (16-2-5), (16-4-1), (16-5-1), (16-6-1) and (16-8) to (16-16), $R^{25}$ to $R^{31}$ are independently hydrogen or methyl; v and x are independently 0 or 1; t and u are independently an integer from 1 to 10; and $L^{31}$ to $L^{36}$ are independently hydrogen or fluorine, and $L^{37}$ and $L^{38}$ are independently hydrogen, fluorine or methyl.

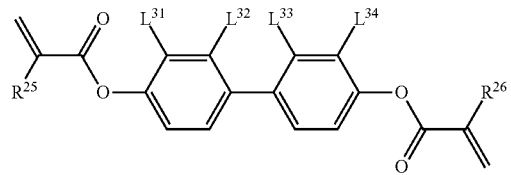
(16-1-1)
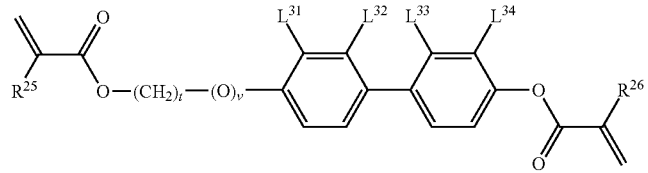
(16-1-2)
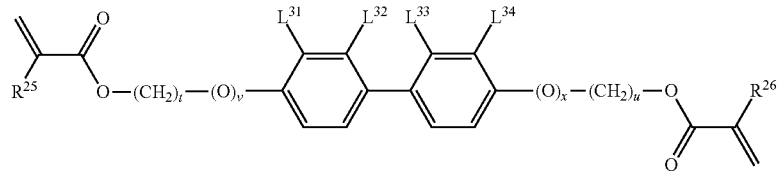
(16-1-3)
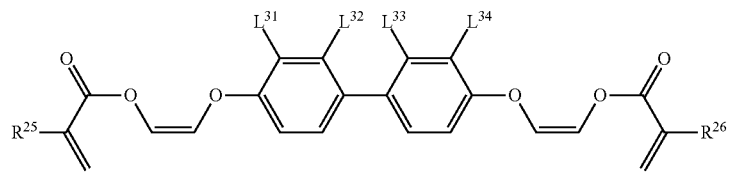
(16-1-4)
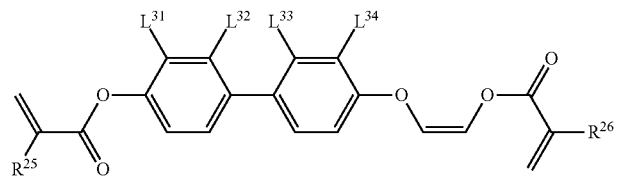
(16-1-5)
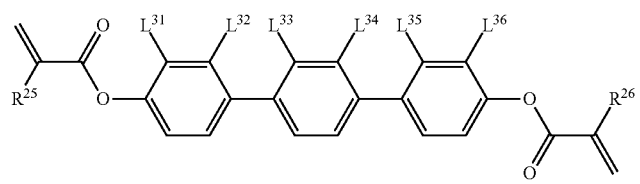
(16-2-1)
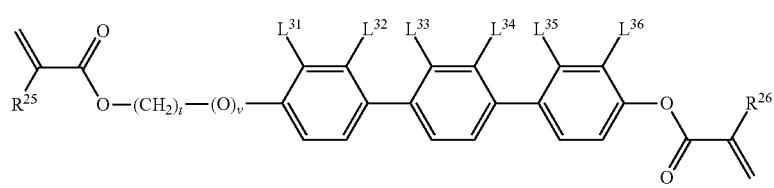
(16-2-2)
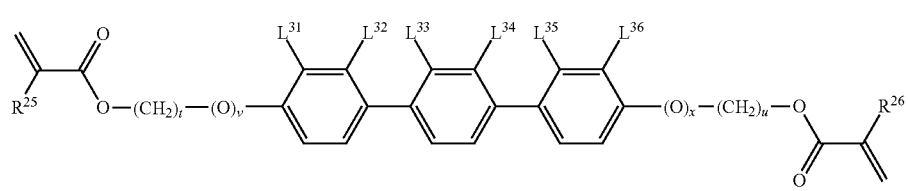
(16-2-3)

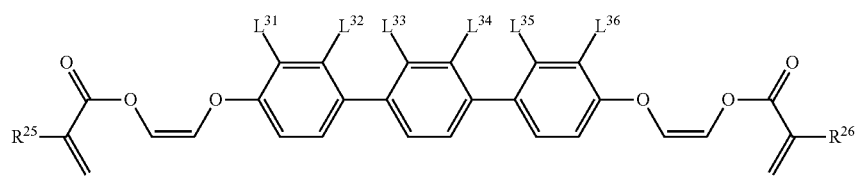
(16-2-4)
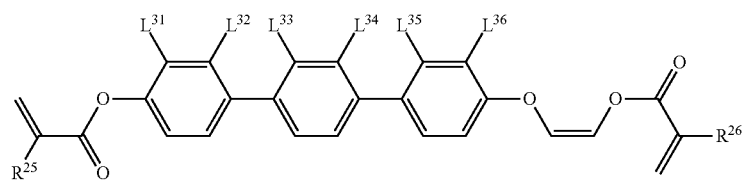
(16-2-5)
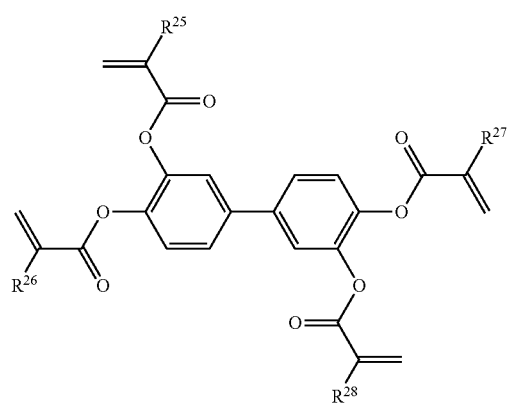
(16-4-1)
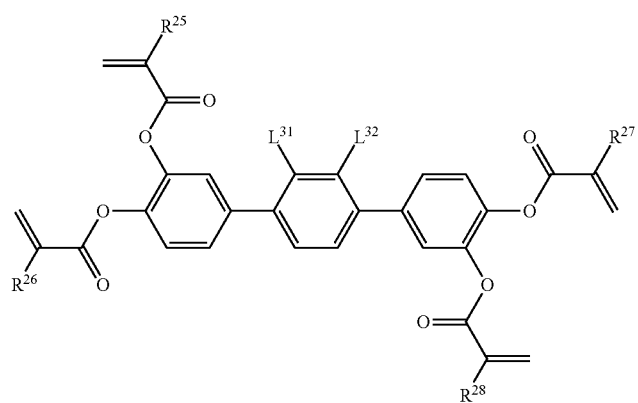
(16-5-1)
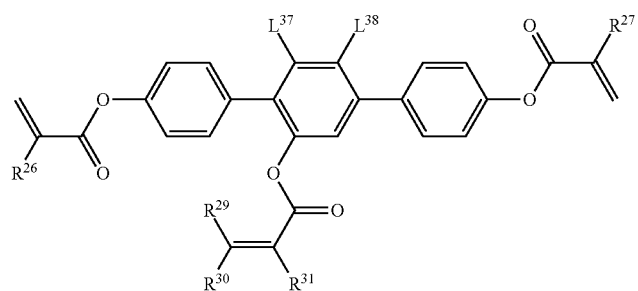
(16-6-1)

-continued
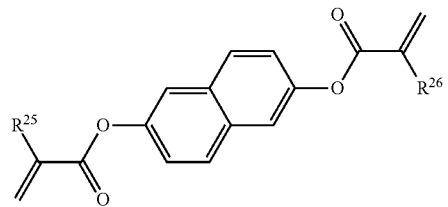
(16-8)
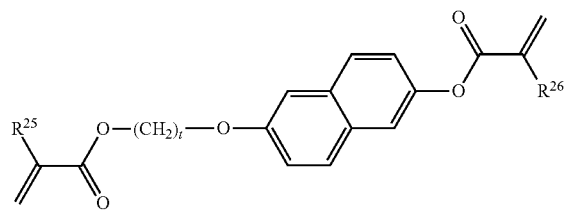
(16-9)
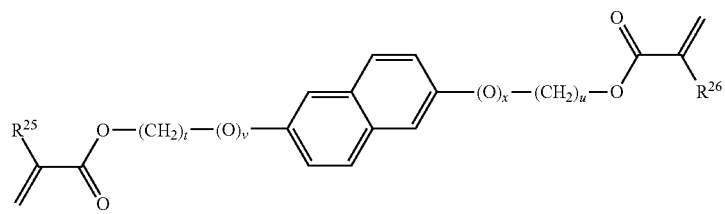
(16-10)
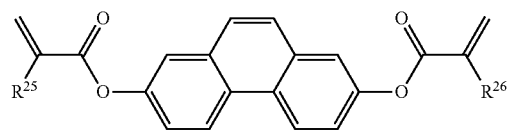
(16-11)
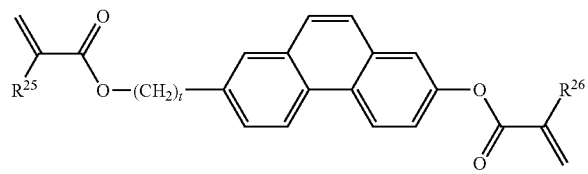
(16-12)
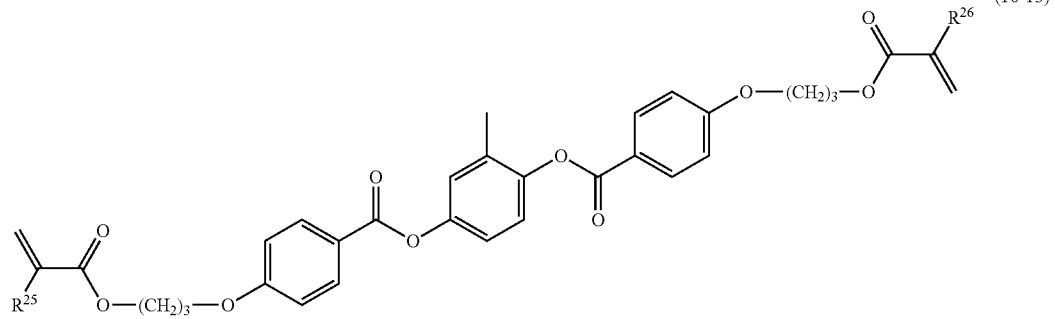
(16-13)
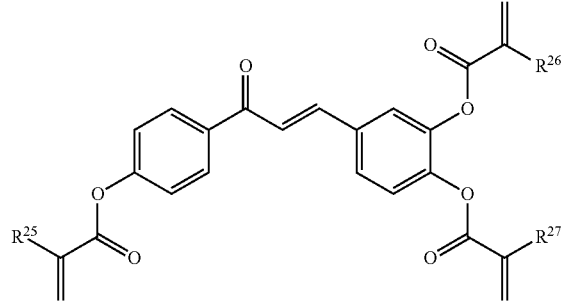
(16-14)

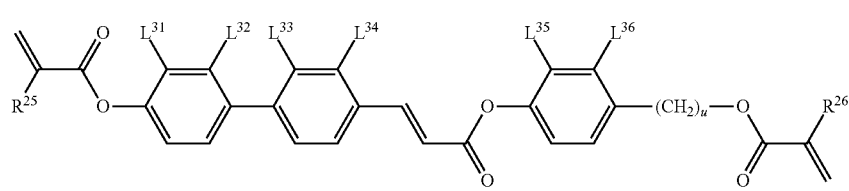

(16-15)

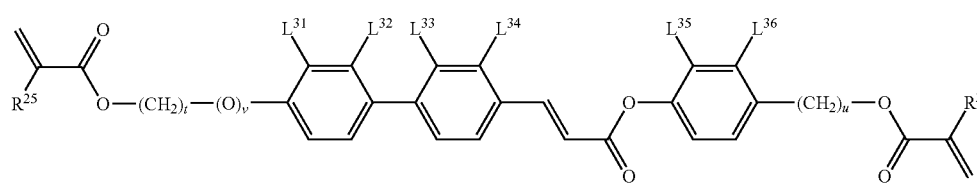

(16-16)

The polymerizable compound can be rapidly polymerized by adding the polymerization initiator. An amount of a remaining polymerizable compound can be decreased by optimizing a reaction temperature. Specific examples of a photoradical polymerization initiator include TPO, 1173 and 4265 from Darocur series, and 184, 369, 500, 651, 784, 819, 907, 1300, 1700, 1800, 1850 and 2959 from Irgacure series, from BASF SE.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone-methyl p-dimethylaminobenzoate mixture and a benzophenone-methyltriethanolamine mixture.

The polymerization can be performed by adding the photoradical polymerization initiator to the liquid crystal composition, and then irradiating the resulting mixture with ultraviolet light in a state in which an electric field is applied thereto. However, an unreacted polymerization initiator or a decomposition product of the polymerization initiator might cause poor display to the device, such as image persistence. In order to avoid such a poor display, photopolymerization may be performed without adding the polymerization initiator. A preferred wavelength of irradiating light is in the range of approximately 150 nanometers to approximately 500 nanometers. A further preferred wavelength is in the range of approximately 250 nanometers to approximately 450 nanometers, and a most preferred wavelength is in the range of approximately 300 nanometers to approximately 400 nanometers.

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include hydroquinone and a hydroquinone derivative such as methylhydroquinone, 4-t-butylcatechol, 4-methoxyphenol or phenothiazine.

The optically active compound is effective in inducing helical structure to provide the liquid crystal molecules with a required twist angle, thereby preventing inverted twist. Addition of the optically active compound allows adjustment of a helical pitch. Two or more optically active compounds may be added thereto for the purpose of adjusting temperature dependence of the helical pitch. Specific preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

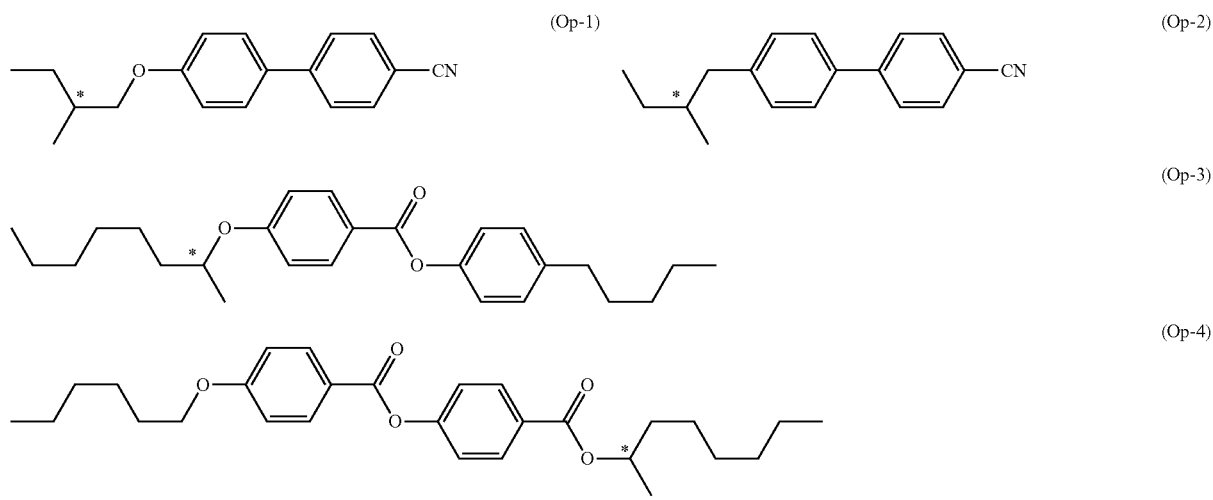

-continued
(Op-5)
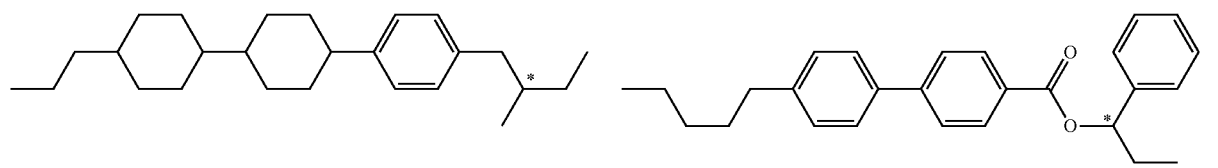
(Op-6)
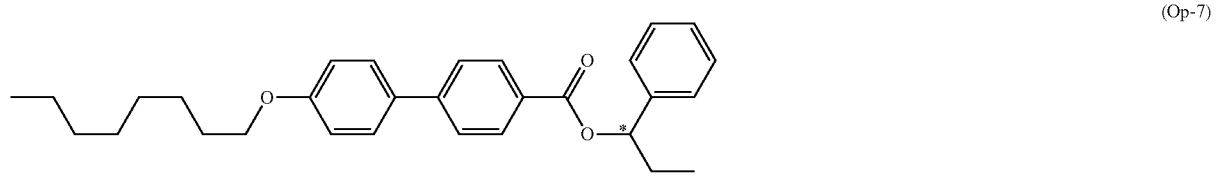
(Op-7)
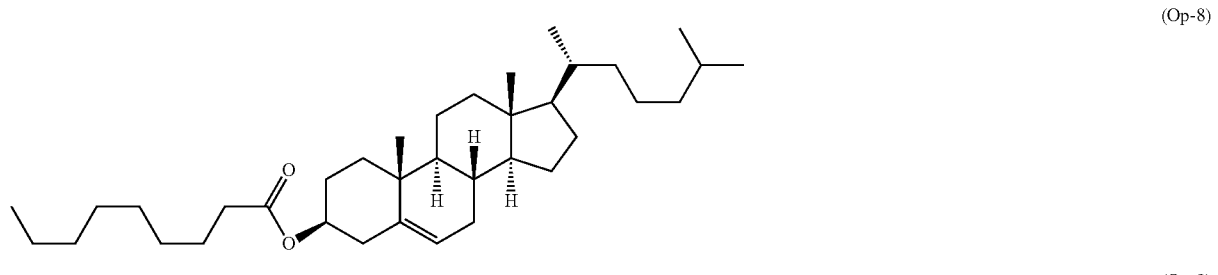
(Op-8)
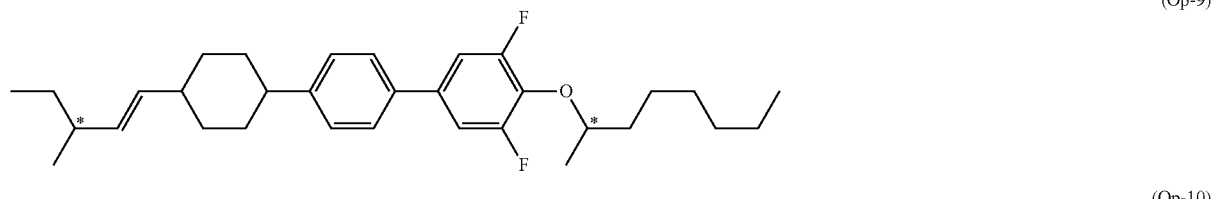
(Op-9)
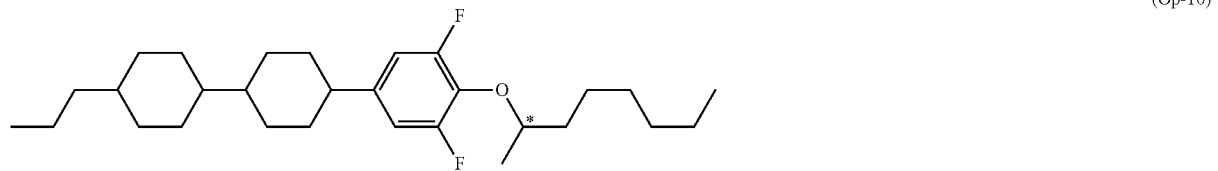
(Op-10)
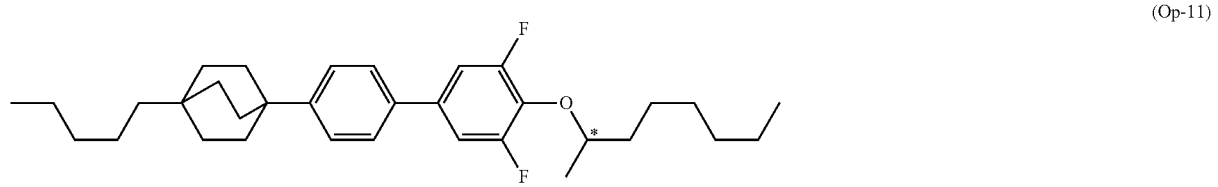
(Op-11)
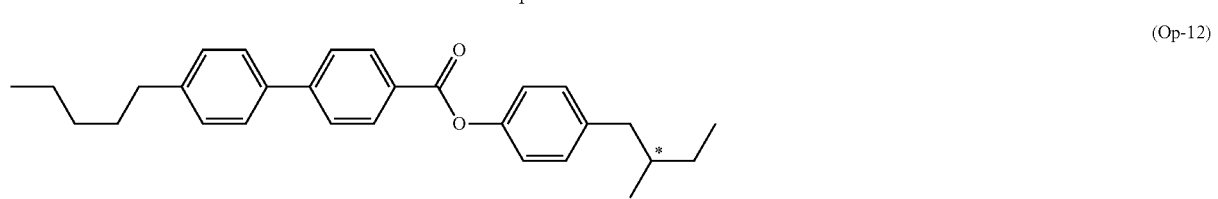
(Op-12)
(Op-13)
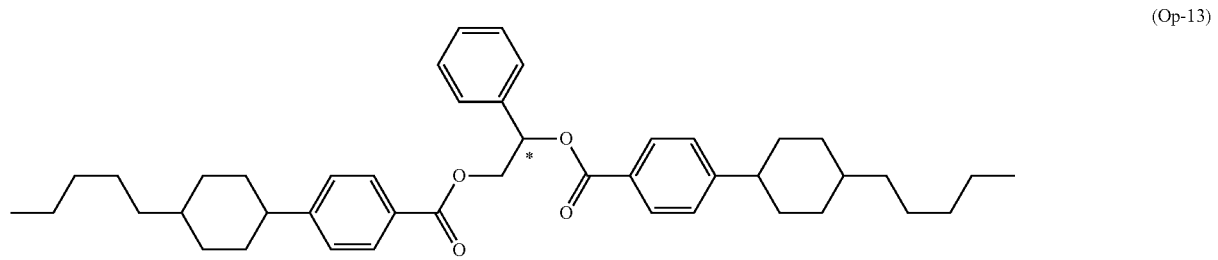

-continued

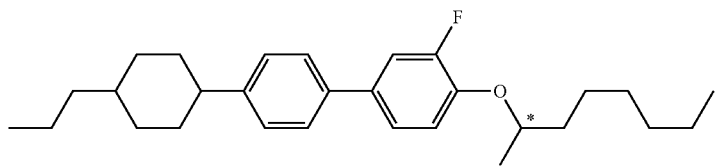
(Op-14)

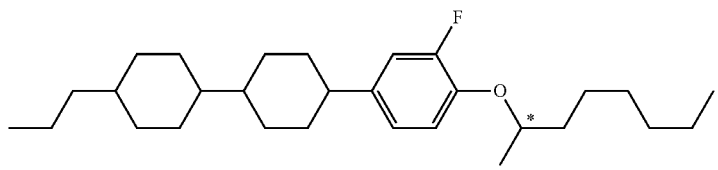
(Op-15)

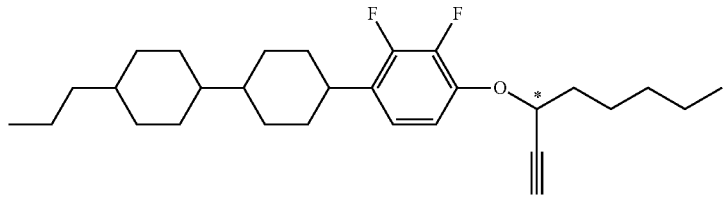
(Op-16)

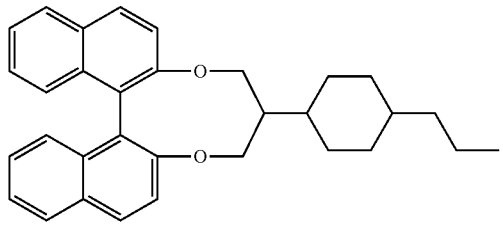
(Op-17)

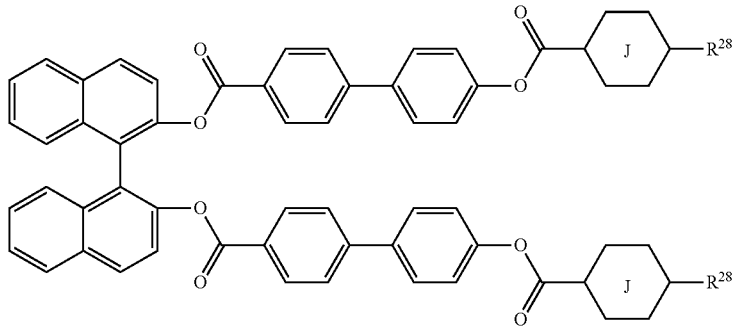
(Op-18)

The antioxidant is effective for maintaining a large voltage holding ratio. Specific preferred examples of the antioxidant include compounds (AO-1) and (AO-2) described below; IRGANOX 415, IRGANOX 565, IRGANOX 1010, IRGANOX 1035, IRGANOX 3114 and IRGANOX 1098 (trade name: BASF SE). The ultraviolet light absorber is effective for preventing a decrease in the maximum temperature. Specific preferred examples of the ultraviolet light absorber include a benzophenone derivative, a benzoate derivative and a triazole derivative. Specific examples include compounds (AO-3) and (AO-4) described below; TINUVIN 329, TINUVIN P, TINUVIN 326, TINUVIN 234, TINUVIN 213, TINUVIN 400, TINUVIN 328 and TINUVIN99-2 (trade name: BASF SE); and 1,4-diazabicyclo[2.2.2]octane (DABCO).

The light stabilizer such as an amine having steric hindrance is preferred for maintaining a large voltage holding ratio. Specific preferred examples of the light stabilizers include compounds (AO-5) and (AO-6) described below, TINUVIN 144, TINUVIN 765 and TINUVIN 770DF (trade name: BASF SE). The heat stabilizer is also effective for maintaining a large voltage holding ratio, and specific preferred examples include IRGAFOS 168 (trade name: BASF SE). The antifoaming agent is effective for preventing foam formation. Preferred examples of the antifoaming agent include dimethyl silicone oil and methylphenyl silicone oil.

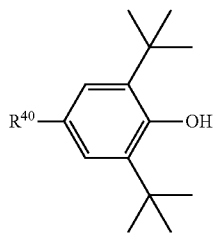
(AO-1)

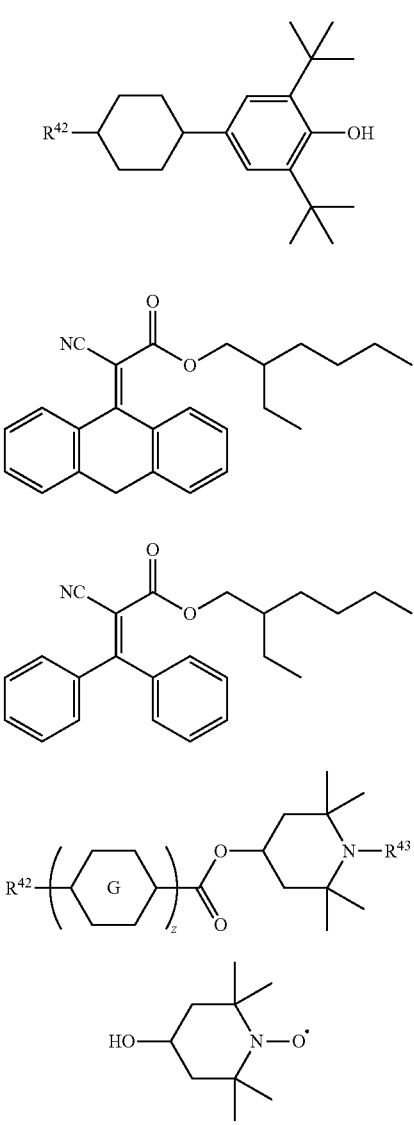

In compound (AO-1), $R^{40}$ is alkyl having 1 to 20 carbons, alkoxy having 1 to 20 carbons, —COOR$^{41}$ or —CH$_2$CH$_2$COOR$^{41}$, and R$^{41}$ is alkyl having 1 to 20 carbons herein. In compounds (AO-2) and (AO-5), $R^{42}$ is alkyl having 1 to 20 carbons. In compound (AO-5), $R^{43}$ is hydrogen, methyl or O. (oxygen radical), ring G is 1,4-cyclohexylene or 1,4-phenylene, and z is 1, 2 or 3.

4. Liquid Crystal Display Device

A liquid crystal composition can be used for a liquid crystal display device having an operating mode such as the PC mode, the TN mode, the STN mode, the OCB mode and the PSA mode, and driven by an active matrix mode. The composition can also be used for a liquid crystal display device having an operating mode such as the PC mode, the TN mode, the STN mode, the OCS mode, the VA mode and the IPS mode, and driven by a passive matrix mode. The devices can be applied to any type of a reflective type, a transmissive type or a transflective type.

The composition can also be used for a nematic curvilinear aligned phase (NCAP) device prepared by microencapsulating a nematic liquid crystal, a polymer dispersed liquid crystal display device (PDLCD) and a polymer network liquid crystal display device (PNLCD), in which a three-dimensional network polymer is formed in the liquid crystal. When an amount of adding the polymerizable compound is approximately 10% by weight or less based on the weight of the liquid crystal composition, the liquid crystal display device having the PSA mode can be prepared. A preferred ratio is in the range of approximately 0.1% by weight to approximately 2% by weight. A further preferred ratio is in the range of approximately 0.2% by weight to approximately 1.0% by weight. The device having the PSA mode can be driven by a driving mode such as the active matrix or the passive matrix. Such devices can be applied to any type of a reflective type, a transmissive type or a transflective type. The device having the polymer dispersed mode can also be prepared by increasing an amount of adding the polymerizable compound.

In a device having a polymer sustained alignment mode, a polymer contained in a liquid crystal composition can align the liquid crystal molecules. A polar compound assists alignment of the liquid crystal molecules. More specifically, the polar compound can be used in place of an alignment film. One example of the method for manufacturing such a device is as described below. A device having two substrates referred to as an array substrate and a color filter substrate is arranged. The substrate has no the alignment film. At least one of the substrates has an electrode layer. The liquid crystal composition is prepared by mixing the liquid crystal compounds. The polymerizable compound and the polar compound are added to the composition. The additive may be further added when necessary. The composition is injected into the device. The device is irradiated with light in a state in which voltage is applied thereto. Ultraviolet light is preferred. The polymerizable compound is polymerized by irradiation with light. The composition containing the polymer is formed by the polymerization, and a device having the PSA mode can be manufactured.

In the procedure, the polar compound is arranged on the substrate because the polar group interacts with the surface of the substrate. The polar compound can align the liquid crystal molecules. When voltage is applied thereto, alignment of the liquid crystal molecules are further promoted due to an effect of the electric field. The polymerizable compound is also aligned according to the alignment. The polymerizable compound is polymerized by irradiation with ultraviolet light in the above state, and therefore the polymer in which the alignment is maintained is formed. The alignment of the liquid crystal molecules is additionally stabilized due to the effect of the polymer, and therefore the response time of the device is shortened. The image persistence is caused due to poor operation in the liquid crystal molecules, and therefore is to be simultaneously improved by the effect of the polymer.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples (including Synthesis Examples and Use Examples). However, the invention is not limited by the Examples. The invention includes a mixture of a composition in Use Example 1 and a composition in Use Example 2. The invention also includes a mixture prepared by mixing at least two compositions in Use Examples.

1. Example of Compound (1)

Compound (1) was prepared according to procedures described in Examples. Unless otherwise described, a reaction was performed under a nitrogen atmosphere. Compound (1) was prepared according to procedures described in Example 1 or the like. The thus prepared compound was identified by a method such as an NMR analysis. Characteristics of compound (1), the liquid crystal compound, the composition and the device were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane (TMS) was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: GC-2010 Gas Chromatograph made by Shimadzu Corporation was used for measurement. A capillary column DB-1 (length 60 m, bore 0.25 mm, film thickness 0.25 μm) made by Agilent Technologies, Inc. was used. Helium (1 milliliter per minute) was used as a carrier gas. A temperature of a sample injector and a detector (FID) part were set to 300° C. and 300° C., respectively. A sample was dissolved in acetone and prepared to be a 1 weight % solution, and then 1 microliter of the solution obtained was injected into the sample injector. A recorder such as GC Solution System made by Shimadzu Corporation was used.

HPLC analysis: For measurement, Prominence (LC-20AD; SPD-20A) made by Shimadzu Corporation was used. As a column, YMC-Pack ODS-A (length: 150 mm, bore: 4.6 mm, particle diameter: 5 μm) made by YMC GmbH was used. As an eluate, acetonitrile and water were appropriately mixed and used. As a detector, a UV detector, an RI detector, a CORONA detector or the like was appropriately used. When the UV detector was used, a detection wavelength was adjusted to 254 nanometers. A sample was dissolved in acetonitrile and prepared to be a 0.1 weight % solution, and then 1 microliter of the solution was injected into a sample injector. As a recorder, C-R7Aplus made by Shimadzu Corporation was used.

Ultraviolet-Visible spectrophotometry: For measurement, PharmaSpec UV-1700 made by Shimadzu Corporation was used. A detection wavelength was adjusted in the range from 190 nanometers to 700 nanometers. A sample was dissolved in acetonitrile, and prepared to be a solution of 0.01 millimole per liter, and measurement was carried out by putting the solution in a quartz cell (optical path length 1 cm).

Sample for measurement: Upon measuring phase structure and a transition temperature (a clearing point, a melting point, a polymerization starting temperature or the like), a liquid crystal compound itself was used as a sample. Upon measuring characteristics of a nematic phase, such as a maximum temperature, viscosity, optical anisotropy and dielectric anisotropy, a mixture prepared by mixing the compound with a base liquid crystal was used as a sample.

When a sample in which the compound was mixed with the base liquid crystal was used, measurement was carried out according to a method described below. The sample was prepared by mixing 15% by weight of the compound and 85% by weight of the base liquid crystal. Then, extrapolated values were calculated from measured values of the sample, according to an extrapolation method, expressed by an equation below, and the extrapolated values were described. {Extrapolated value}={100×(measured value of a sample)−(% by weight of base liquid crystal)×(measured value of the base liquid crystal)}/(% by weight of the compound).

When crystals (or a smectic phase) precipitated at 25° C. even at the ratio of the compound to the base liquid crystal, a ratio of the compound to the base liquid crystal was changed in the order of (10% by weight:90% by weight), (5% by weight:95% by weight) and (1% by weight:99% by weight), and characteristics of the sample at a ratio at which no crystals (or no smectic phase) precipitated at 25° C. were measured. In addition, unless otherwise noted, the ratio of the compound to the base liquid crystal was 15% by weight: 85% by weight.

When the dielectric anisotropy of the compound was zero or positive, base liquid crystal (A) described below was used. A ratio of each component is expressed in terms of weight percent (% by weight).

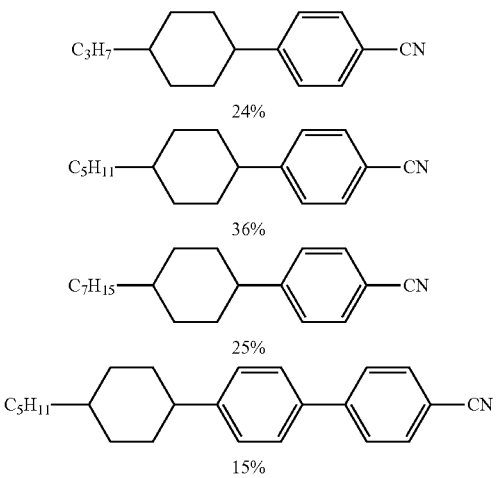

When the dielectric anisotropy of the compound was zero or negative, base liquid crystal (B) described below was used. A ratio of each component is expressed in terms of weight percent (% by weight).

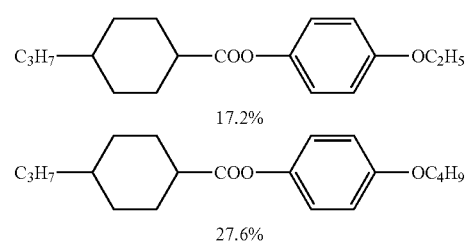

-continued

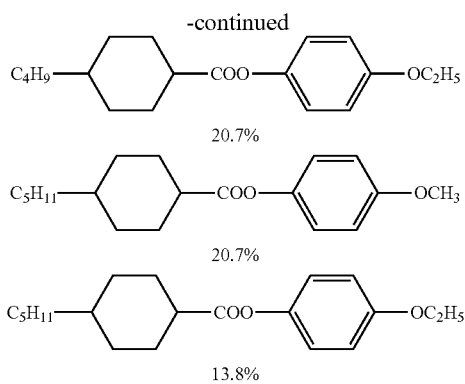

Measuring methods: Measurement of characteristics was carried out by the methods described below. Most of the measuring methods are applied as described in the Standard of the Japan Electronics and Information Technology Industries Association (JEITA EIAJ ED-2521B) discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc. or a high sensitivity differential scanning calorimeter, X-DSC7000, made by SII NanoTechnology, Inc. was used. A sample was heated and then cooled at a rate of 3° C. per minute, a starting point of an endothermic peak or an exothermic peak caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as the smectic phase and the nematic phase is occasionally abbreviated as "minimum temperature of the liquid crystal phase." Temperature at which the compound undergoes transition from the liquid crystal phase to the liquid is occasionally abbreviated as "clearing point."

The crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from a nematic phase to an isotropic liquid was measured. Maximum temperature of the nematic phase is occasionally abbreviated as "maximum temperature." When the sample was a mixture of compound (1) and the base liquid crystal, the maximum temperature was expressed in terms of a symbol $T_{NI}$. When the sample was a mixture of compound (1) and a compound such as component B, C or D, the maximum temperature was expressed in terms of a symbol NI.

(4) Minimum Temperature of Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., $T_c$ was expressed as $T_c \leq -20°$ C. Minimum temperature of the nematic phase is occasionally abbreviated as "minimum temperature."

(5) Viscosity (Bulk Viscosity; η; Measured at 20° C.; mPa·s)

For measurement, a cone-plate (E type) rotational viscometer made by Tokyo Keiki, Inc. was used.

(6) Optical Anisotropy (Refractive Index Anisotropy; Δn; Measured at 25° C.)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(7) Specific Resistance (ρ; Measured at 25° C.; Ωcm)

Into a vessel equipped with electrodes, 1.0 milliliter of a sample was injected. A direct current voltage (10 V) was applied to the vessel, and a direct current after 10 seconds was measured. Specific resistance was calculated from the following equation: (specific resistance)={(voltage)×(electric capacity of the vessel)}/{(direct current)×(dielectric constant of vacuum)}.

(8) Voltage Holding Ratio (VHR-1; Measured at 25° C.; %):

A TN device used for measurement had a polyimide alignment film, and a distance (cell gap) between two glass substrates was 5 micrometers. A sample was put in the device, and the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

(9) Voltage Holding Ratio (VHR-2; Measured at 80° C.; %)

A voltage holding ratio was measured according to method identical with the method described above except that measurement was carried out at 80° C. in place of 25° C. The results were expressed in terms of a symbol VHR-2.

The method of measuring the characteristics is occasionally different between a sample having the positive dielectric anisotropy and a sample having the negative dielectric anisotropy. The measuring methods when the dielectric anisotropy is positive were described in sections (10a) to (14a). The methods when the dielectric anisotropy is negative were described in sections (10b) to (14b).

(10a) Viscosity (Rotational Viscosity; γ1; Measured at 25° C.; mPa·s)

Positive dielectric anisotropy: Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. A value of dielectric anisotropy required for the calculation was determined using the device with which the rotational viscosity was measured and by a method described below.

(10b) Viscosity (Rotational Viscosity; γ1; Measured at 25° C.; mPa·s)

Negative dielectric anisotropy: Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage application, voltage was repeatedly applied under the conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. As dielectric anisotropy required for the calculation, a value measured in a section of dielectric anisotropy described below was used.

(11a) Dielectric Anisotropy (Δ∈; Measured at 25° C.)

Positive dielectric anisotropy: A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in a major axis direction of the liquid crystal molecules was measured. Sine waves (0.5 V, 1 kHz) were applied to the device, and after 2 seconds, a dielectric constant (∈⊥) in a minor axis direction of the liquid crystal molecules was measured. A value of dielectric anisotropy was calculated from an equation: Δ∈=∈∥−∈⊥.

(11b) Dielectric Anisotropy (Δ∈; Measured at 25° C.)

Negative dielectric anisotropy: A value of dielectric anisotropy was calculated from an equation: Δ∈=∈∥−∈⊥. A dielectric constant (∈∥ and ∈⊥) was measured as described below.

(1) Measurement of dielectric constant (∈∥): An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in the major axis direction of liquid crystal molecules was measured.

(2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(12a) Elastic Constant (K; Measured at 25° C.; pN)

Positive dielectric anisotropy: HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K is a mean value of the thus determined $K_{11}$, $K_{22}$ and $K_{33}$.

(12b) Elastic Constant ($K_{11}$ and $K_{33}$; Measured at 25° C.; pN)

Negative dielectric anisotropy: Elastic Constant Measurement System Model EC-1 made by TOYO Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(13a) Threshold Voltage (Vth; Measured at 25° C.; V)

Positive dielectric anisotropy: An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage is expressed in terms of a voltage at 90% transmittance.

(13b) Threshold Voltage (Vth; Measured at 25° C.; V)

Negative dielectric anisotropy: An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage was expressed in terms of a voltage at 10% transmittance.

(14a) Response Time (τ; Measured at 25° C.; ms)

Positive dielectric anisotropy: An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was 5.0 micrometers and a twist angle was 80 degrees. Rectangular waves (60 Hz, 5 V, 0.5 sec) were applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time (τr; millisecond) is a period of time required for the change in transmittance from 90% to 10%. A fall time (τf: millisecond) is a period of time required for the change in transmittance from 10% to 90%. Response time was presented by a sum of the thus obtained rise time and fall time.

(14b) Response Time (τ; Measured at 25° C.; ms)

Negative dielectric anisotropy: An LCD-5100 luminance meter made by Otsuka Electronics Co., Ltd. was used for measurement. A light source was a halogen lamp. A low-pass filter was set at 5 kHz. A sample was put in a normally black mode PVA device in which a distance (cell gap) between two glass substrates was 3.2 micrometers and a rubbing direction was anti-parallel. The device was sealed with an ultraviolet-curable adhesive. The device was applied with a voltage of a little exceeding a threshold voltage for 1 minute, and then was irradiated with an ultraviolet light of 23.5 mW/cm² for 8 minutes, while applying a voltage of 5.6 V. Rectangular waves (60 Hz, 10 V, 0.5 sec) were applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time was expressed in terms of time required for a change from 90% transmittance to 10% transmittance (fall time; millisecond).

Raw Material

Solmix (registered trademark) A-11 is a mixture of ethanol (85.5%), methanol (13.4%) and isopropanol (1.1%), and was purchased from Japan Alcohol Trading Co., Ltd.

Synthesis Example 1

Synthesis of Compound (No. 24)

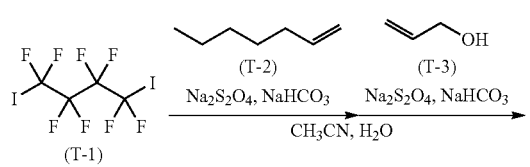

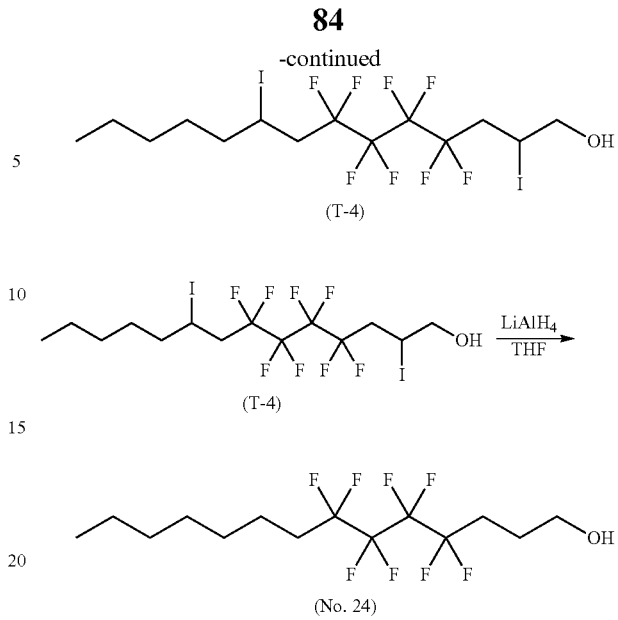

First Step

Compound (T-1) (14.9 g), compound (T-2) (4.61 mL) and acetonitrile (220 mL) were put in a reaction vessel, and the resulting mixture was cooled down to 0° C. Thereto, a water (38.0 mL) solution of sodium dithionite (3.81 g) and sodium hydrogencarbonate (1.38 g) was slowly added dropwise, and further stirred for 1 hour. After adding compound (T-3) (2.24 mL) thereto, a water (76.0 mL) solution of sodium dithionite (7.62 g) and sodium hydrogencarbonate (2.76 g) was slowly added dropwise, and a reaction mixture was stirred for 2 hours while returning the mixture to room temperature. The reaction mixture was poured into ice water, and an aqueous layer was extracted with ethyl acetate. A combined organic layer was washed with brine, and dried over anhydrous magnesium sulfate. The resulting solution was concentrated under reduced pressure, and the residue was purified by silica gel chromatography (toluene:ethyl acetate=10:1 in a volume ratio) to give compound (T-4) (6.68 g; 33%).

Second Step

Lithium aluminum hydride (0.699 g) and THF (80 mL) were put in a reaction vessel, and the resulting mixture was cooled down to −10° C. Thereto, a THF (20 mL) solution of compound (T-4) (3.21 g) was slowly added dropwise, and a reaction mixture was stirred for 8 hours while returning the mixture to room temperature. The reaction mixture was poured into saturated aqueous solution of ammonium chloride, and after filtering off an insoluble matter, an aqueous layer was extracted with ethyl acetate. A combined organic layer was washed with water, and dried over anhydrous magnesium sulfate. The resulting solution was concentrated under reduced pressure, and the residue was purified by silica gel chromatography (toluene:ethyl acetate=10:1 in a volume ratio). Then, the residue was further purified through recrystallization from a mixed solvent of heptane and toluene (1:1 in a volume ratio) to give compound (No. 24) (1.16 g; 61%).

NMR analysis values of obtained compound (No. 24) are as described below.

¹H-NMR: Chemical shift δ (ppm; CDCl₃): 3.74 (t, J=6.2 Hz, 2H), 2.27-2.13 (m, 2H), 2.10-1.97 (m, 2H), 1.91-1.82 (m, 2H), 1.64-1.54 (m, 2H), 1.42-1.24 (m, 8H), 0.89 (t, J=7.2 Hz, 3H).

Characteristics of compound (No. 24) were as described below. Transition temperature: C 34.1 I. A maximum temperature (extrapolated value) was obtained by the method according to section (3) from a mixture in which 15% by weight of compound (No. 24) was mixed with 85% by weight of the base liquid crystal. Maximum temperature $(T_{NI})=-82.3°$ C.

Synthesis Example 2

Synthesis of Compound (No. 105)

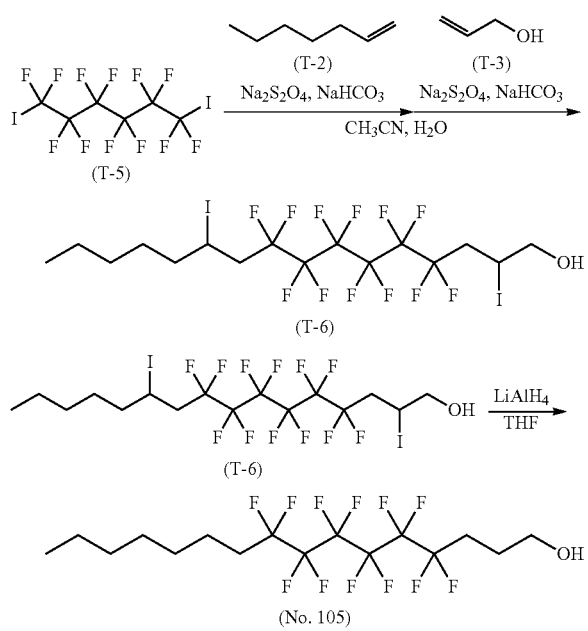

First Step

Compound (T-6) (9.88 g; 31%) was obtained by using compound (T-5) (25.0 g) as a raw material and by a technique similar to the technique in the first step in Synthesis Example 1.

Second Step

Compound (No. 105) (5.01 g; 79%) was obtained using compound (T-6) (9.88 g) as a raw material and by a technique similar to the technique in the second step in Synthesis Example 1.

NMR-analysis values of obtained compound (No. 105) are as described below.

$^1$H-NMR: Chemical shift δ (ppm; CDCl$_3$): 3.75 (t, J=6.1 Hz, 2H), 2.28-2.14 (m, 2H), 2.12-1.98 (m, 2H), 1.92-1.82 (m, 2H), 1.64-1.53 (m, 2H), 1.42-1.23 (m, 8H), 0.89 (t, J=7.0 Hz, 3H).

Characteristics of compound (No. 105) were as described below. Transition temperature: C$_1$ 40.1 C$_2$ 47.8 I. A maximum temperature (extrapolated value) was obtained by the method according to section (3) from a mixture in which 15% by weight of compound (No. 105) was mixed with 85% by weight of the base liquid crystal. Maximum temperature $(T_{NI})=-15.0°$ C.

Synthesis Example 3

Synthesis of Compound (No. 10)

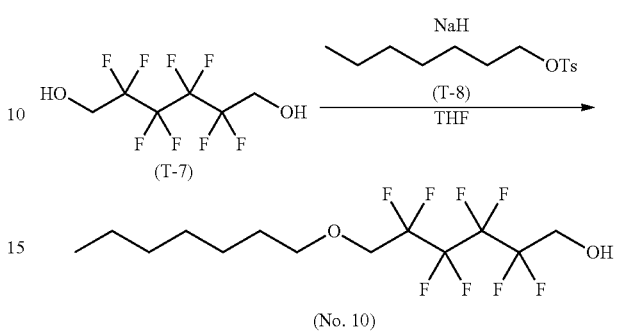

First Step

Compound (T-7) (10.0 g) and 1,4-dioxane (500 mL) were put in a reaction vessel, and the resulting mixture was cooled down to 0° C. Thereto, sodium hydride (1.83 g) was slowly added, and further stirred for 3 hours at 50° C. Next, compound (T-8) (9.64 mL) was slowly added thereto at room temperature, and subjected to reflux under heating for 10 hours. A reaction mixture was poured into a saturated aqueous solution of ammonium chloride, and an aqueous layer was extracted with ethyl acetate. A combined organic layer was washed with brine, and dried over anhydrous magnesium sulfate. The resulting solution was concentrated under reduced pressure, and the residue was purified by silica gel chromatography (toluene:ethyl acetate=10:1 in a volume ratio). Then, the residue was further purified through recrystallization from heptane to give compound (No. 10) (4.90 g; 36%).

NMR-analysis values of obtained compound (No. 10) are as described below.

$^1$H-NMR: Chemical shift δ (ppm; CDCl$_3$): 4.08 (td, J=14.3 Hz, J=7.5 Hz, 2H), 3.91 (t, J=14.2 Hz, 2H), 3.59 (t, J=6.6 Hz, 2H), 2.03 (t, J=7.5 Hz, 1H), 1.64-1.56 (m, 2H), 1.38-1.23 (m, 8H), 0.88 (t, J=7.0 Hz, 3H).

Characteristics of compound (No. 10) were as described below. Transition temperature: C −31.5 I. A mixture of 15% by weight of compound (No. 10) and 85% by weight of the base liquid crystal (A) was a transparent liquid. At the ratio, liquid crystallinity of the base liquid crystal decreased, and the maximum temperature of the mixture was lower than room temperature. Thus, a mixture was prepared at a ratio of 5% by weight and 95% by weight, and the maximum temperature (extrapolated value) was obtained by the method according to section (3) in the experiment. Maximum temperature $(T_{NI})=-132°$ C.

Comparative Example 1

Compound (S-1) was selected for comparison, and characteristics were measured. The reason is that the compound is described in WO 2012-104008 A and similar to the compound of the invention. In addition, a commercial item (made by Tokyo Chemical Industry Co., Ltd.) was directly used as compound (S-1).

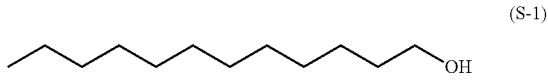

Characteristics of comparative compound (S-1) were as described below. Transition temperature: C 23.7 I. A mixture of 15% by weight of compound (S-1) and 85% by weight of the base liquid crystal (A) was a transparent liquid. At the ratio, liquid crystallinity of the base liquid crystal decreased, and the maximum temperature of the mixture was lower than room temperature. Thus, a mixture was prepared at a ratio of 10% by weight and 90% by weight, and the maximum temperature (extrapolated value) was obtained by the method according to section (3) in the experiment. Maximum temperature $(T_{NI})=-191°$ C.

TABLE 2

| Comparison of maximum temperature ($T_{NI}$) | |
| --- | --- |
| Liquid crystal compounds | $T_{NI}$ ° (C.) |
| Compound (No. 24) | −82.3 |
| Compound (No. 105) | −15 |

TABLE 2-continued

| Comparison of maximum temperature ($T_{NI}$) | |
| --- | --- |
| Liquid crystal compounds | $T_{NI}$ ° (C.) |
| Compound (No. 10) | −132 |
| Comparative compound (S-1) | −191 |

All of compound (No. 24), compound (No. 105) and compound (No. 10) prepared in Synthesis Examples 1 to 3 showed a higher maximum temperature in comparison with comparative compound (S-1). The reason is presumably that a poly(difluoromethylene) chain has a higher rigidity in comparison with an alkyl chain, and therefore compound (1) has higher liquid crystallinity than the comparative compound has. Accordingly, the compound according to the invention can be concluded to have superior characteristics in view of having a smaller negative effect when the compound is added to the liquid crystal composition.

According to the synthetic methods described in Example 1 to Example 3, compounds (No. 1) to (No. 220) described below can be prepared.

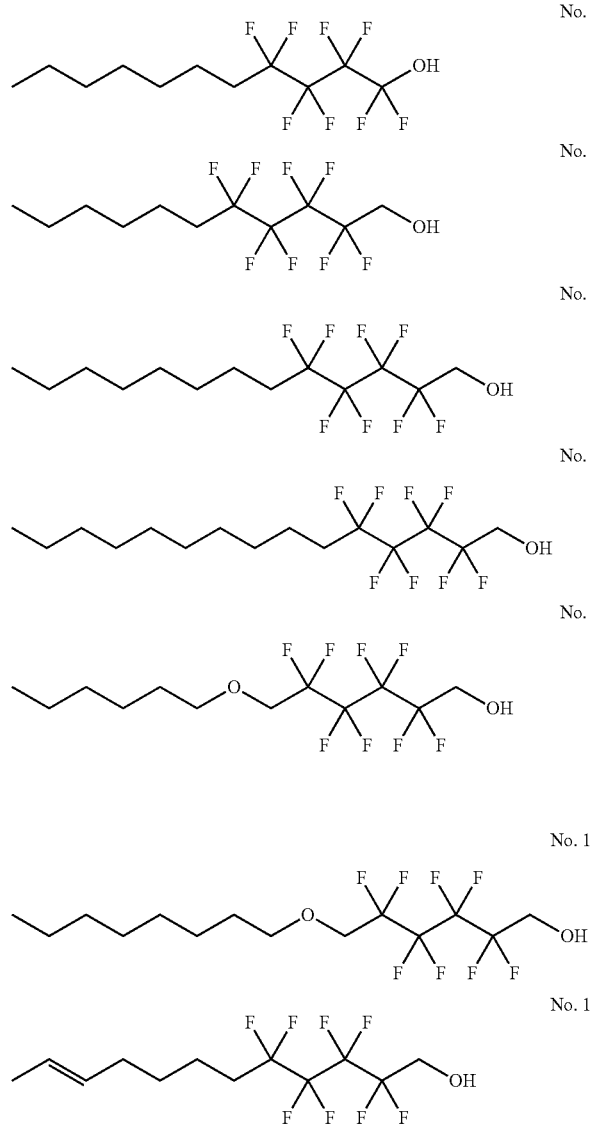
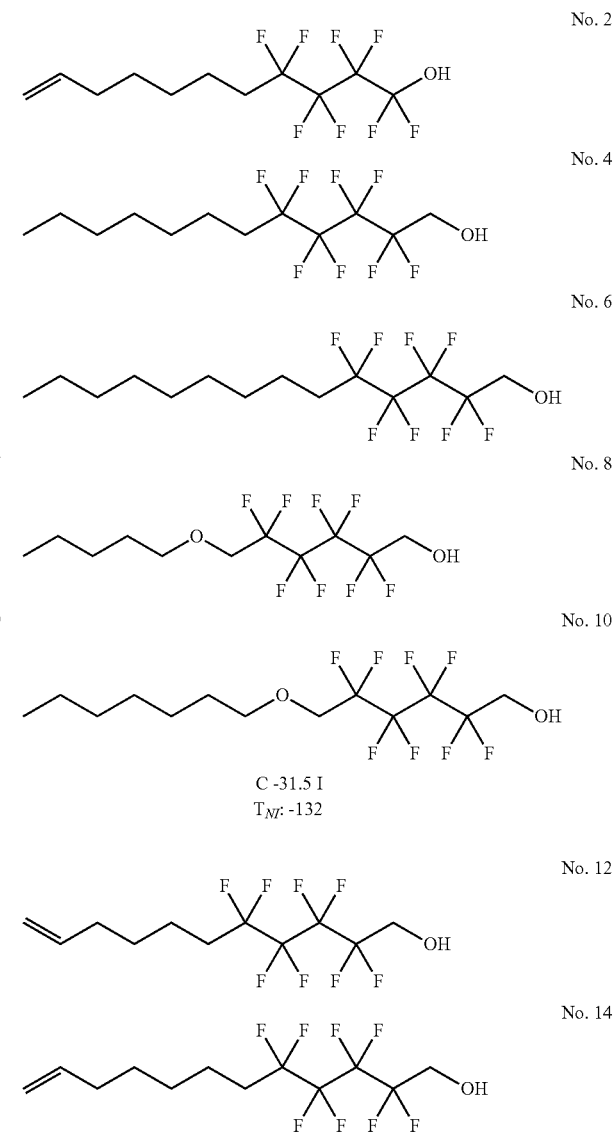

-continued
No. 15
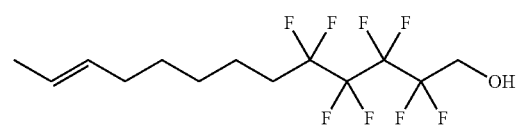
No. 16
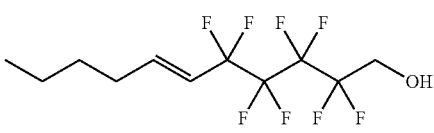
No. 17
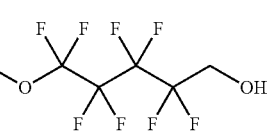
No. 18
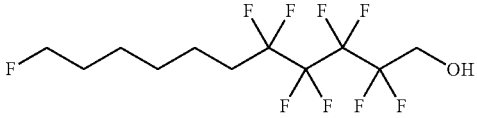
No. 19
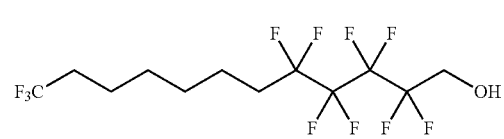
No. 20
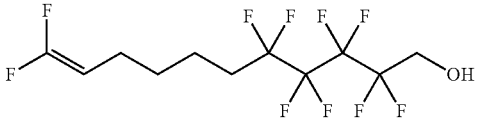
No. 21
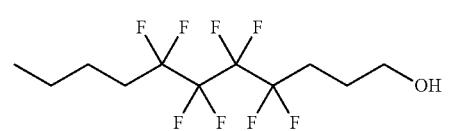
No. 22
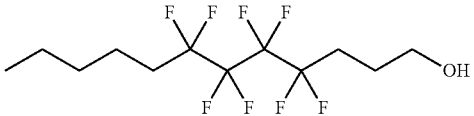
No. 23
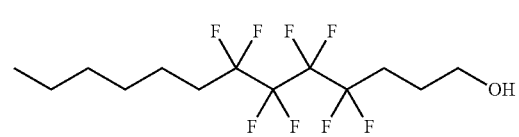
No. 24
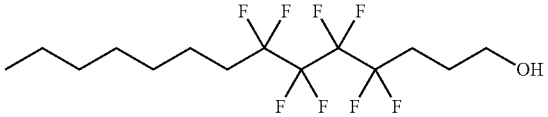
C 34.1 I
$T_{NI}$: -82.3
No. 25
No. 26
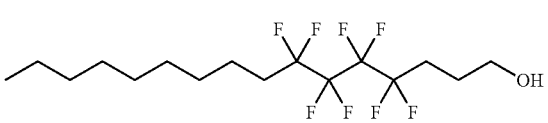
No. 27
No. 28
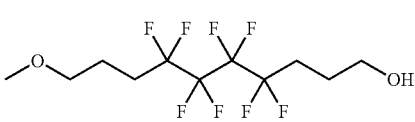
No. 29
No. 30
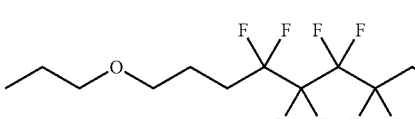
No. 31
No. 32
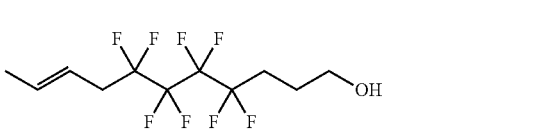
No. 33
No. 34
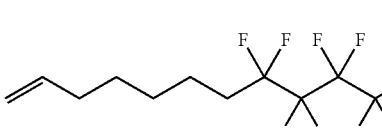
No. 35
No. 36
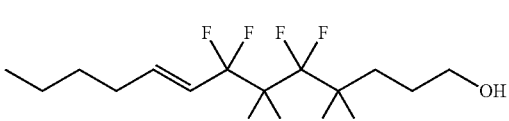

-continued
No. 37
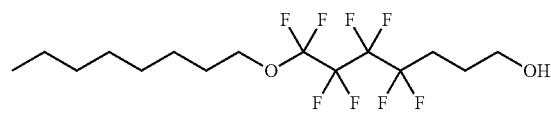
No. 38
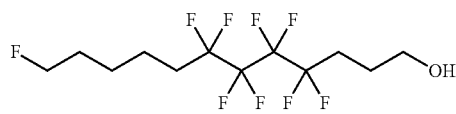
No. 39
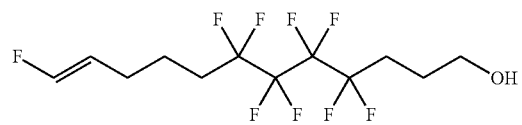
No. 40
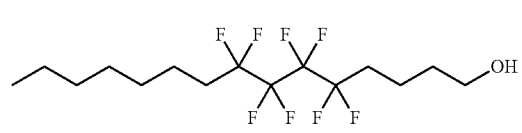
No. 41
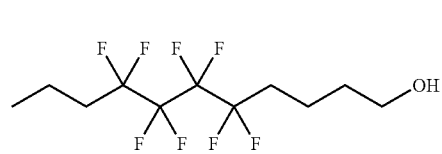
No. 42
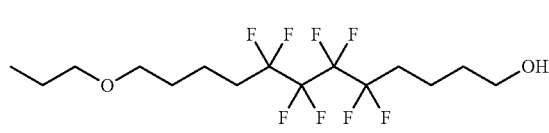
No. 43
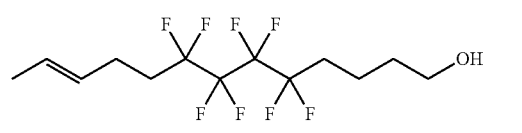
No. 44
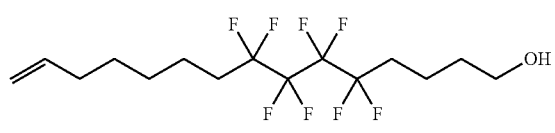
No. 45
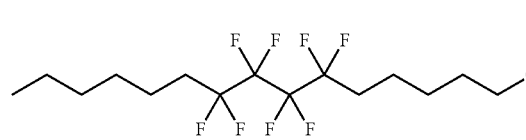
No. 46
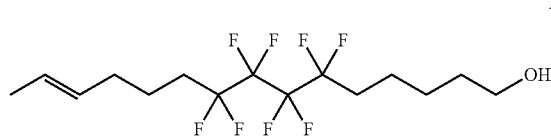
No. 47
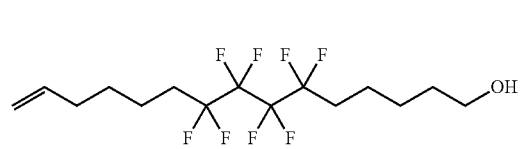
No. 48
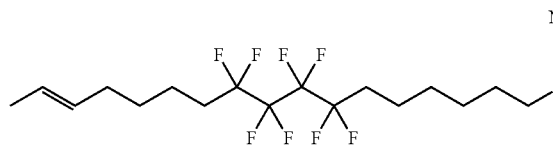
No. 49
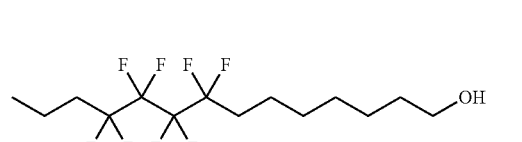
No. 50
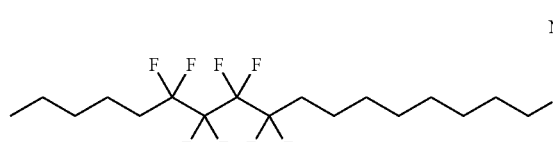
No. 51
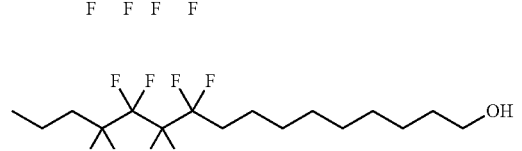
No. 52
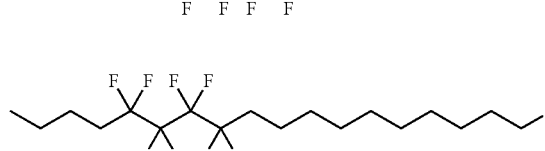
No. 53
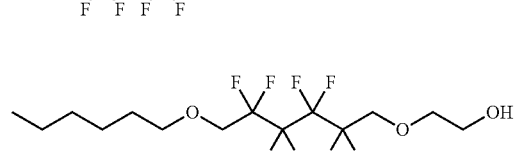
No. 54
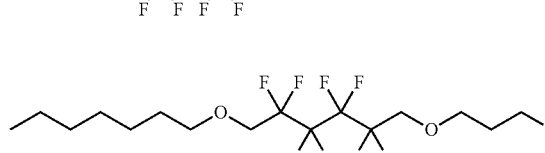
No. 55
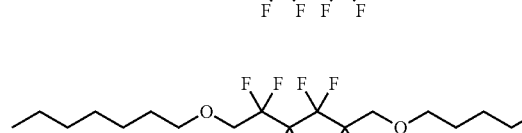
No. 56
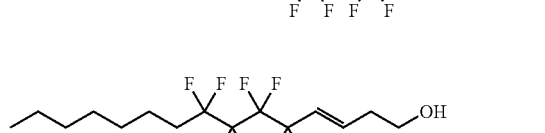
No. 57
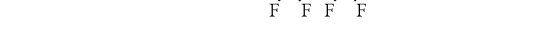
No. 58
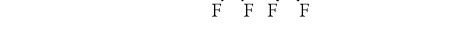

-continued

-continued
No. 79
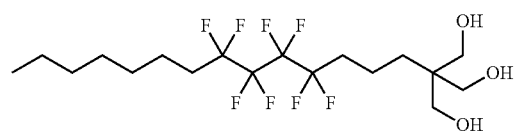
No. 80
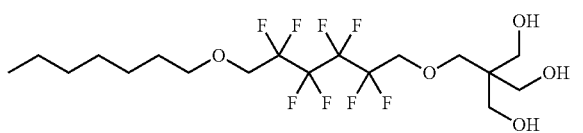
No. 81
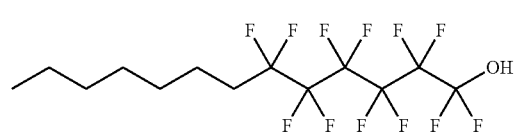
No. 82
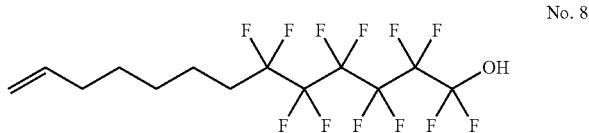
No. 83
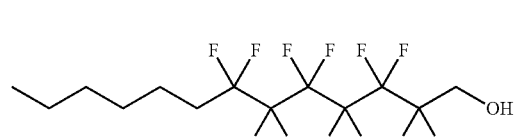
No. 84
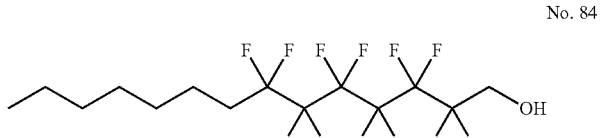
No. 85
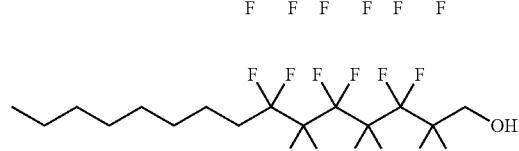
No. 86
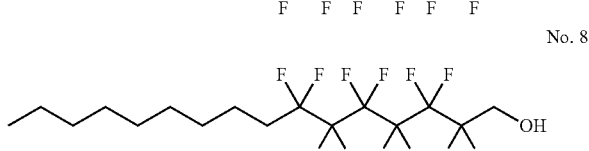
No. 87
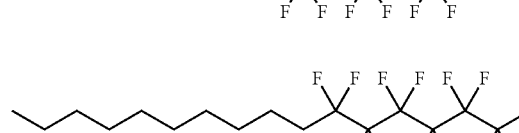
No. 88
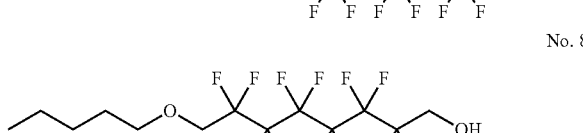
No. 89
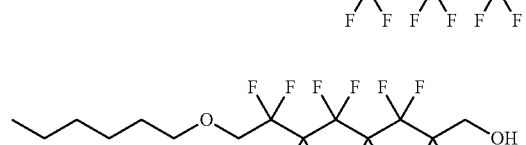
No. 90
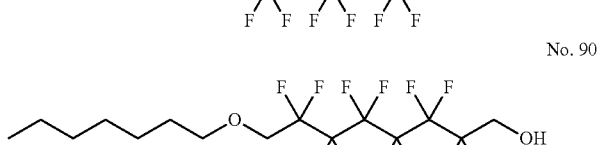
No. 91
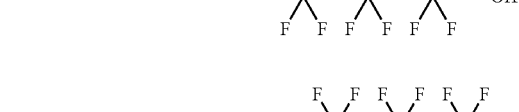
No. 92
No. 93
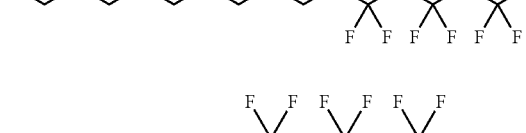
No. 94
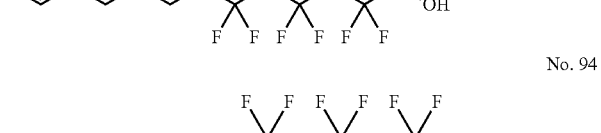
No. 95
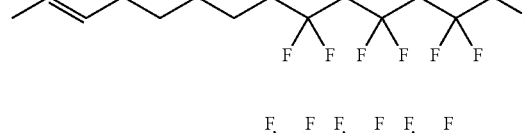
No. 96
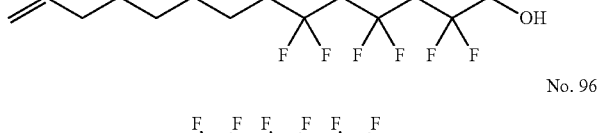
No. 97
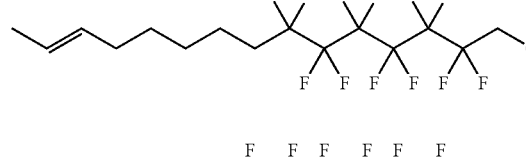
No. 98
No. 99
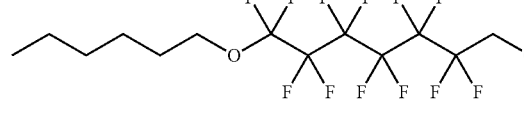
No. 100
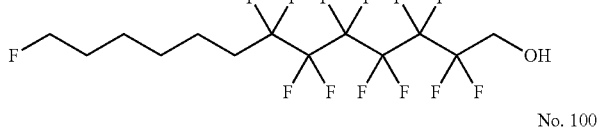
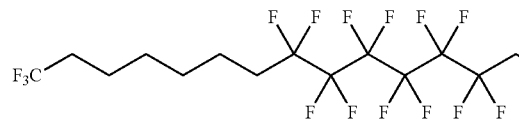
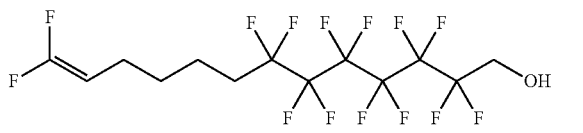

No. 101
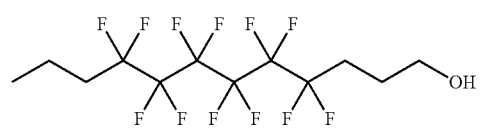
No. 102
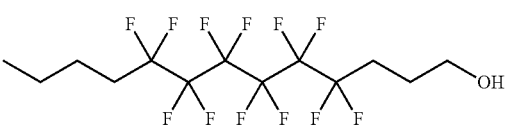
No. 103
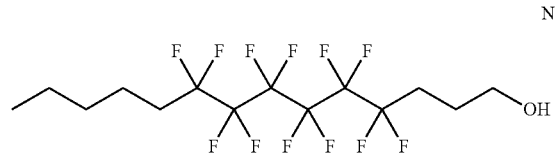
No. 104
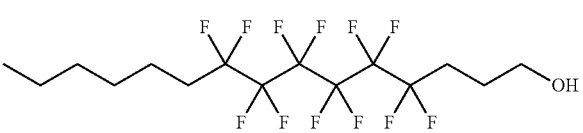
No. 105
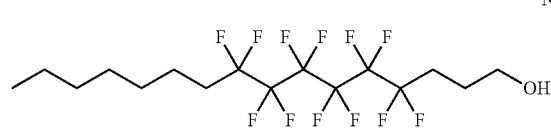
$C_1$ 40.1 $C_2$ 47.8 I
$T_{NI}$: -15.0
No. 106
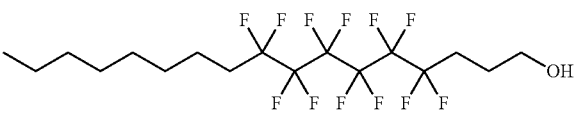
No. 107
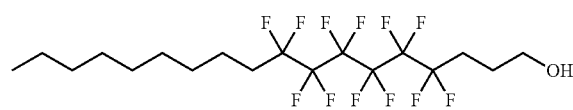
No. 108
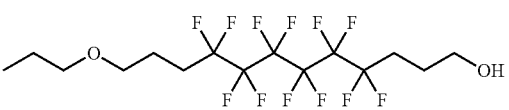
No. 109
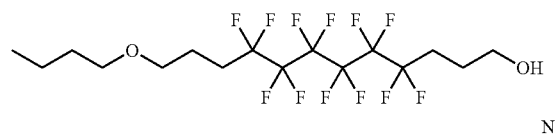
No. 110
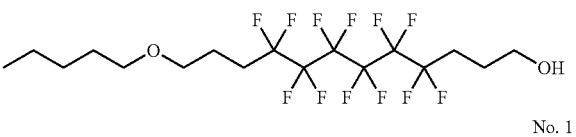
No. 111
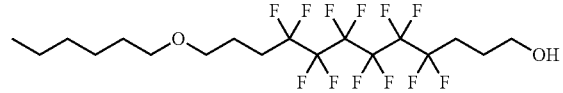
No. 112
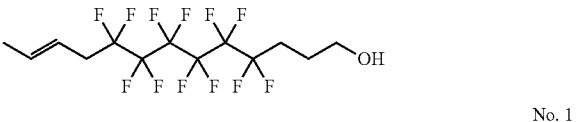
No. 113
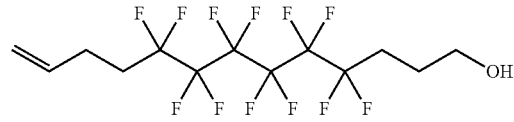
No. 114
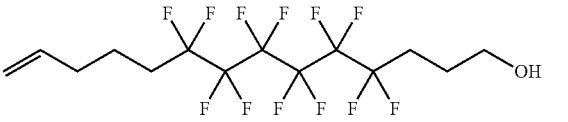
No. 115
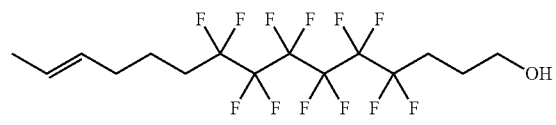
No. 116
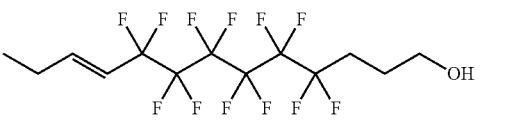
No. 117
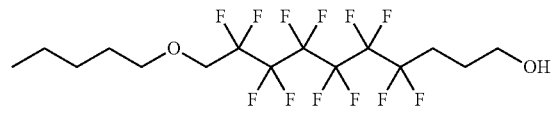
No. 118
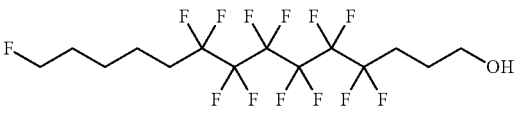
No. 119
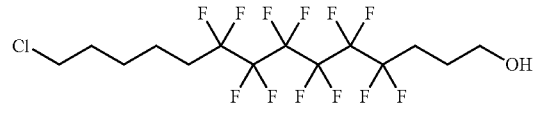
No. 120
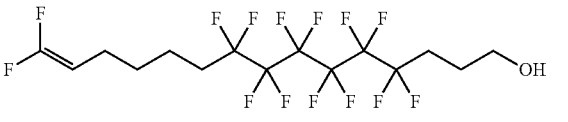
No. 121
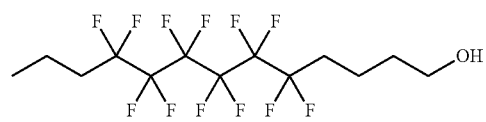
No. 122

-continued
No. 123
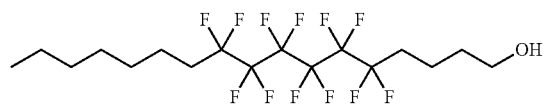
No. 124
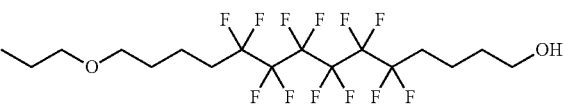
No. 125
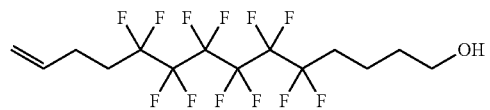
No. 126
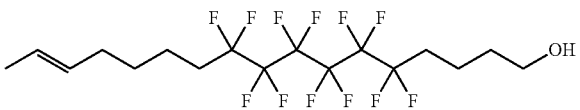
No. 127
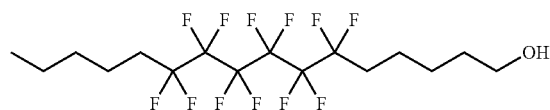
No. 128
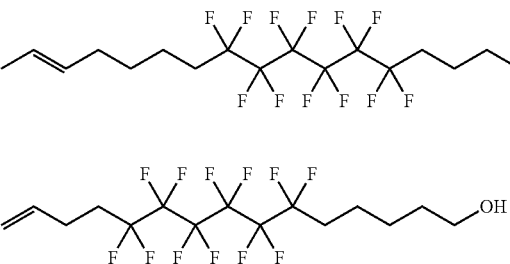
No. 129
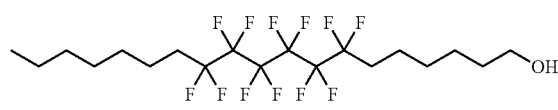
No. 130
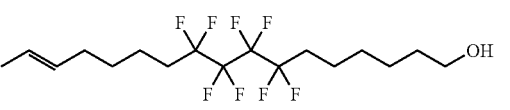
No. 131
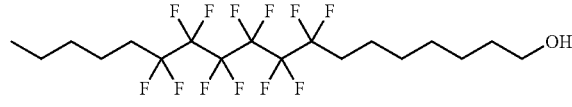
No. 132
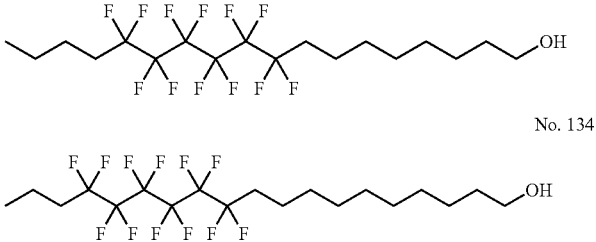
No. 133
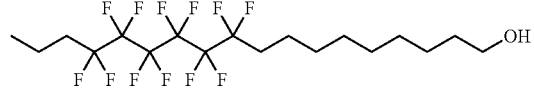
No. 134
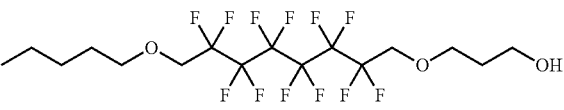
No. 135
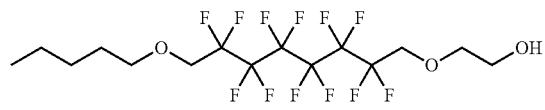
No. 136
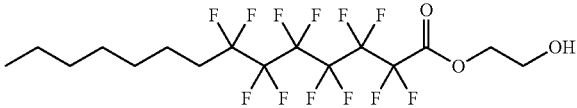
No. 137
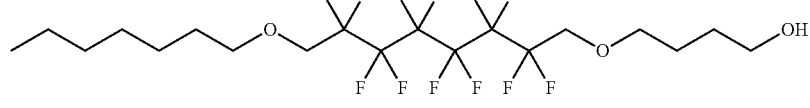
No. 138
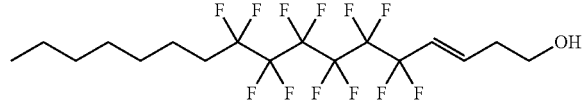
No. 139
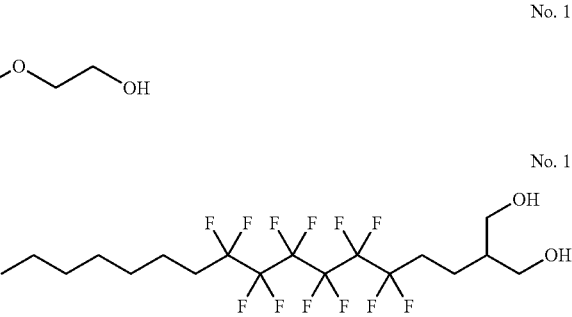
No. 140
No. 141
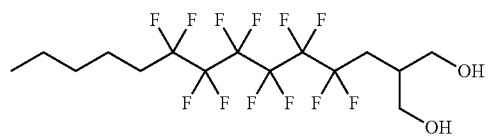
No. 142

-continued
No. 143
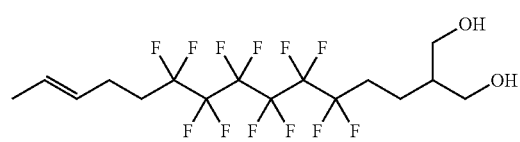
No. 144
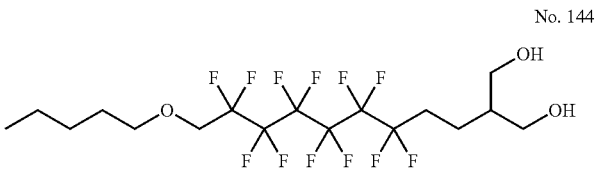
No. 145
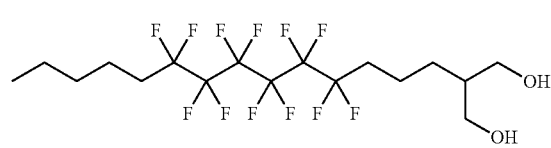
No. 146
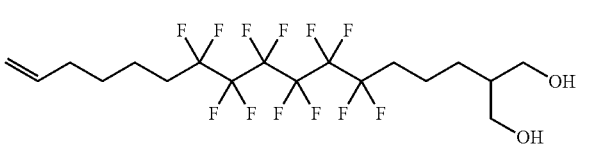
No. 147
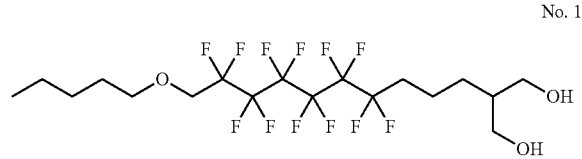
No. 148
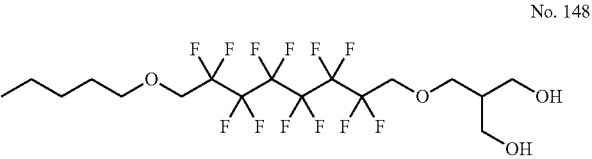
No. 149
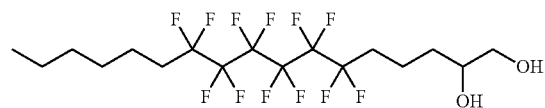
No. 150
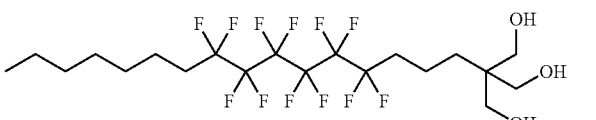
No. 151
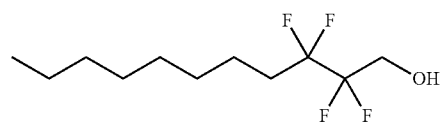
No. 152
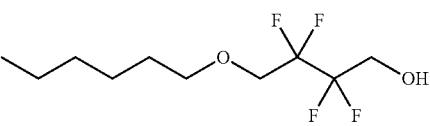
No. 153
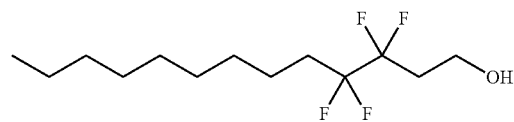
No. 154
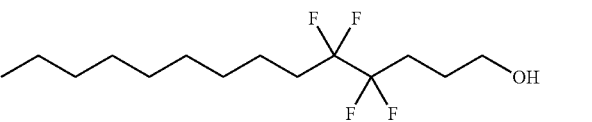
No. 155
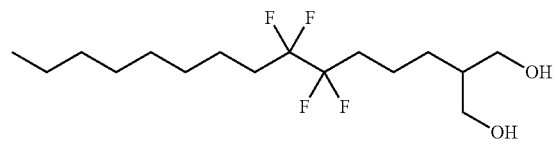
No. 156
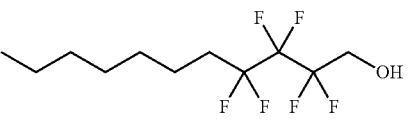
No. 157
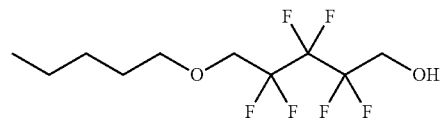
No. 158
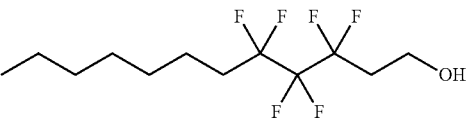
No. 159
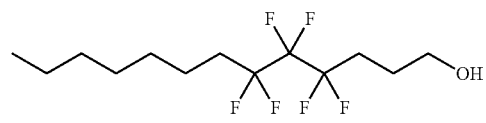
No. 160
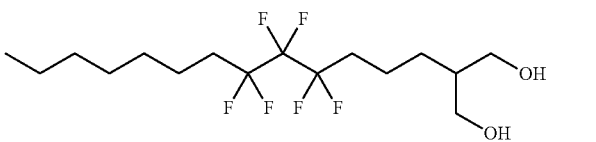
No. 161
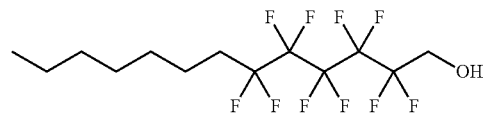
No. 162
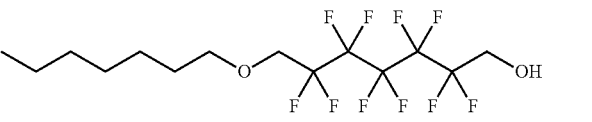

-continued
No. 163
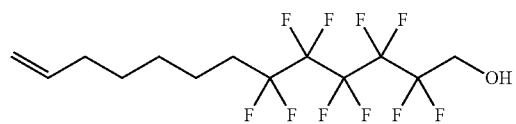
No. 164
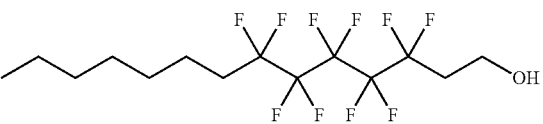
No. 165
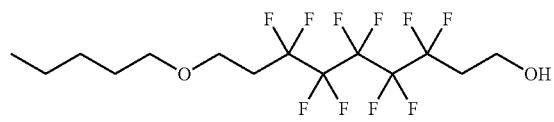
No. 166
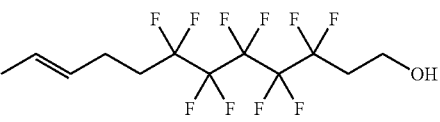
No. 167
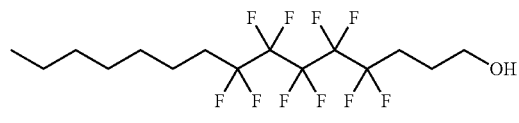
No. 168
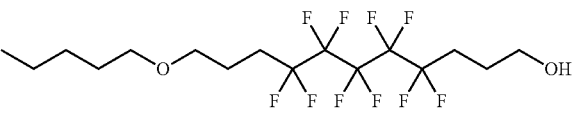
No. 169
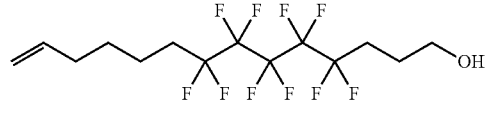
No. 170
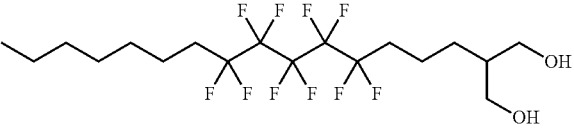
No. 171
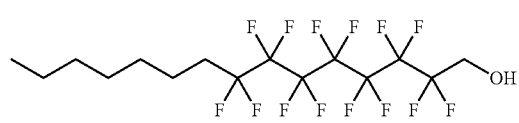
No. 172
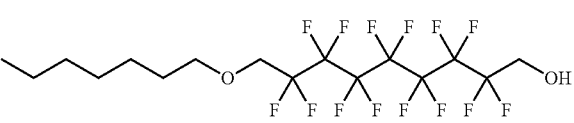
No. 173
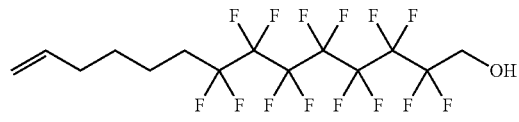
No. 174
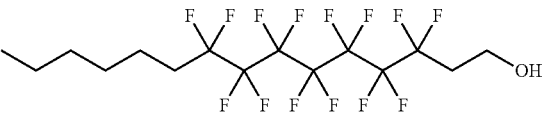
No. 175
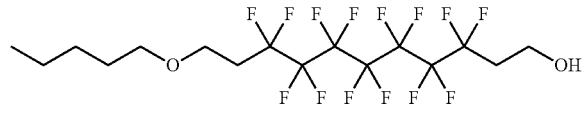
No. 176
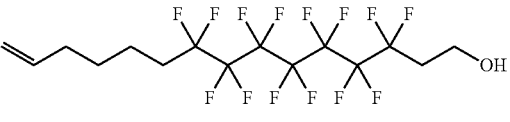
No. 177
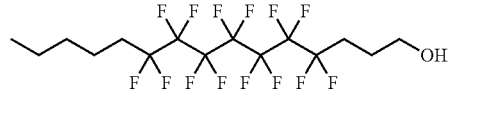
No. 178
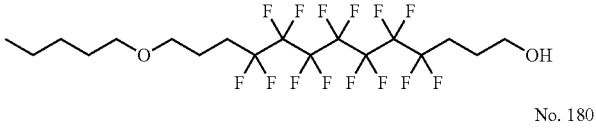
No. 179
No. 180
No. 181
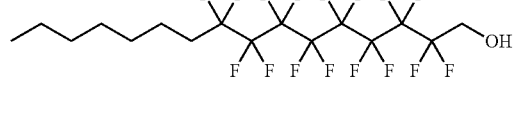
No. 182
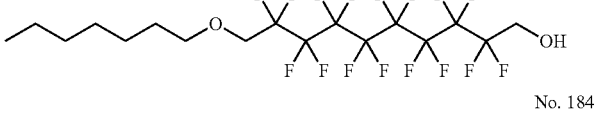
No. 183
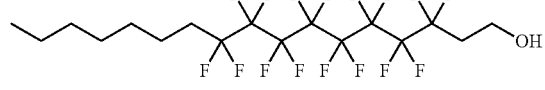
No. 184

-continued
No. 185
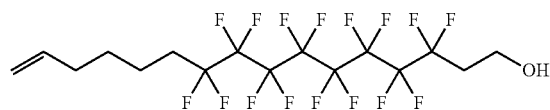
No. 186
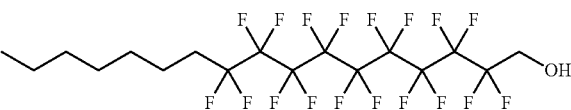
No. 187
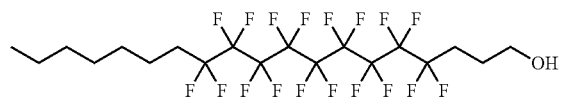
No. 188
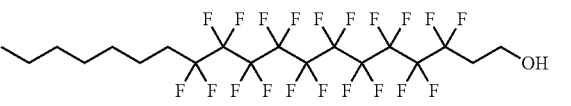
No. 189
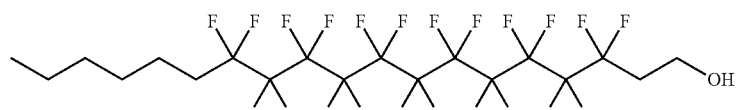
No. 190
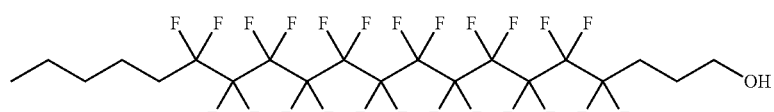
No. 191
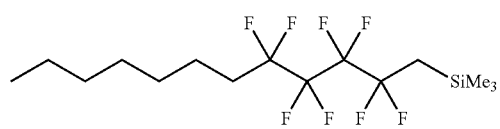
No. 192
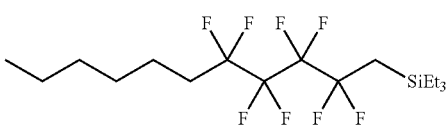
No. 193
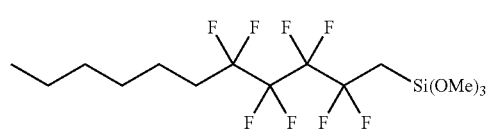
No. 194
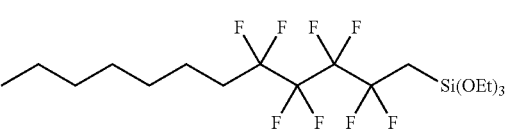
No. 195
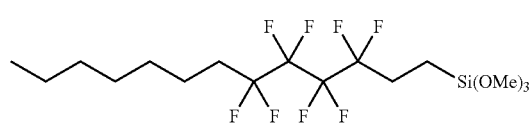
No. 196
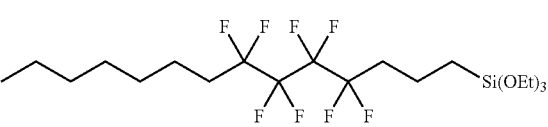
No. 197
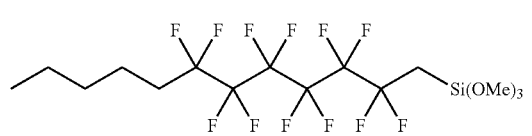
No. 198
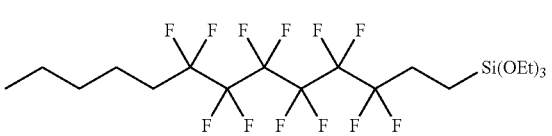
No. 199
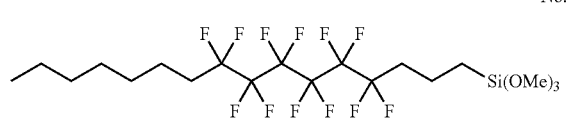
No. 200
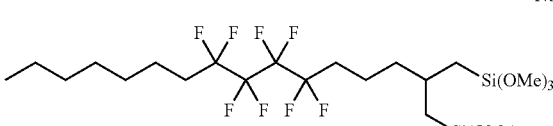
No. 201
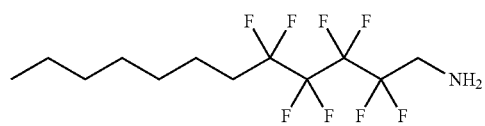
No. 202
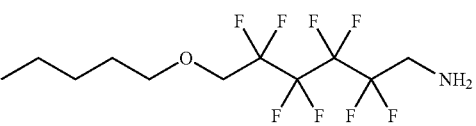
No. 203
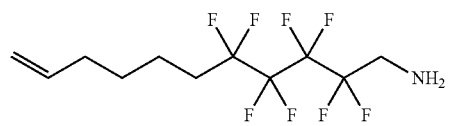
No. 204
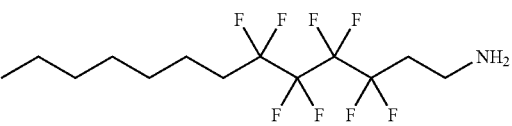

-continued

No. 205
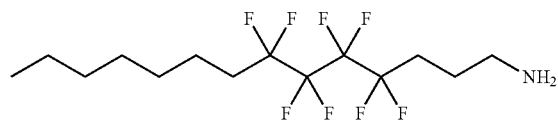

No. 206
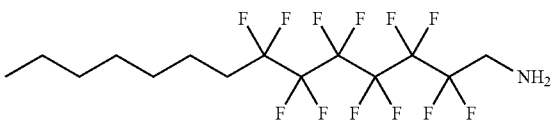

No. 207
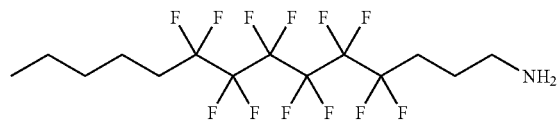

No. 208
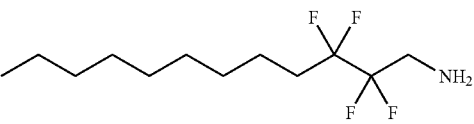

No. 209
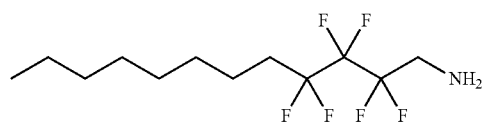

No. 210
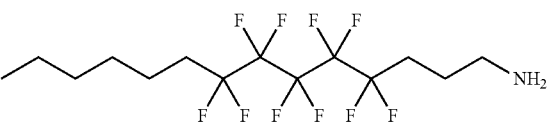

No. 211
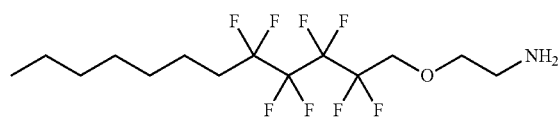

No. 212
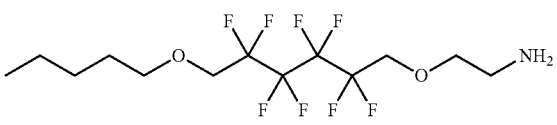

No. 213
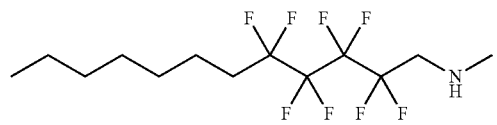

No. 214
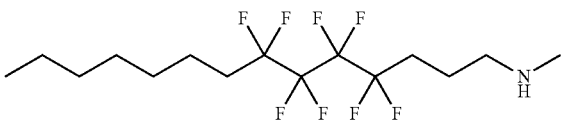

No. 215
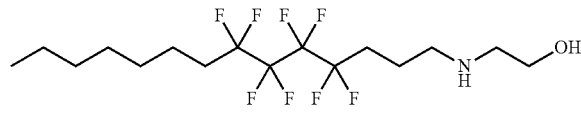

No. 216
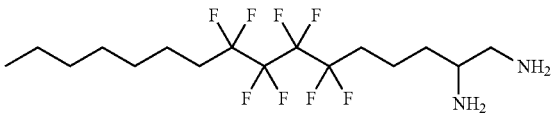

No. 217
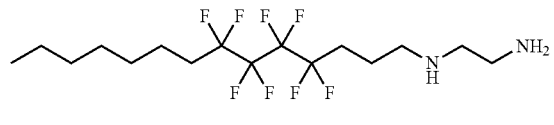

No. 218
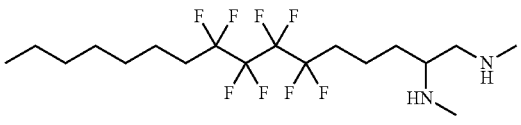

No. 219
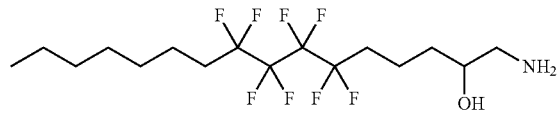

No. 220

2. Examples of Composition

The compounds described in Examples were described using symbols according to definitions in Table 3 below. In Table 3, the configuration of 1,4-cyclohexylene is trans. A parenthesized number next to a symbolized compound in Examples corresponds to the number of the compound. A symbol (-) means any other liquid crystal compound. A ratio (percentage) of the liquid crystal compound is expressed in terms of weight percent (% by weight) based on the weight of the liquid crystal composition. Values of the characteristics of the liquid crystal composition were summarized in the last part. The characteristics were measured in accordance with the methods described above, and measured values were directly described (without extrapolation).

TABLE 3

Method for Description of Compounds using Symbols
R—(A$_1$)—Z$_1$— - - - - - —Z$_n$—(A$_n$)—R'

| | Symbol |
|---|---|
| 1) Left-terminal Group R— | |
| C$_n$H$_{2n+1}$— | n- |
| C$_n$H$_{2n+1}$O— | nO— |
| C$_m$H$_{2m+1}$OC$_n$H$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | VFFn- |

TABLE 3-continued

Method for Description of Compounds using Symbols
R—(A₁)—Z₁— - - - - - —Zₙ—(Aₙ)—R'

| | Symbol |
|---|---|
| 2) Right-terminal Group —R' | |
| —CₙH₂ₙ₊₁ | -n |
| —OCₙH₂ₙ₊₁ | —On |
| —COOCH₃ | —EMe |
| —CH=CH₂ | —V |
| —CH=CH—CₙH₂ₙ₊₁ | —Vn |
| —CₙH₂ₙCH=CH₂ | -nV |
| —CₘH₂ₘ—CH=CH—CₙH₂ₙ₊₁ | -mVn |
| —CH=CF₂ | —VFF |
| —F | —F |
| —Cl | —CL |
| —OCF₃ | —OCF₃ |
| —OCF₂H | —OCF₂H |
| —CF₃ | —CF₃ |
| —OCH=CH—CF₃ | —OVCF₃ |
| —C≡N | —C |
| 3) Bonding Group —Zₙ— | |
| —CₙH₂ₙ— | n |
| —COO— | E |
| —CH=CH— | V |
| —CH₂O— | 1O |
| —OCH₂— | O1 |
| —CF₂O— | X |
| —C≡C— | T |
| 4) Ring Structure —Aₙ— | |
|  | H |
|  | B |
| 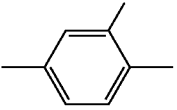 | B(F) |
| 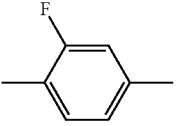 | B(2F) |
| 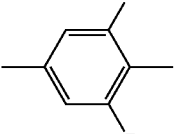 | B(F,F) |
| 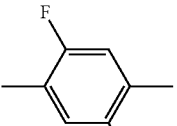 | B(2F,5F) |
| 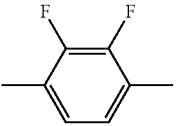 | B(2F,3F) |

TABLE 3-continued

Method for Description of Compounds using Symbols
R—(A₁)—Z₁— - - - - - —Zₙ—(Aₙ)—R'

| | Symbol |
|---|---|
| 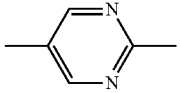 | Py |
| 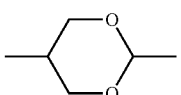 | G |
| 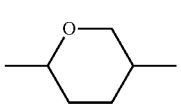 | Dh |
| 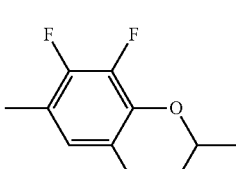 | Cro |
| 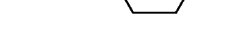 | B(2F,3CL) |

5) Examples of Description

Example 1. 3-HH—V

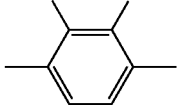

Example 2. 3-BB(F,F)XB(F,F)—F

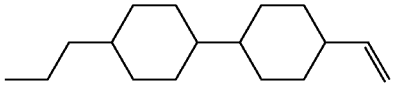 [SMILES: C=CC1CCC(C2CCC(CCC)CC2)CC1]

Example 3. 3-HH-4

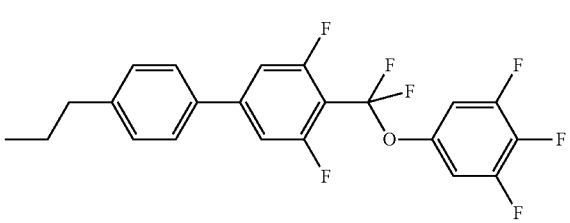 [SMILES: CCCc1ccc(-c2cc(F)c(C(F)(F)Oc3cc(F)c(F)c(F)c3)c(F)c2)cc1]

TABLE 3-continued

| Method for Description of Compounds using Symbols |
|---|
| R—(A₁)—Z₁— · · · · · —Zₙ—(Aₙ)—R' |

| | Symbol |
|---|---|
| Example 4. 3-HBB(2F,3F)—O2 | |

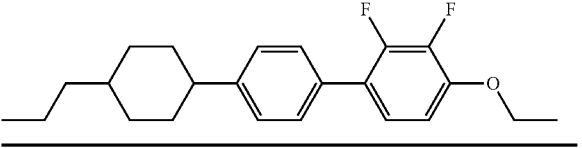

Use Example 1

| 3-HB-O2 | (2-5) | 13% |
|---|---|---|
| 5-HB-CL | (5-2) | 10% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 10% |
| 5-PyBB-F | (6-80) | 10% |
| 5-HBB(F)B-2 | (4-5) | 10% |
| 5-HBB(F)B-3 | (4-5) | 10% |

To a composition described above, compound (No. 24) described below was added at a ratio of 3% by weight.

(No. 24)

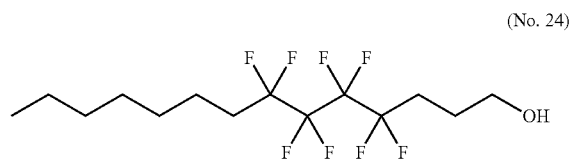 [SMILES: CCCCCCCC(F)(F)C(F)(F)C(F)(F)C(F)(F)CCCO]

NI=100.0° C.; η=39.6 mPa·s; Δn=0.191; Δε=7.9.

Use Example 2

| 7-HB(F,F)-F | (5-4) | 3% |
|---|---|---|
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 10% |
| 3-HBB(F)-F | (6-23) | 10% |
| 5-HBB(F)-F | (6-23) | 14% |
| 2-HBB-F | (6-22) | 4% |
| 3-HBB-F | (6-22) | 4% |
| 5-HBB-F | (6-22) | 3% |
| 3-HBB(F,F)-F | (6-24) | 5% |
| 5-HBB(F,F)-F | (6-24) | 10% |

To the composition described above, compound (No. 105) described below was added at a ratio of 3% by weight.

(No. 105)

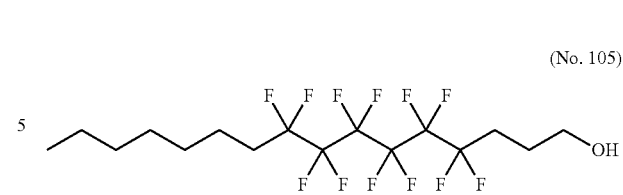

NI=84.8° C.; η=25.0 mPa·s; Δn=0.115; Δε=5.8.

Use Example 3

| 2-HB-C | (8-1) | 7% |
|---|---|---|
| 3-HB-C | (8-1) | 10% |
| 3-HB-O2 | (2-5) | 15% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

To the composition described above, compound (No. 10) described below was added at a ratio of 1% by weight.

(No. 10)

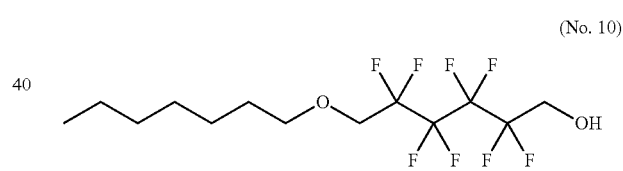

NI=99.7° C.; η=17.9 mPa·s; Δn=0.099; Δε=4.6.

Use Example 4

| 3-HB-CL | (5-2) | 5% |
|---|---|---|
| 5-HB-CL | (5-2) | 3% |
| 3-HHB-OCF3 | (6-1) | 5% |
| 3-H2HB-OCF3 | (6-13) | 5% |
| 5-H4HB-OCF3 | (6-19) | 15% |
| V-HHB(F)-F | (6-2) | 5% |
| 3-HHB(F)-F | (6-2) | 6% |
| 5-HHB(F)-F | (6-2) | 6% |
| 3-H4HB(F,F)-CF3 | (6-21) | 8% |
| 5-H4HB(F,F)-CF3 | (6-21) | 10% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 10% |
| 3-HBEB(F,F)-F | (6-39) | 5% |

To the composition described above, compound (No. 90) described below was added at a ratio of 3% by weight.

(No. 90)

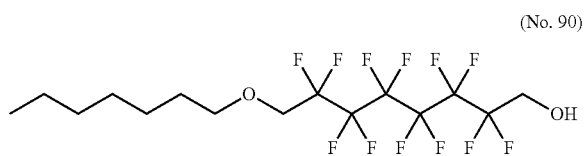 [SMILES: CCCCCCCOCC(F)(F)C(F)(F)C(F)(F)C(F)(F)C(F)(F)C(F)(F)CO]

NI=72.2° C.; η=26.0 mPa·s; Δn=0.097; Δ∈=8.3.

Use Example 5

| 5-HB-CL | (5-2) | 16% |
| 3-HH-4 | (2-1) | 12% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 9% |
| 5-HHB(F)-F | (6-2) | 9% |
| 7-HHB(F)-F | (6-2) | 8% |
| 5-HBB(F)-F | (6-23) | 4% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

To the composition described above, compound (No. 68) described below was added at a ratio of 1% by weight.

(No. 68)

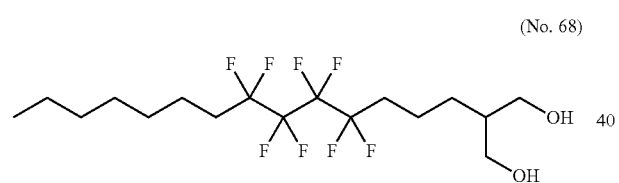

NI=115.0° C.; =19.4 mPa·s; Δn=0.091; Δ∈=3.8.

Use Example 6

| 5-HB-F | (5-2) | 12% |
| 6-HB-F | (5-2) | 9% |
| 7-HB-F | (5-2) | 7% |
| 2-HHB-OCF3 | (6-1) | 7% |
| 3-HHB-OCF3 | (6-1) | 7% |
| 4-HHB-OCF3 | (6-1) | 7% |
| 5-HHB-OCF3 | (6-1) | 5% |
| 3-HH2B-OCF3 | (6-4) | 4% |
| 5-HH2B-OCF3 | (6-4) | 4% |
| 3-HHB(F,F)-OCF2H | (6-3) | 4% |
| 3-HHB(F,F)-OCF3 | (6-3) | 7% |
| 3-HH2B(F)-F | (6-5) | 3% |
| 3-HBB(F)-F | (6-23) | 8% |
| 5-HBB(F)-F | (6-23) | 10% |
| 5-HBBH-3 | (4-1) | 3% |
| 3-HB(F)BH-3 | (4-2) | 3% |

To the composition described above, compound (No. 84) described below was added at a ratio of 1% by weight.

(No. 84)

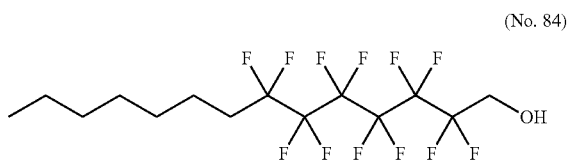 [SMILES: CCCCCCCC(F)(F)C(F)(F)C(F)(F)C(F)(F)C(F)(F)C(F)(F)CO]

NI=85.1° C.; η=15.1 mPa·s; Δn=0.091; Δ∈=4.6.

Use Example 7

| 3-HHB(F,F)-F | (6-3) | 10% |
| 3-H2HB(F,F)-F | (6-15) | 8% |
| 4-H2HB(F,F)-F | (6-15) | 8% |
| 5-H2HB(F,F)-F | (6-15) | 8% |
| 3-HBB(F,F)-F | (6-24) | 20% |
| 5-HBB(F,F)-F | (6-24) | 20% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 4% |

To the composition described above, compound (No. 33) described below was added at a ratio of 1% by weight.

(No. 33)

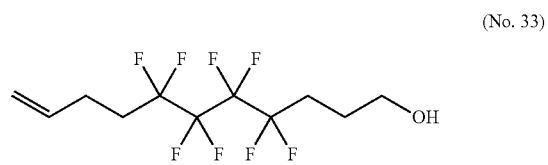 [SMILES: C=CCCC(F)(F)C(F)(F)C(F)(F)C(F)(F)CCCO]

NI=98.1° C.; η=34.9 mPa·s; Δn=0.116; Δ∈=9.0.

Use Example 8

| 3-HH-V1 | (2-1) | 12% |
| 3-HHEH-5 | (3-13) | 3% |
| V2-BB(F)B-1 | (3-6) | 3% |
| 1V2-BB-F | (5-1) | 3% |
| 5-HB-CL | (5-2) | 16% |
| 3-HH-5 | (2-1) | 4% |
| 3-HHB-F | (6-1) | 4% |
| 4-HHB-CL | (6-1) | 4% |
| 3-HHB(F)-F | (6-2) | 10% |
| 4-HHB(F)-F | (6-2) | 6% |
| 5-HHB(F)-F | (6-2) | 9% |
| 7-HHB(F)-F | (6-2) | 5% |
| 5-HBB(F)-F | (6-23) | 4% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

To the composition described above, compound (No. 24) described below was added at a ratio of 1% by weight.

(No. 24)

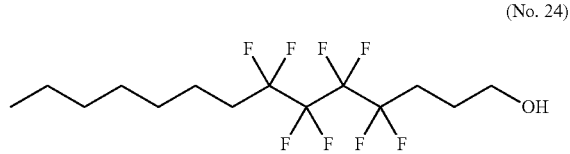 [SMILES: CCCCCCCC(F)(F)C(F)(F)C(F)(F)C(F)(F)CCCO]

Further, compound (16-1-1-1) described below was added at a ratio of 0.3% by weight.

(16-1-1-1)

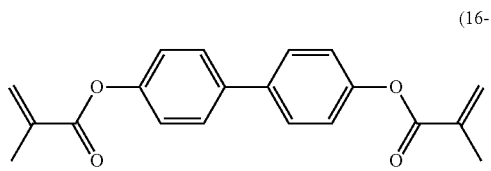

NI=114.3° C.; η=18.2 mPa·s; Δn=0.100; Δ∈=3.7.

Use Example 9

| 2-HH-3 | (2-1) | 3% |
| 5-HB-CL | (5-2) | 11% |
| 3-HH-4 | (2-1) | 4% |
| 3-HHB-1 | (3-1) | 6% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |

To the composition described above, compound (No. 105) described below was added at a ratio of 0.5% by weight.

(No. 105)

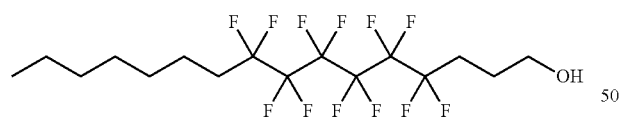

Further, compound (16-1-1-2) described below was added at a ratio of 0.3% by weight.

(16-1-1-2)

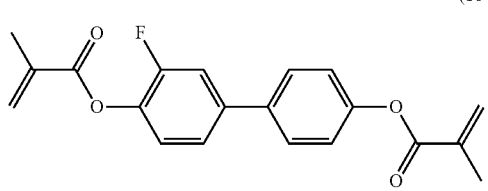

NI=80.1° C.; η=22.3 mPa·s; Δn=0.103; Δ∈=8.7.

Use Example 10

| 5-HB-CL | (5-2) | 3% |
| 7-HB(F)-F | (5-3) | 7% |
| 3-HH-4 | (2-1) | 10% |
| 3-HH-EMe | (2-2) | 22% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 7% |

To the composition described above, compound (No. 10) described below was added at a ratio of 0.5% by weight.

(No. 10)

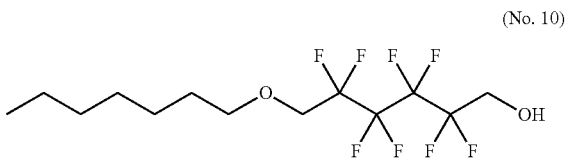 [SMILES: CCCCCCCOCC(F)(F)C(F)(F)C(F)(F)C(F)(F)CO]

Further, compound (16-1-1-1) described below was added at a ratio of 0.3% by weight.

(16-1-1-1)

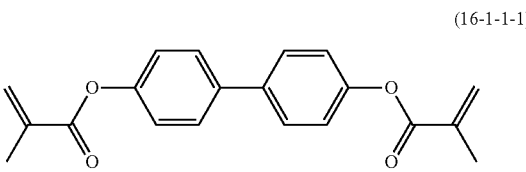

NI=79.3° C.; η=19.7 mPa·s; Δn=0.064; Δ∈=5.7.

Use Example 11

| 5-HB-CL | (5-2) | 17% |
| 7-HB(F,F)-F | (5-4) | 3% |
| 3-HH-4 | (2-1) | 10% |
| 3-HH-5 | (2-1) | 5% |
| 3-HB-O2 | (2-5) | 15% |
| 3-HHB-1 | (3-1) | 8% |
| 3-HHB-O1 | (3-1) | 5% |
| 2-HHB(F)-F | (6-2) | 6% |
| 3-HHB(F)-F | (6-2) | 9% |
| 5-HHB(F)-F | (6-2) | 6% |
| 3-HHB(F,F)-F | (6-3) | 6% |
| 3-H2HB(F,F)-F | (6-15) | 5% |
| 4-H2HB(F,F)-F | (6-15) | 5% |

To the composition described above, compound (No. 90) described below was added at a ratio of 1% by weight.

(No. 90)

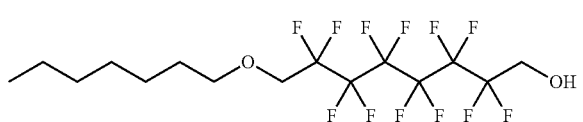

Further, compounds (16-1-1-1) and (16-1-1-2) described below were added at a ratio of 0.15% by weight, respectively.

(16-1-1-1)

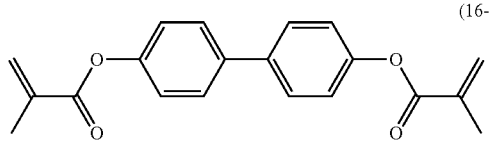

(16-1-1-2)

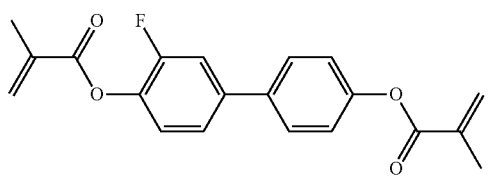

NI=71.2° C.; η=13.5 mPa·s; Δn=0.074; Δ∈=2.8.

Use Example 12

| | | |
|---|---|---|
| 1V2-BEB(F,F)-C | (8-15) | 6% |
| 3-HB-C | (8-1) | 18% |
| 2-BTB-1 | (2-10) | 10% |
| 5-HH-VFF | (2-1) | 30% |
| 3-HHB-1 | (3-1) | 4% |
| VFF-HHB-1 | (3-1) | 7% |
| VFF2-HHB-1 | (3-1) | 11% |
| 3-H2BTB-2 | (3-17) | 6% |
| 3-H2BTB-3 | (3-17) | 4% |
| 3-H2BTB-4 | (3-17) | 4% |

To the composition described above, compound (No. 24) described below was added at a ratio of 1% by weight.

(No. 24)

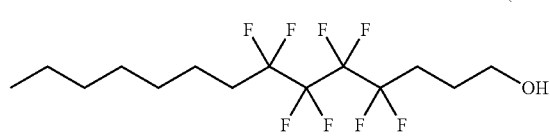

Further, compound (16-1-1-2) described below was added at a ratio of 0.3% by weight.

(16-1-1-2)

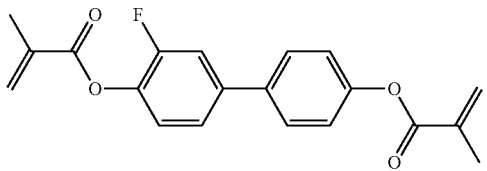

NI=81.6° C.; η=11.7 mPa·s; Δn=0.131; Δ∈=6.5.

Use Example 13

| | | |
|---|---|---|
| 1V2-BEB(F,F)-C | (8-15) | 6% |
| 3-HB-C | (8-1) | 18% |
| 2-BTB-1 | (2-10) | 10% |
| 5-HH-VFF | (2-1) | 30% |
| 3-HHB-1 | (3-1) | 4% |
| VFF-HHB-1 | (3-1) | 7% |
| VFF2-HHB-1 | (3-1) | 11% |
| 3-H2BTB-2 | (3-17) | 6% |
| 3-H2BTB-3 | (3-17) | 4% |
| 3-H2BTB-4 | (3-17) | 4% |

To the composition described above, compound (No. 105) described below was added at a ratio of 3% by weight.

(No. 105)

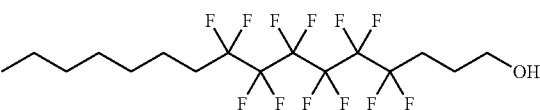

Further, compound (16-1-1-1) described below was added at a ratio of 0.3% by weight.

(16-1-1-1)

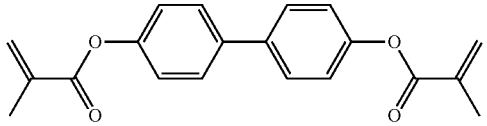

NI=81.6° C.; η=11.7 mPa·s; Δn=0.131; Δ∈=6.5.

Use Example 14

| | | |
|---|---|---|
| 1-BB-3 | (2-8) | 10% |
| 3-HH-V | (2-1) | 29% |
| 3-BB(2F,3F)-O2 | (9-3) | 13% |
| 2-HH1OB(2F,3F)-O2 | (10-5) | 20% |
| 3-HH1OB(2F,3F)-O2 | (10-5) | 14% |
| 3-HHB-1 | (3-1) | 8% |
| 5-B(F)BB-2 | (3-8) | 4% |
| 2-BB(2F,3F)B-3 | (11-1) | 2% |

To the composition described above, compound (No. 24) described below was added at a ratio of 3% by weight.

(No. 24)

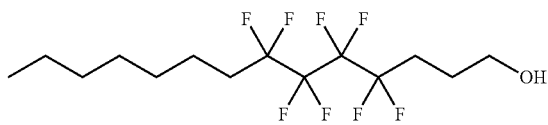

NI=74.0° C.; η=14.8 mPa·s; Δn=0.105; Δ∈=−3.0.

Use Example 15

| 3-HB-O1 | (2-5) | 15% |
| 3-HH-4 | (2-1) | 5% |
| 3-HB(2F,3F)-O2 | (9-1) | 12% |
| 5-HB(2F,3F)-O2 | (9-1) | 12% |
| 2-HHB(2F,3F)-1 | (10-1) | 12% |
| 3-HHB(2F,3F)-1 | (10-1) | 12% |
| 3-HHB(2F,3F)-O2 | (10-1) | 12% |
| 5-HHB(2F,3F)-O2 | (10-1) | 13% |
| 3-HHB-1 | (3-1) | 7% |

To the composition described above, compound (No. 105) described below was added at a ratio of 5% by weight.

(No. 105)

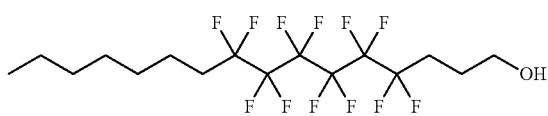

NI=86.5° C.; η=35.0 mPa·s; Δn=0.090; Δ∈=−3.3.

Use Example 16

| 2-HH-3 | (2-1) | 16% |
| 1-BB-3 | (2-8) | 2% |
| 7-HB-1 | (2-5) | 8% |
| 5-HB-O2 | (2-5) | 8% |
| 3-HB(2F,3F)-O2 | (9-1) | 17% |
| 5-HB(2F,3F)-O2 | (9-1) | 16% |
| 3-HHB(2F,3CL)-O2 | (10-12) | 3% |
| 4-HHB(2F,3CL)-O2 | (10-12) | 3% |
| 5-HHB(2F,3CL)-O2 | (10-12) | 2% |
| 3-HH1OCro(7F,8F)-5 | (13-6) | 5% |
| 5-HBB(F)B-2 | (4-5) | 10% |
| 5-HBB(F)B-3 | (4-5) | 10% |

To the composition described above, compound (No. 10) described below was added at a ratio of 3% by weight.

(No. 10)

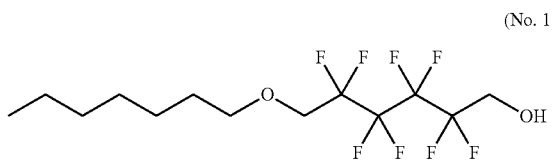

NI=75.9° C.; η=22.9 mPa·s; Δn=0.106; Δ∈=−2.5.

Use Example 17

| 3-HB-O1 | (2-5) | 15% |
| 3-HH-4 | (2-1) | 5% |
| 3-HB(2F,3F)-O2 | (9-1) | 12% |
| 5-HB(2F,3F)-O2 | (9-1) | 12% |
| 2-HHB(2F,3F)-1 | (10-1) | 12% |
| 3-HHB(2F,3F)-1 | (10-1) | 12% |
| 3-HHB(2F,3F)-O2 | (10-1) | 14% |
| 5-HHB(2F,3F)-O2 | (10-1) | 12% |
| 6-HEB(2F,3F)-O2 | (9-6) | 6% |

To the composition described above, compound (No. 90) described below was added at a ratio of 5% by weight.

(No. 90)

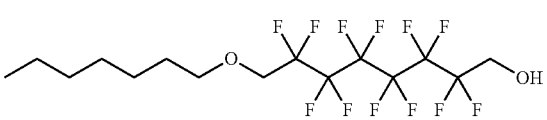

Further, compound (16-1-1-1) described below was added at a ratio of 0.3% by weight.

(16-1-1-1)

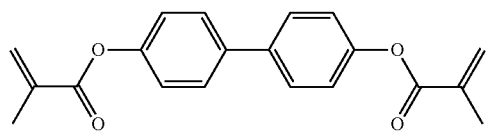

NI=81.7° C.; η=34.2 mPa·s; Δn=0.087; Δ∈=−3.7.

Use Example 18

| 2-HH-5 | (2-1) | 3% |
| 3-HH-4 | (2-1) | 15% |
| 3-HH-5 | (2-1) | 4% |
| 3-HB-O2 | (2-5) | 8% |
| 5-HB-O2 | (2-5) | 4% |
| 3-H2B(2F,3F)-O2 | (9-4) | 15% |
| 5-H2B(2F,3F)-O2 | (9-4) | 15% |
| 3-HHB(2F,3CL)-O2 | (10-12) | 5% |
| 2-HBB(2F,3F)-O2 | (10-7) | 3% |
| 3-HBB(2F,3F)-O2 | (10-7) | 9% |
| 5-HBB(2F,3F)-O2 | (10-7) | 9% |
| 3-HHB-1 | (3-1) | 3% |
| 3-HHB-3 | (3-1) | 4% |
| 3-HHB-O1 | (3-1) | 3% |

To the composition described above, compound (No. 68) described below was added at a ratio of 0.5% by weight.

(No. 68)

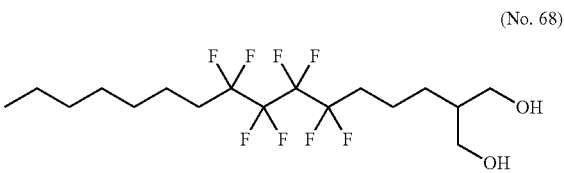 [SMILES: CCCCCCCC(F)(F)C(F)(F)C(F)(F)C(F)(F)CCCC(CO)CO]

Further, compound (16-1-1-2) described below was added at a ratio of 0.3% by weight.

(16-1-1-2)

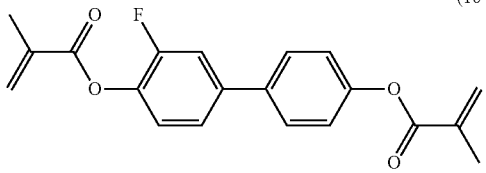

NI=76.2° C.; η=19.4 mPa·s; Δn=0.093; Δ∈=−4.0.

Use Example 19

| 2-HH-3 | (2-1) | 21% |
|---|---|---|
| 3-HH-4 | (2-1) | 9% |
| 1-BB-3 | (2-8) | 9% |
| 5-HB-O2 | (2-5) | 2% |
| 3-BB(2F,3F)-O2 | (9-3) | 9% |
| 5-BB(2F,3F)-O2 | (9-3) | 6% |
| 2-HH1OB(2F,3F)-O2 | (10-5) | 13% |
| 3-HH1OB(2F,3F)-O2 | (10-5) | 21% |
| 3-HHB-1 | (3-1) | 5% |
| 3-HHB-O1 | (3-1) | 3% |
| 5-B(F)BB-2 | (3-8) | 2% |

To the composition described above, compound (No. 84) described below was added at a ratio of 1% by weight.

(No. 84)

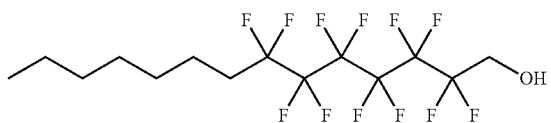

Further, compound (16-1-1-1) described below was added at a ratio of 0.3% by weight.

(16-1-1-1)

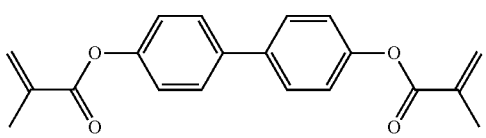

NI=74.6° C.; n=15.4 mPa·s; Δn=0.097; Δ∈=−3.2.

Use Example 20

| 2-HH-3 | (2-1) | 6% |
|---|---|---|
| 3-HH-V1 | (2-1) | 10% |
| 1V2-HH-1 | (2-1) | 8% |
| 1V2-HH-3 | (2-1) | 7% |
| 3-BB(2F,3F)-O2 | (9-3) | 8% |
| 5-BB(2F,3F)-O2 | (9-3) | 4% |
| 3-H1OB(2F,3F)-O2 | (9-5) | 7% |
| 2-HH1OB(2F,3F)-O2 | (10-5) | 7% |
| 3-HH1OB(2F,3F)-O2 | (10-5) | 20% |
| 3-HDhB(2F,3F)-O2 | (10-3) | 7% |
| 3-HHB-1 | (3-1) | 3% |
| 3-HHB-3 | (3-1) | 2% |
| 2-BB(2F,3F)B-3 | (11-1) | 11% |

To the composition described above, compound (No. 33) described below was added at a ratio of 3% by weight.

(No. 33)

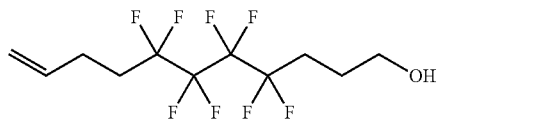

Further, compounds (16-1-1-1) and (16-1-1-2) described below were added at a ratio of 0.15% by weight, respectively.

(16-1-1-1)

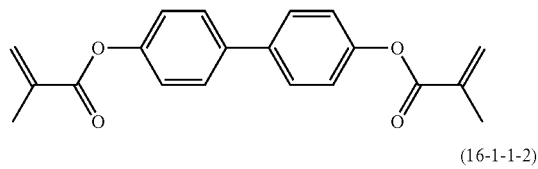

(16-1-1-2)

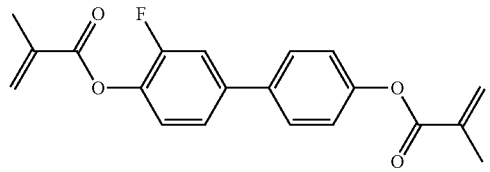

NI=85.1° C.; η=21.3 mPa·s; Δn=0.108; Δ∈=−4.4.

Use Example 21

| 3-HH-4 | (2-1) | 8% |
|---|---|---|
| 3-H2B(2F,3F)-O2 | (9-4) | 22% |
| 5-H2B(2F,3F)-O2 | (9-4) | 22% |
| 2-HHB(2F,3CL)-O2 | (10-12) | 2% |
| 3-HHB(2F,3CL)-O2 | (10-12) | 3% |
| 4-HHB(2F,3CL)-O2 | (10-12) | 2% |
| 5-HHB(2F,3CL)-O2 | (10-12) | 2% |
| 3-HBB(2F,3F)-O2 | (10-7) | 9% |
| 5-HBB(2F,3F)-O2 | (10-7) | 9% |
| V-HHB-1 | (3-1) | 5% |
| 3-HHB-3 | (3-1) | 7% |
| 3-HHEBH-3 | (4-6) | 3% |
| 3-HHEBH-4 | (4-6) | 3% |
| 3-HHEBH-5 | (4-6) | 3% |

To the composition described above, compound (No. 24) described below was added at a ratio of 3% by weight.

(No. 24)

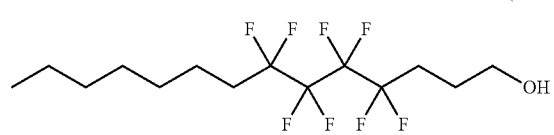

Further, compound (16-1-1-2) described below was added at a ratio of 0.3% by weight.

(16-1-1-2)

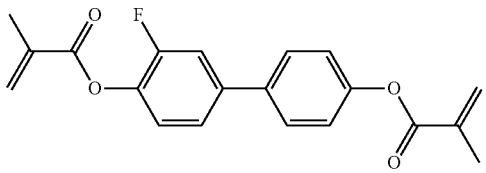

NI=91.6° C.; η=29.3 mPa·s; Δn=0.100; Δ∈=−4.1.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

Compound (1) has a high chemical stability, a high ability to align liquid crystal molecules and a high solubility in a liquid crystal composition, and causes no decrease of liquid crystallinity of the liquid crystal composition. A liquid crystal composition containing compound (1) satisfies at least one of characteristics such as a high maximum temperature, a low minimum temperature, a small viscosity, a suitable optical anisotropy, a large positive or negative dielectric anisotropy, a large specific resistance, a high stability to ultraviolet light, a high stability to heat and a large elastic constant. A liquid crystal display device including the composition has characteristics such as a wide temperature range in which the device can be used, a short response time, a large voltage holding ratio, a low threshold voltage, a large contrast ratio and a long service life, and thus can be used for a liquid crystal projector, a liquid crystal television and so forth.

What is claimed is:

1. A compound, represented by formula (1):

(1)

wherein, in formula (1),
$R^1$ is alkyl having 3 to 15 carbons, alkyl having 2 to 15 carbons in which at least one of —$CH_2$— is replaced by —O— or alkenyl having 4 to 15 carbons, and in the groups, at least one of hydrogen may be replaced by fluorine or chlorine;
a is an integer from 4 to 12; and
$R^2$ is a group represented by formula (1a), formula (1b) or formula (1c):

(1a)

(1b)

(1c)

wherein, in formula (1a), formula (1b) and formula (1c),
$S^1$ and $S^2$ are independently a single bond or alkylene having 1 to 10 carbons, and in the alkylene, at least one of —$CH_2$— may be replaced by —O—, —NH—, —CO—, —COO—, —OCO— or —OCOO—, and at least one of —$(CH_2)_2$— may be replaced by —CH=CH—, and in the groups, at least one of hydrogen may be replaced by fluorine or chlorine;
$S^3$ is >CH— or >N—;
$S^4$ is >C< or >Si<;
$X^1$ is —OH, —$NH_2$ or a group represented by —$OR^3$, —$N(R^3)_2$ or —$Si(R^3)_3$, in which $R^3$ is hydrogen or alkyl having 1 to 10 carbons, and in the alkyl, at least one of —$CH_2$— may be replaced by —O—, at least one of —$(CH_2)_2$— may be replaced by —CH=CH—, and in the groups, at least one of hydrogen may be replaced by fluorine or chlorine;
in which, in formula (1), a sum of carbons in $R^1$, $S^1$, $S^2$, $S^3$, $S^4$ and —$(CF_2)_a$— is at least 11; and
in which, a is 5, 7, 9, 10, 11 or 12 when $R^2$ is a group represented by formula (1a), $S^1$ is —$(CH_2)_2$— and $X^1$ is —OH; and a is 4, 5, 6, 7, 9, 10, 11 or 12 when $R^2$ is a group represented by formula (1a), $S^1$ is —$(CH_2)_3$— and $X^1$ is —OH.

2. The compound according to claim 1, wherein, in formula (1), $R^2$ is a group represented by formula (1a) or (1b).

3. The compound according to claim 1, wherein, in formula (1), $R^2$ is a group represented by formula (1a) or (1b), and in formula (1a) $X^1$ is —OH and in formula (1b), $X^1$ is —OH, —$NH_2$ or a group represented by $Si(R^3)_3$, in which $R^3$ is alkyl having 1 to 10 carbons or alkoxy having 1 to 9 carbons.

4. The compound according to any one of claims 1 to 3, represented by formula (1-1) or (1-2):

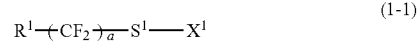
(1-1)

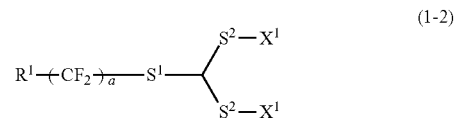
(1-2)

wherein, in formula (1-1) and formula (1-2),
$R^1$ is alkyl having 3 to 15 carbons, alkoxy having 2 to 14 carbons, alkoxyalkyl having 2 to 14 carbons or alkenyl having 4 to 15 carbons;
a is an integer from 4 to 7;
$S^1$ and $S^2$ are independently a single bond or alkylene having 1 to 5 carbons, and in the alkylene, one of —$CH_2$— may be replaced by —O— or —NH—, and one of —$(CH_2)_2$ may be replaced by —CH=CH—;
$X^1$ is —OH, —$NH_2$ or a group represented by —$Si(R^3)_3$, in which $R^3$ is alkyl having 1 to 5 carbons or alkoxy having 1 to 4 carbons;
in which, in formula (1-1), a sum of carbons in $R^1$, $S^1$ and —$(CF_2)_a$— is at least 11; and a is 5 or 7 when $S^1$ is —$(CH_2)_2$— and $X^1$ is —OH; and
in which, in formula (1-2), a sum of carbons in $R^1$, $S^1$, $S^2$, —$(CF_2)_a$— is at least 10.

5. The compound according to claim 1, represented by formula (1-3) or (1-4):

(1-3)

-continued

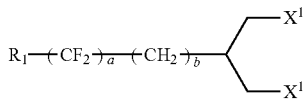
(1-4)

wherein, in formula (1-3) and formula (1-4),
$R^1$ is alkyl having 3 to 10 carbons, alkoxy having 2 to 9 carbons, alkoxyalkyl having 2 to 9 carbons or alkenyl having 4 to 10 carbons;
a is an integer from 4 to 7;
b is an integer from 1 to 3; and
$X^1$ is —OH, —$NH_2$, —$Si(CH_3)_3$, —$Si(C_2H_5)_3$, —$Si(OCH_3)_3$ or —$Si(OC_2H_5)_3$;
in which, in formula (1-3), a sum of carbons in $R^1$, —$(CF_2)_a$— and —$(CH_2)_b$— is at least 11; and a is 5 or 7 when b is 2 and $X^1$ is —OH; and
in which, in formula (1-4), a sum of carbons in $R^1$, —$(CF_2)_a$— and —$(CH_2)_b$— is at least 8.

6. The compound according to claim 1, represented by any one of formulas (1-5) to (1-18):

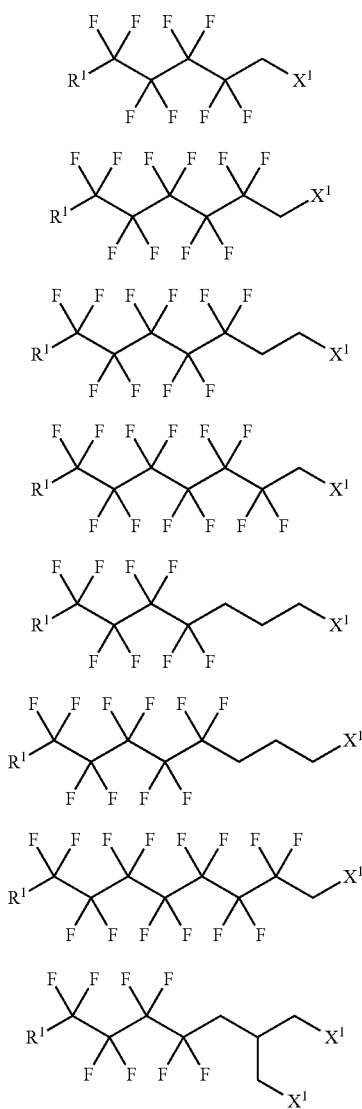

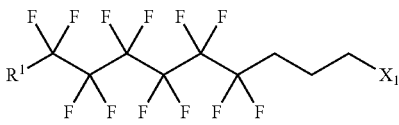
(1-13)

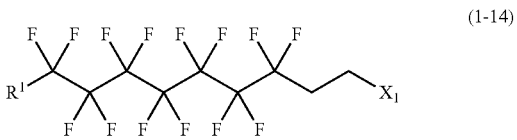
(1-14)

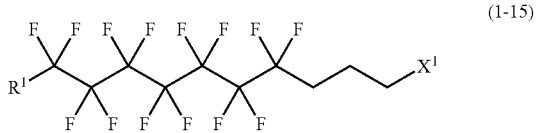
(1-15)

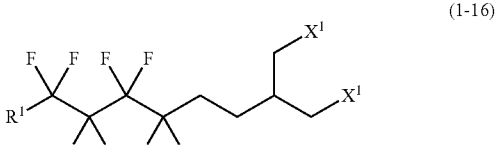
(1-16)

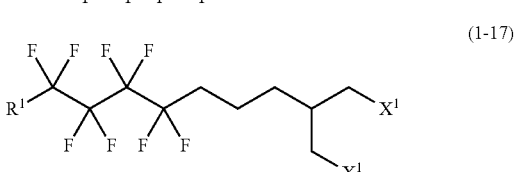
(1-17)

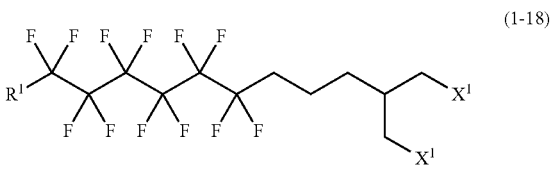
(1-18)

wherein, in formula (1-5) to formula (1-11) or formula (1-13) through (1-15), $X^1$ is —OH; wherein, in formula (1-12) or formula (1-16) to formula (1-18), $X^1$ is —OH, —$Si(CH_3)_3$ —$Si(C_2H_5)_3$, —$Si(OCH_3)_3$ or —$Si(OC_2H_5)_3$; in formula (1-5), $R^1$ is alkyl having 6 to 10 carbons, alkoxyalkyl having 6 to 9 carbons or alkenyl having 6 to 10 carbons; in formula (1-6), $R^1$ is alkyl having 5 to 10 carbons, alkoxyalkyl having 5 to 9 carbons or alkenyl having 5 to 10 carbons; in formula (1-7) to formula (1-9), $R^1$ is alkyl having 4 to 10 carbons, alkoxyalkyl having 4 to 9 carbons or alkenyl having 4 to 10 carbons; in formula (1-10) to formula (1-12), $R^1$ is alkyl having 3 to 10 carbons, alkoxyalkyl having 3 to 9 carbons or alkenyl having 4 to 10 carbons; and in formula (1-13) to formula (1-18), $R^1$ is alkyl having 3 to 10 carbons, alkoxy having 2 to 9 carbons or alkenyl having 4 to 10 carbons.

7. The compound according to claim 1, represented by any one of formulas (1-19) to (1-32):

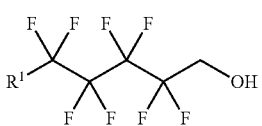
(1-19)

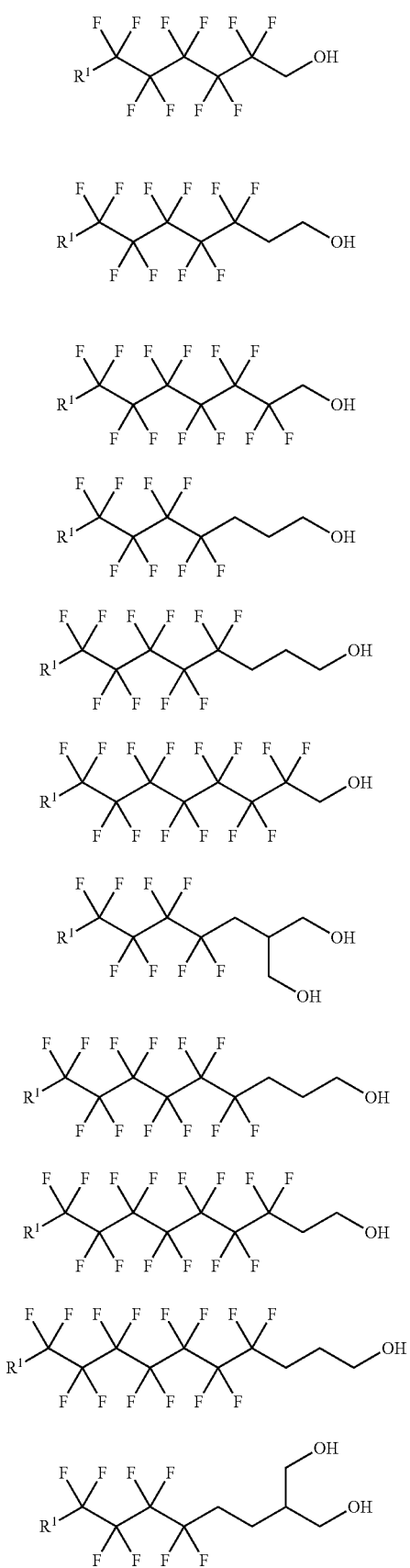

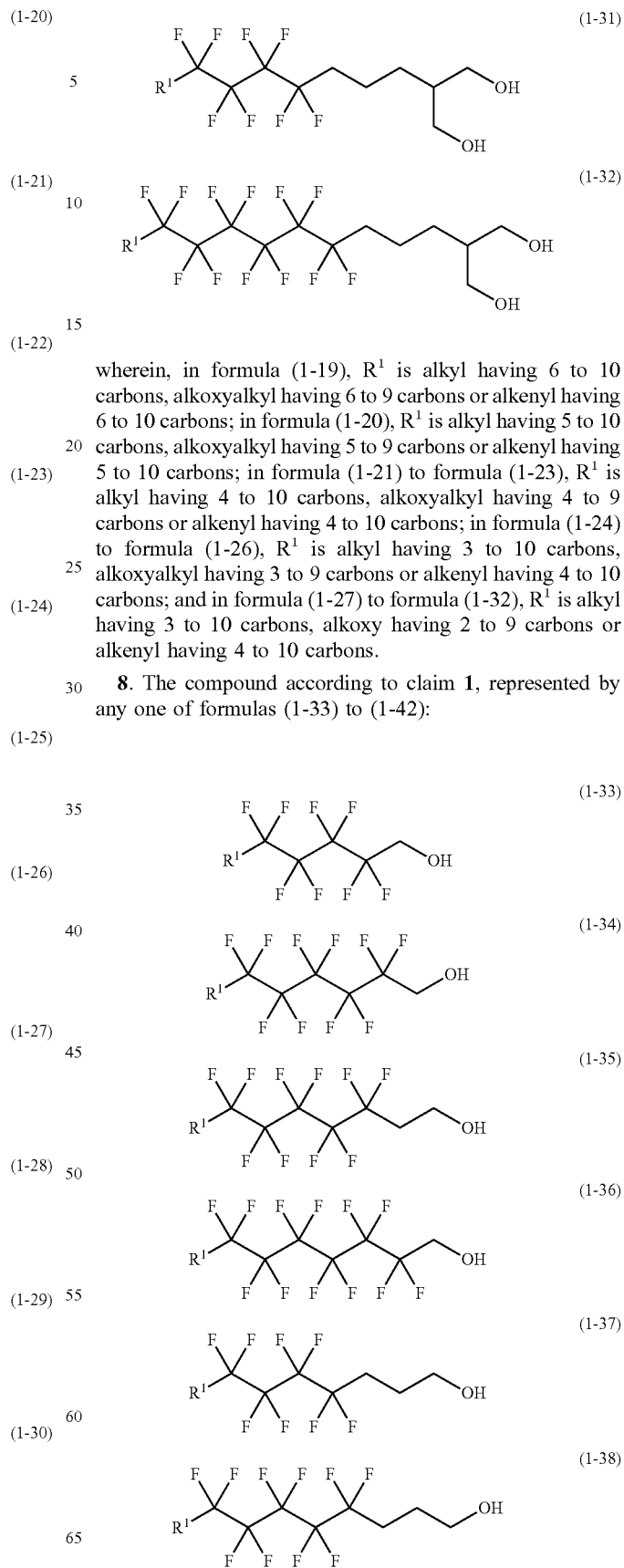

wherein, in formula (1-19), $R^1$ is alkyl having 6 to 10 carbons, alkoxyalkyl having 6 to 9 carbons or alkenyl having 6 to 10 carbons; in formula (1-20), $R^1$ is alkyl having 5 to 10 carbons, alkoxyalkyl having 5 to 9 carbons or alkenyl having 5 to 10 carbons; in formula (1-21) to formula (1-23), $R^1$ is alkyl having 4 to 10 carbons, alkoxyalkyl having 4 to 9 carbons or alkenyl having 4 to 10 carbons; in formula (1-24) to formula (1-26), $R^1$ is alkyl having 3 to 10 carbons, alkoxyalkyl having 3 to 9 carbons or alkenyl having 4 to 10 carbons; and in formula (1-27) to formula (1-32), $R^1$ is alkyl having 3 to 10 carbons, alkoxy having 2 to 9 carbons or alkenyl having 4 to 10 carbons.

8. The compound according to claim 1, represented by any one of formulas (1-33) to (1-42):

(1-39) 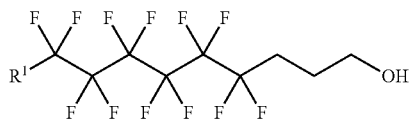

(1-40) 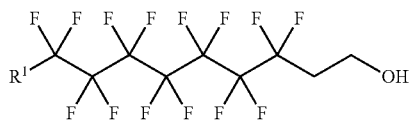

(1-41) 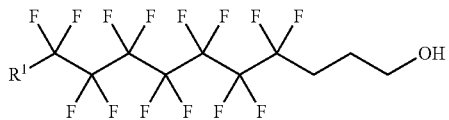

(1-42) 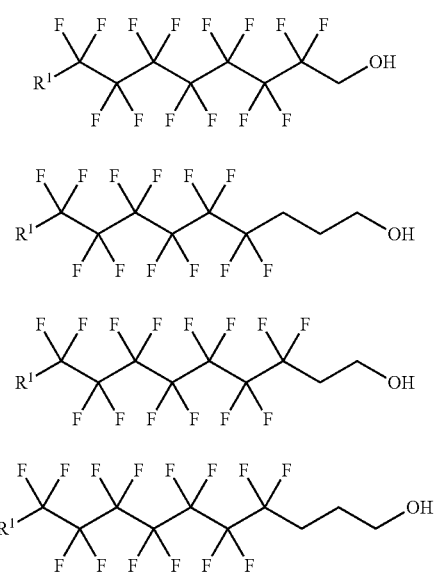

wherein, in formula (1-33), $R^1$ is alkyl having 6 to 10 carbons or alkoxyalkyl having 6 to 9 carbons; in formula (1-34), $R^1$ is alkyl having 5 to 10 carbons or alkoxyalkyl having 5 to 9 carbons; in formula (1-35) to formula (1-37), $R^1$ is alkyl having 4 to 10 carbons or alkoxyalkyl having 4 to 9 carbons; in formula (1-38) to formula (1-39), $R^1$ is alkyl having 3 to 10 carbons or alkoxyalkyl having 3 to 9 carbons; and in formula (1-40) to formula (1-42), R is alkyl having 3 to 10 carbons or alkoxy having 2 to 9 carbons.

9. The compound according to claim 1, represented by any one of formulas (1-43) to (1-48):

(1-43) 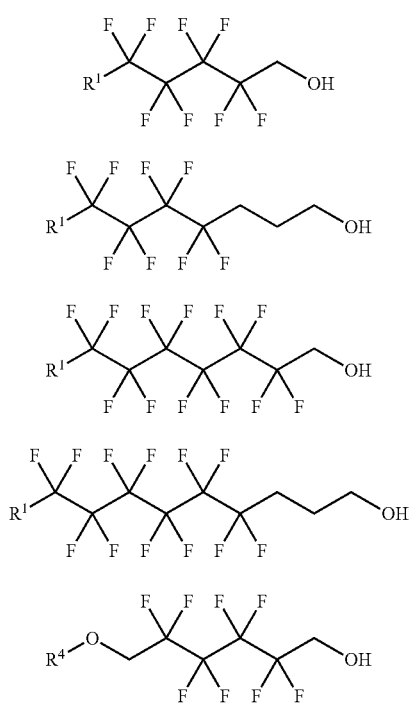

(1-44)

(1-45)

(1-46)

(1-47)

(1-48) 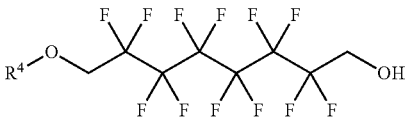

wherein, in formula (1-43), $R^1$ is alkyl having 6 to 10 carbons; in formula (1-44) and formula (1-45), $R^1$ is alkyl having 4 to 10 carbons; in formula (1-46), $R^1$ is alkyl having 3 to 10 carbons; in formula (1-47), $R^4$ is alkyl having 5 to 8 carbons; and in formula (1-48), $R^4$ is alkyl having 3 to 8 carbons.

10. A liquid crystal composition, containing at least one compound according to claim 1 as a first additive.

11. The liquid crystal composition according to claim 10, further containing at least one compound selected from the group of compounds represented by formulas (2) to (4):

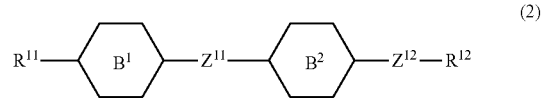 (2)

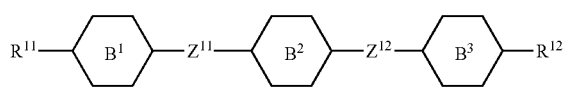 (3)

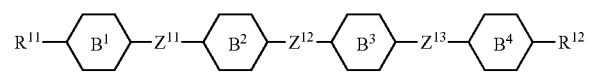 (4)

wherein, in formula (2) to formula (4), $R^{11}$ and $R^{12}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

12. The liquid crystal composition according to claim 10, further containing at least one compound selected from the group of compounds represented by formulas (5) to (7):

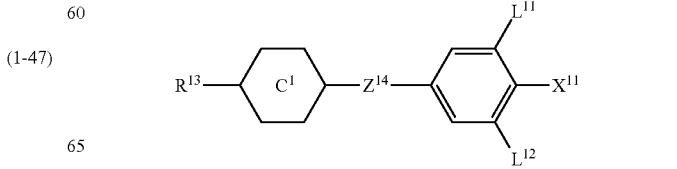 (5)

-continued

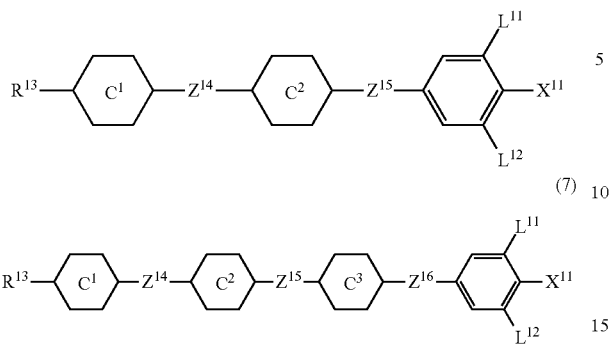

(6)

(7)

wherein, in formula (5) to formula (7),
$R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$X^{11}$ is fluorine, chlorine, —$OCF_3$—$OCHF_2$—$CF_3$—$CHF_2$, —$CH_2F$, —$OCF_2CHF_2$ or —$OCF_2CHFCF_3$;
ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and
$L^{11}$ and $L^{12}$ are independently hydrogen or fluorine.

13. The liquid crystal composition according to claim 10, further containing at least one compound selected from the group of compounds represented by formula (8):

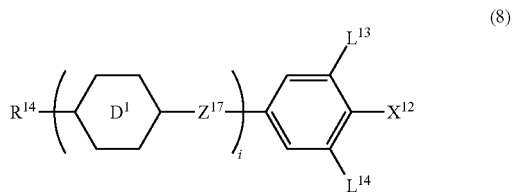

(8)

wherein, in formula (8),
$R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$X^{12}$ is or —C≡N or —C≡C—C≡N;
ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;
$Z^{17}$ is a single bond, —$CH_2CH_2$—, —C≡C—, —COO—, —$CF_2O$—, —$OCF_2$— or —$CH_2O$—;
$L^{13}$ and $L^{14}$ are independently hydrogen or fluorine; and
i is 1, 2, 3 or 4.

14. The liquid crystal composition according to claim 10, further containing at least one compound selected from the group of compounds represented by formulas (9) to (15):

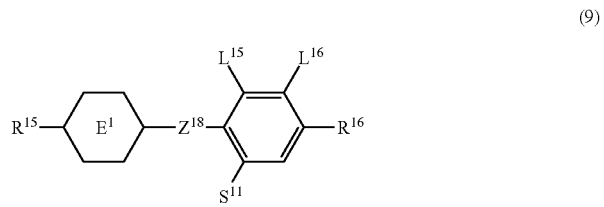

(9)

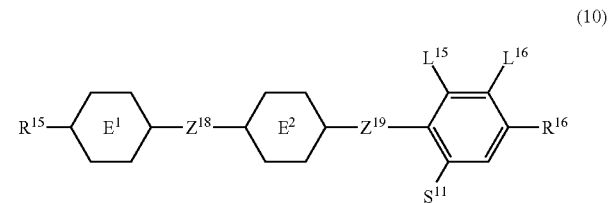

(10)

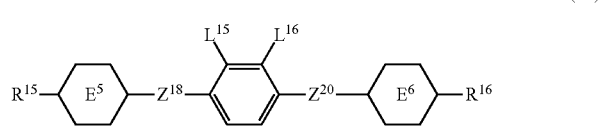

(11)

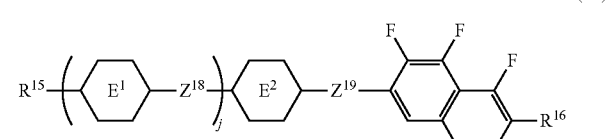

(12)

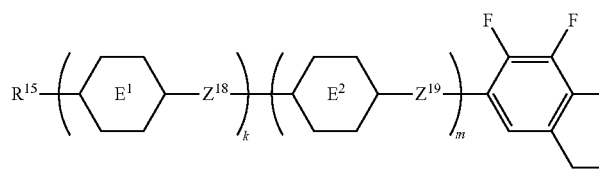

(13)

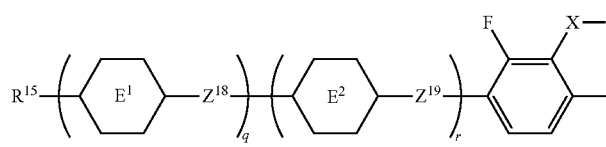

(14)

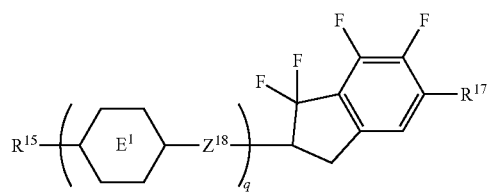

(15)

wherein, in formula (9) to formula (15),
$R^{15}$ and $R^{16}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$R^{17}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
ring $E^1$, ring $E^2$, ring $E^3$ and ring $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;
ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;
$Z^{18}$, $Z^{19}$, $Z^{29}$ and $Z^{21}$ are independently a single bond, —$CH_2CH_2$—, —COO—, —$CH_2O$—, —$OCF_2$— or —$OCF_2CH_2CH_2$—;
$L^{15}$ and $L^{16}$ are independently fluorine or chlorine;
$S^{11}$ is hydrogen or methyl;
X is —CHF— or —$CF_2$—; and
j, k, m, n, p, q, r and s are independently 0 or 1, a sum of k, m, n and p is 1 or 2, a sum of q, r and s is 0, 1, 2 or 3, and t is 1, 2 or 3.

15. The liquid crystal composition according to claim 10, containing at least one polymerizable compound selected from the group of compounds represented by formula (16) as a second additive:

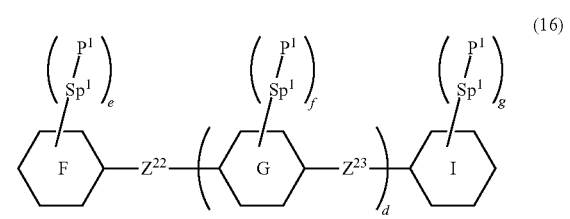

(16)

wherein, in formula (16),
ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen;

ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen;
$Z^{22}$ and $Z^{23}$ are independently a single bond or alkylene having 1 to 10 carbons, and in the alkylene, at least one of —$CH_2$— may be replaced by —O—, —CO—, —COO— or —OCO—, and at least one of —$CH_2CH_2$— may be replaced by —CH=CH—, —C($CH_3$)=CH—, —CH=C($CH_3$)— or —C($CH_3$)=C($CH_3$)—, and in the groups, at least one of hydrogen may be replaced by fluorine or chlorine;
$P^1$, $P^2$ and $P^3$ are independently a polymerizable group;
$Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2CH_2$— may be replaced by —CH=CH— or —C≡C—, and in the groups, at least one of hydrogen may be replaced by fluorine or chlorine;
d is 0, 1 or 2; and
e, f and g are independently 0, 1, 2, 3 or 4, and a sum of e, f and g is 1 or more.

16. The liquid crystal composition according to claim 15, wherein in formula (16) described in claim 15, $P^1$, $P^2$ and $P^3$ are independently a polymerizable group selected from the group of groups represented by formulas (P-1) to (P-5):

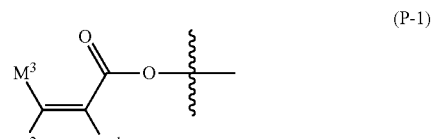

(P-1)

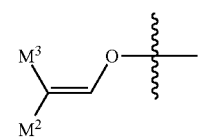

(P-2)

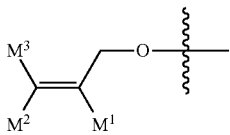
(P-3)

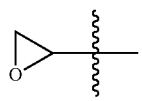
(P-4)

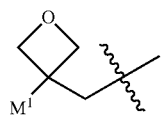
(P-5)

wherein, in formula (P-1) to formula (P-5), $M^1$, $M^2$ and $M^3$ are independently hydrogen, fluorine, alkyl having 1 to 5 carbons, or alkyl having 1 to 5 carbons in which at least one of hydrogen is replaced by halogen.

17. The liquid crystal composition according to claim 10, containing at least one polymerizable compound selected from the group of compounds represented by formulas (16-1) to (16-7) as the second additive:

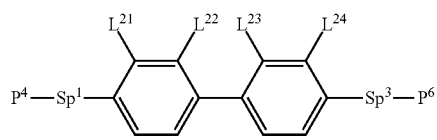
(16-1)

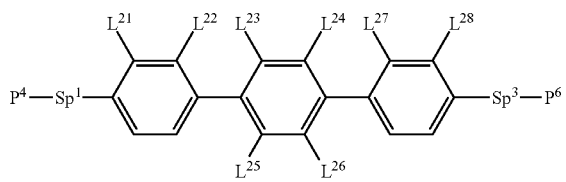
(16-2)

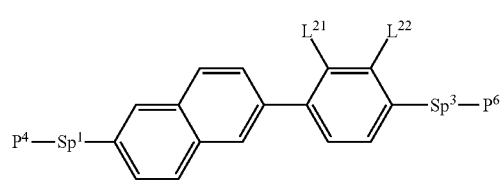
(16-3)

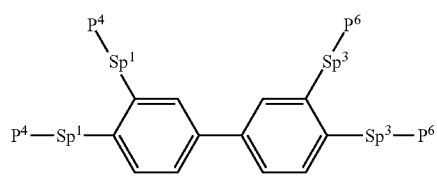
(16-4)

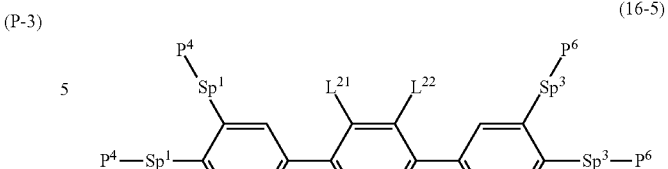
(16-5)

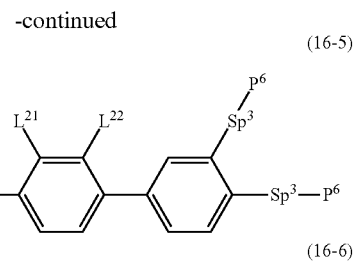
(16-6)

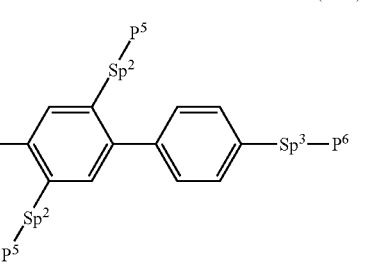
(16-7)

wherein, in formula (16-1) to formula (16-7), $P^4$, $P^5$ and $P^6$ are independently a polymerizable group selected from the group of groups represented by formula (P-1) to formula (P-3), and $M^1$, $M^2$ and $M^3$ are independently hydrogen, fluorine, alkyl having 1 to 5 carbons, or alkyl having 1 to 5 carbons in which at least one of hydrogen is replaced by halogen;

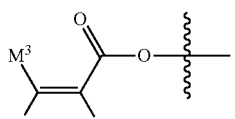
(P-1)

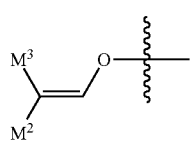
(P-2)

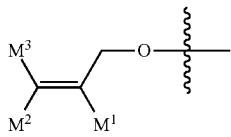
(P-3)

wherein, $L^{21}$, $L^{22}$, $L^{23}$, $L^{24}$, $L^{25}$, $L^{26}$, $L^{27}$ and $L^{28}$ are independently hydrogen, fluorine or methyl; $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, and at least one of —CH$_2$CH$_2$— may be replaced by —CH=CH— or —C≡C—, and in the groups, at least one of hydrogen may be replaced by fluorine or chlorine.

18. The liquid crystal composition according to claim 10, further containing at least one of a polymerizable compound other than the compounds represented by formula (16), a polymerization initiator, a polymerization inhibitor, an optically active compound, an antioxidant, an ultraviolet light absorber, a light stabilizer, a heat stabilizer and an antifoaming agent.

19. A liquid crystal display device, including at least one liquid crystal composition according to claim 10.

20. A liquid crystal composition, containing at least one compound represented by formula (1) as a first additive, wherein formula (1) is:

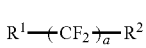  (1)

Wherein in formula (1):
$R^1$ is alkyl having 3 to 15 carbons, alkyl having 2 to 15 carbons in which at least one of —$CH_2$— is replaced by —O— or alkenyl having 4 to 15 carbons, and in the groups, at least one of hydrogen may be replaced by fluorine or chlorine;
a is an integer from 2 to 12; and
$R^2$ is a group represented by formula (1a), formula (1b) or formula (1c):

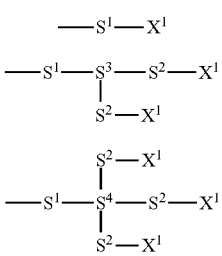

(1a)
(1b)
(1c)

wherein, in formula (1a), formula (1b) and formula (1c),
$S^1$ and $S^2$ are independently a single bond or alkylene having 1 to 10 carbons, and in the alkylene, at least one of —$CH_2$— may be replaced by —O—, —NH—, —CO—, —COO—, —OCO— or —OCOO—, and at least one of —$(CH_2)_2$— may be replaced by —CH=CH—, and in the groups, at least one of hydrogen may be replaced by fluorine or chlorine;
$S^3$ is >CH— or >N—;
$S^4$ is >C< or >Si<;
$X^1$ is —OH, —$NH_2$ or a group represented by —$OR^3$, —$N(R^3)_2$ or —$Si(R^3)_3$, in which $R^3$ is hydrogen or alkyl having 1 to 10 carbons, and in the alkyl, at least one of —$CH_2$— may be replaced by —O—, at least one of —$(CH_2)_2$— may be replaced by —CH=CH—, and in the groups, at least one of hydrogen may be replaced by fluorine or chlorine;
in which, in formula (1), a sum of carbons in R', $S^1$, $S^2$, $S^3$, $S^4$ and —$(CF_2)_a$— is at least 11; and
in which, a is 2, 3, 5, 7, 9, 10, 11 or 12 when $R^2$ is a group represented by formula (1a), $S^1$ is —$(CH_2)_2$— and $X^1$ is —OH; and a is 2, 3, 4, 5, 6, 7, 9, 10, 11 or 12 when $R^2$ is a group represented by formula (1a), $S^1$ is —$(CH_2)_3$— and $X^1$ is —OH.

21. The liquid crystal composition according to claim 20, further containing at least one compound selected from the group of compounds represented by formulas (2) to (4):

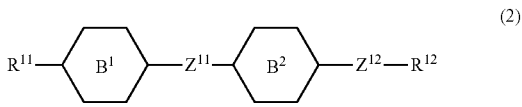 (2)

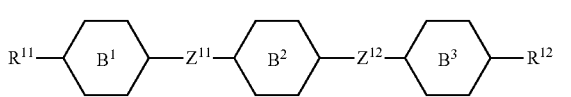 (3)

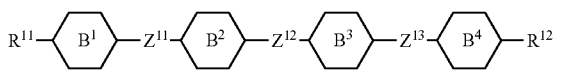 (4)

wherein, in formula (2) to formula (4),
$R^{11}$ and $R^{12}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$ and $Z^{13}$ are independently a single bond, —$CH_2CH_2$—, —CH=CH—, —C≡C— or —COO—.

22. The liquid crystal composition according to claim 20, further containing at least one compound selected from the group of compounds represented by formulas (5) to (7):

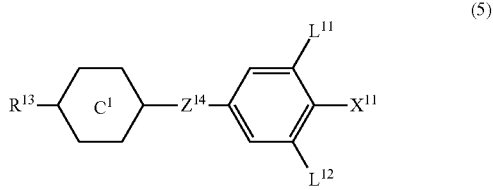 (5)

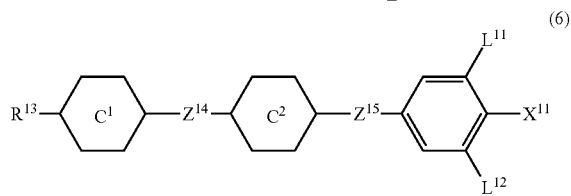 (6)

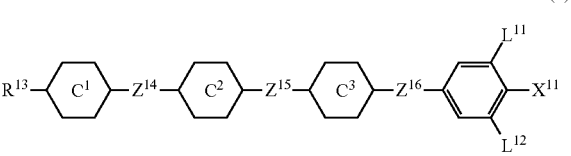 (7)

wherein, in formula (5) to formula (7),
$R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;
$X^{11}$ is fluorine, chlorine, —$OCF_3$—$OCHF_2$—$CF_3$—$CHF_2$, —$CH_2F$, —$OCF_2CHF_2$ or —$OCF_2CHFCF_3$;
ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and $L^{11}$ and $L^{12}$ are independently hydrogen or fluorine.

23. The liquid crystal composition according to claim 20, further containing at least one compound selected from the group of compounds represented by formula (8):

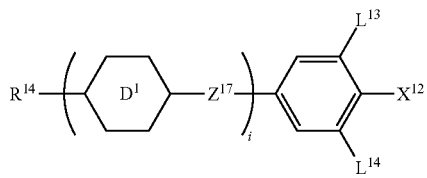

(8)

wherein, in formula (8), $R^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

$X^{12}$ is or —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —CH$_2$CH$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

24. The liquid crystal composition according to claim 20, further containing at least one compound selected from the group of compounds represented by formulas (9) to (15):

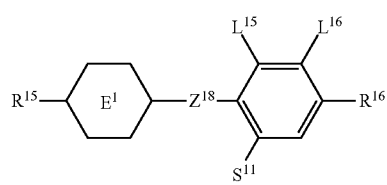

(9)

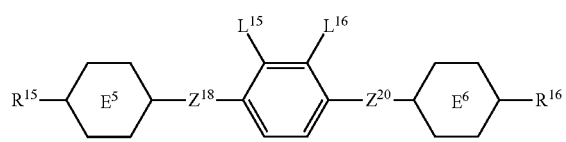

(10)

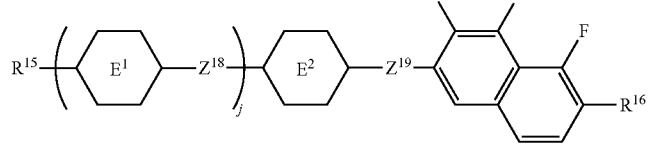

(11)

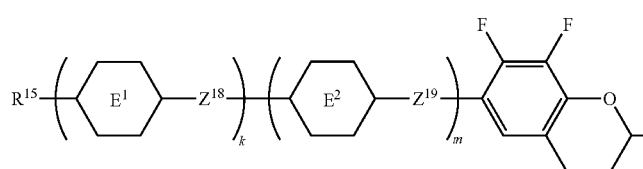

(12)

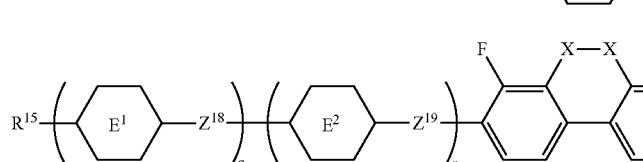

(13)

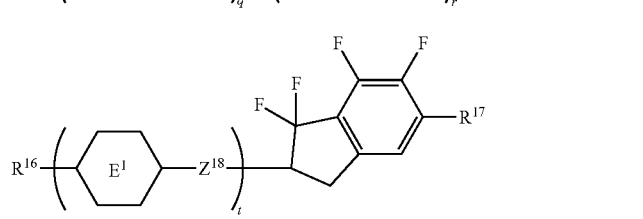

(14)

(15)

wherein, in formula (9) to formula (15),
- $R^{15}$ and $R^{16}$ are independently alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;
- $R^{17}$ is hydrogen, fluorine, alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;
- ring $E^1$, ring $E^2$, ring $E^3$ and ring $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;
- ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;
- $Z^{18}$, $Z^{19}$, $Z^{29}$ and $Z^{21}$ are independently a single bond, —CH$_2$CH$_2$—, —COO—, —CH$_2$O—, —OCF$_2$— or —OCF$_2$CH$_2$CH$_2$—;
- $L^{15}$ and $L^{16}$ are independently fluorine or chlorine;
- $S^{11}$ is hydrogen or methyl;
- X is —CHF— or —CF$_2$—; and
- j, k, m, n, p, q, r and s are independently 0 or 1, a sum of k, m, n and p is 1 or 2, a sum of q, r and s is 0, 1, 2 or 3, and t is 1, 2 or 3.

25. The liquid crystal composition according to claim 20, containing at least one polymerizable compound selected from the group of compounds represented by formula (16) as a second additive:

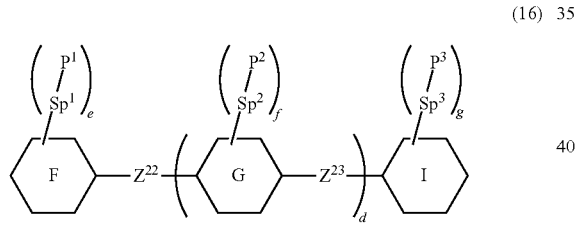

(16)

wherein, in formula (16),
- ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen;
- ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen;
- $Z^{22}$ and $Z^{23}$ are independently a single bond or alkylene having 1 to 10 carbons, and in the alkylene, at least one of —CH$_2$— may be replaced by —O—, —CO—, —COO— or —OCO—, and at least one of —CH$_2$CH$_2$— may be replaced by —CH=CH—, —C(CH$_3$)=CH—, —CH=C(CH$_3$)— or —C(CH$_3$)=C(CH$_3$)—, and in the groups, at least one of hydrogen may be replaced by fluorine or chlorine;
- $P^1$, $P^2$ and $P^3$ are independently a polymerizable group;
- $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, and at least one of —CH$_2$CH$_2$— may be replaced by —CH=CH— or —C≡C—, and in the groups, at least one of hydrogen may be replaced by fluorine or chlorine;
- d is 0, 1 or 2; and
- e, f and g are independently 0, 1, 2, 3 or 4, and a sum of e, f and g is 1 or more.

26. The liquid crystal composition according to claim 25, wherein in formula (16) described in claim 15, $P^1$, $P^2$ and $P^3$ are independently a polymerizable group selected from the group of groups represented by formulas (P-1) to (P-5):

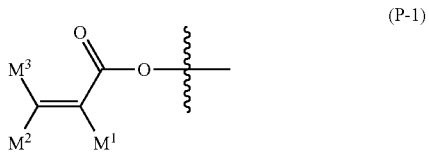

(P-1)

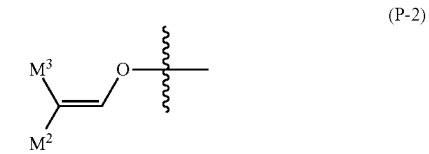

(P-2)

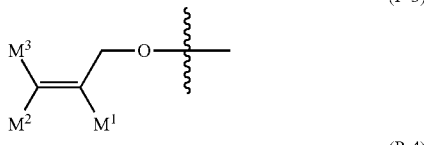

(P-3)

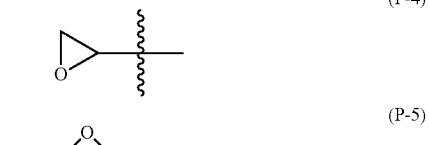

(P-4)

(P-5)

wherein, in formula (P-1) to formula (P-5), $M^1$, $M^2$ and $M^3$ are independently hydrogen, fluorine, alkyl having 1 to 5 carbons, or alkyl having 1 to 5 carbons in which at least one of hydrogen is replaced by halogen.

27. The liquid crystal composition according to claim 20, containing at least one polymerizable compound selected from the group of compounds represented by formulas (16-1) to (16-7) as the second additive:

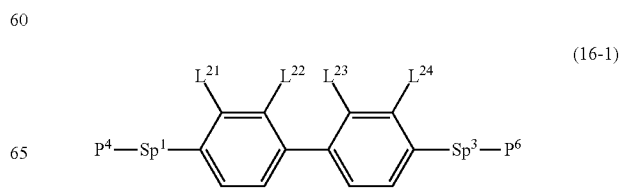

(16-1)

-continued (16-2)
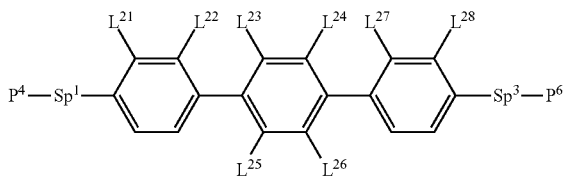

(16-3)
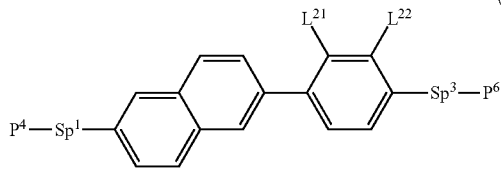

(16-4)
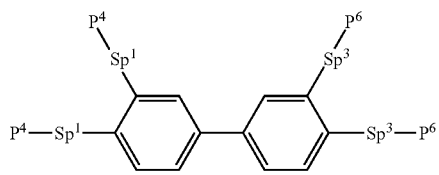

(16-5)
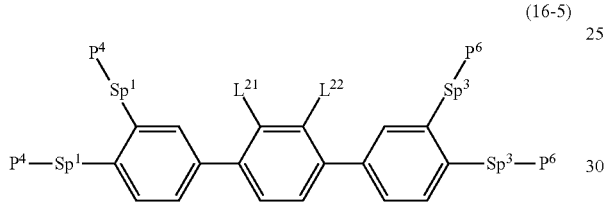

(16-6)
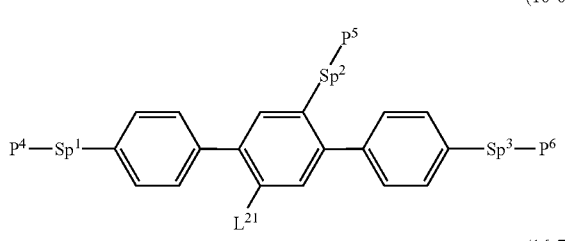

(16-7)
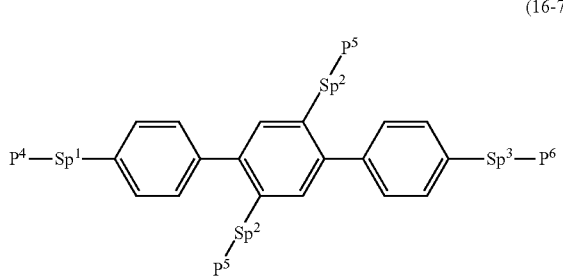

wherein, in formula (16-1) to formula (16-7), $P^4$, $P^5$ and $P^6$ are independently a polymerizable group selected from the group of groups represented by formula (P-1) to formula (P-3), and $M^1$, $M^2$ and $M^3$ are independently hydrogen, fluorine, alkyl having 1 to 5 carbons, or alkyl having 1 to 5 carbons in which at least one of hydrogen is replaced by halogen;

(P-1)
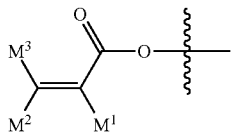

(P-2)
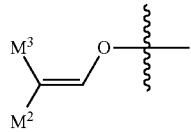

(P-3)
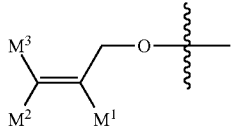

wherein, $L^{21}$, $L^{22}$, $L^{23}$, $L^{24}$, $L^{25}$, $L^{26}$, $L^{27}$ and $L^{28}$ are independently hydrogen, fluorine or methyl; $Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, and at least one of —$CH_2$ $CH_2$— may be replaced by —CH=CH— or —C≡C—, and in the groups, at least one of hydrogen may be replaced by fluorine or chlorine.

28. The liquid crystal composition according to claim 20, further containing at least one of a polymerizable compound other than the compounds represented by formula (16), a polymerization initiator, a polymerization inhibitor, an optically active compound, an antioxidant, an ultraviolet light absorber, a light stabilizer, a heat stabilizer and an antifoaming agent.

29. A liquid crystal display device, including at least one liquid crystal composition according to claim 20.

* * * * *